US011253203B2

(12) United States Patent
Yang

(10) Patent No.: US 11,253,203 B2
(45) Date of Patent: Feb. 22, 2022

(54) OBJECT, METHOD, AND SYSTEM FOR DETECTING HEARTBEAT OR WHETHER OR NOT ELECTRODES ARE IN PROPER CONTACT

(71) Applicant: Chang-Ming Yang, Miaoli (TW)

(72) Inventor: Chang-Ming Yang, Miaoli (TW)

( * ) Notice: Subject to any disclaimer, the term of this patent is extended or adjusted under 35 U.S.C. 154(b) by 1383 days.

(21) Appl. No.: 14/288,259

(22) Filed: May 27, 2014

(65) Prior Publication Data

US 2014/0343392 A1 Nov. 20, 2014

Related U.S. Application Data

(63) Continuation of application No. PCT/CN2012/000417, filed on Mar. 30, 2012.

(30) Foreign Application Priority Data

Nov. 25, 2011 (WO) ................ PCT/CN2011/001963

(51) Int. Cl.
*A61B 5/04* (2006.01)
*A61B 5/00* (2006.01)
(Continued)

(52) U.S. Cl.
CPC .......... *A61B 5/7221* (2013.01); *A61B 5/0245* (2013.01); *A61B 5/252* (2021.01);
(Continued)

(58) Field of Classification Search
CPC . A61B 5/7221; A61B 5/6843; A61B 5/04085; A61B 5/0478; A61B 5/0492; A61B 5/6805
(Continued)

(56) References Cited

U.S. PATENT DOCUMENTS 2,983,273 A 5/1961 Howell
3,795,241 A 3/1974 Golovko
(Continued)

FOREIGN PATENT DOCUMENTS

CN 201139563 Y 10/2008
CN 201394014 Y 2/2010
(Continued)

OTHER PUBLICATIONS

Sankaralingam et al. "Development of textile antennas for body wearable applications and investigations on their performance under bent conditions". Progress in Electromagnetics Research B, vol. 22, 53-71, 2010. (Year: 2010).*
(Continued)

*Primary Examiner* — Joseph A Stoklosa
*Assistant Examiner* — Brian M Antiskay
(74) *Attorney, Agent, or Firm* — Chun-Ming Shih; HDLS IPR Services

(57) ABSTRACT

The invention discloses an object, a method and a system for detecting heartbeat or whether an electrode is in good contact. The heartbeat is detected by arranging multiple textile electrodes on the textile, using ECG equipotential line diagram, considering interference caused of human movement, and designing a separating electrode structure, electrode position, area and lead layout in an innovative manner; the dry electrode or capacitive coupling electrode is selected along with the change of environmental state so as to pick up the ECG signals; the contact between the electrode and the human body can be detected whether it is in a good state or not by measuring the noise, body surface impedance, muscle impedance and the like; in addition, the posture and action of human body can be speculated according to the wave mode and noise of the ECG signals.

18 Claims, 22 Drawing Sheets

(51) Int. Cl.

| | |
|---|---|
| *A61B 5/252* | (2021.01) |
| *A61B 5/276* | (2021.01) |
| *A61B 5/282* | (2021.01) |
| *A61B 5/341* | (2021.01) |
| *A61B 5/369* | (2021.01) |
| *A61B 5/389* | (2021.01) |
| *A61B 5/0245* | (2006.01) |
| *A61N 1/04* | (2006.01) |

(52) U.S. Cl.
CPC .............. *A61B 5/276* (2021.01); *A61B 5/282* (2021.01); *A61B 5/341* (2021.01); *A61B 5/369* (2021.01); *A61B 5/389* (2021.01); *A61B 5/6805* (2013.01); *A61B 5/6843* (2013.01); *A61N 1/0484* (2013.01)

(58) Field of Classification Search
USPC .................................. 600/388–390, 372, 382
See application file for complete search history.

(56) References Cited

U.S. PATENT DOCUMENTS

| | | | | |
|---|---|---|---|---|
| 4,469,105 | A | 9/1984 | Staver | |
| 4,669,468 | A | 6/1987 | Cartmell et al. | |
| 5,348,008 | A * | 9/1994 | Bornn | A61B 5/0006 600/301 |
| 5,445,149 | A * | 8/1995 | Rotolo | A61B 5/04085 600/382 |
| 5,995,861 | A * | 11/1999 | Price | A61B 5/04085 600/372 |
| 6,065,154 | A * | 5/2000 | Hulings | A61N 1/3904 2/102 |
| 6,265,978 | B1 * | 7/2001 | Atlas | G08B 21/06 340/573.1 |
| 2001/0041820 | A1 * | 11/2001 | Woo | A61N 2/06 600/15 |
| 2002/0138125 | A1 * | 9/2002 | Axelgaard | A61B 5/04085 607/149 |
| 2004/0138546 | A1 * | 7/2004 | Reho | A61B 5/04085 600/382 |
| 2004/0260167 | A1 * | 12/2004 | Leonhardt | A61B 5/0536 600/390 |
| 2005/0054941 | A1 * | 3/2005 | Ting | A61B 5/0408 600/529 |
| 2005/0261564 | A1 * | 11/2005 | Ryu | A61B 5/04085 600/388 |
| 2005/0275416 | A1 * | 12/2005 | Hervieux | A41D 13/1281 324/663 |
| 2006/0015027 | A1 * | 1/2006 | Matthews | A61B 5/04085 600/393 |
| 2006/0084881 | A1 * | 4/2006 | Korzinov | G06K 9/00557 600/509 |
| 2006/0094948 | A1 * | 5/2006 | Gough | A61B 5/0408 600/372 |
| 2006/0122471 | A1 * | 6/2006 | Sattler | A41D 13/1281 600/300 |
| 2007/0010750 | A1 * | 1/2007 | Ueno | A61B 5/0408 600/509 |
| 2007/0038057 | A1 * | 2/2007 | Nam | A61B 5/04085 600/388 |
| 2007/0073131 | A1 * | 3/2007 | Ryu | A41D 13/1281 600/388 |
| 2007/0285868 | A1 * | 12/2007 | Lindberg | A61B 5/0245 600/382 |
| 2008/0114232 | A1 * | 5/2008 | Gazit | A61B 5/04085 600/390 |
| 2008/0287770 | A1 * | 11/2008 | Kurzweil | A61B 5/0295 600/388 |
| 2008/0312522 | A1 * | 12/2008 | Rowlandson | A61B 5/6804 600/382 |
| 2009/0018428 | A1 * | 1/2009 | Dias | A41D 13/1281 600/388 |
| 2009/0203984 | A1 | 8/2009 | Dias et al. | |
| 2009/0227856 | A1 * | 9/2009 | Russell | A41D 13/1281 600/388 |
| 2010/0106034 | A1 | 4/2010 | Rytky et al. | |
| 2010/0251454 | A1 * | 10/2010 | Kiernan | A61B 5/0492 2/69 |
| 2012/0172695 | A1 * | 7/2012 | Ko | A61B 5/04 600/372 |
| 2012/0186027 | A1 * | 7/2012 | Gladney | A47C 23/0438 5/716 |
| 2013/0066168 | A1 * | 3/2013 | Yang | A61B 5/0245 600/301 |

FOREIGN PATENT DOCUMENTS

| | | |
|---|---|---|
| CN | 101801456 A | 8/2010 |
| EP | 1559365 A1 | 8/2005 |
| EP | 2072009 A1 | 6/2009 |
| JP | S49022785 A | 2/1974 |
| JP | 55-114605 | 2/1979 |
| JP | S56-8046 A | 1/1981 |
| JP | S63147444 A | 6/1988 |
| JP | 2-139608 | 11/1990 |
| JP | 06-070897 A | 3/1994 |
| JP | 2003-102695 A | 4/2003 |
| JP | 2005/110801 A | 4/2005 |
| JP | 04220235 B2 | 2/2009 |
| JP | 3150-000673 U | 4/2009 |
| JP | 3153409 B2 | 8/2009 |
| JP | 2009-226025 A | 10/2009 |
| JP | 2011-036524 A | 2/2011 |
| WO | 2005/032366 A1 | 4/2005 |

OTHER PUBLICATIONS

Partial Supplementary European Search Report dated Nov. 17, 2015, issued by the European Patent Office, Munich, Germany, in related European Patent Application No. EP-12851285.2 (6 pages).
Office Action dated Nov. 15, 2016, in corresponding Japanese Patent Application No. 2014-542681 (with translation) (10 pages).
Office Action dated Nov. 13, 2016, in corresponding Korean Patent Application No. 10-2016-7024323 (with translation) (9 pages).
Office Action dated Nov. 13, 2016, in corresponding Korean Patent Application No. 10-2016-7024326 (with translation) (8 pages).
PCT International Preliminary Report on Patentability dated Feb. 24, 2012, from corresponding PCT/CN2012/000417, with English translation (169 pages).
Notice of Reasons For Rejection (Office Action) dated Jun. 30, 2015, by the Japan Patent Office in corresponding Japanese Patent Application No. JP 2014-542681 (7 pages), with Google machine-translation (10 pages).
Notification of Grounds For Refusal (Official Action) dated Mar. 11, 2015, by the Korean Intellectual Property Office (KIPO), in corresponding Korean Patent Application No. KR 10-2014-7017093, with English translation (7 pages).
Office Action in corresponding Korean Patent Application No. 10-2014-7017093, dated Jun. 3, 2016 (7 pages).
Extended European Search Report in counterpart European Patent Application No. 12851285.2, dated Apr. 5, 2016 (10 pages).
International Search Report dated Sep. 6, 2012, by the International Bureau of WIPO in corresponding International Application No. PCT/CN2012/000417, with English translation (8 pages).
Office Action issued in corresponding Korean Application No. 10-2014-7017093 dated Jan. 28, 2016, and English translation thereof (8 pages).
Office Action issued in corresponding Japanese Application No. 2014-542681 dated Mar. 15, 2016, and English translation thereof (18 pages).
Office Action issued in corresponding JP Application No. 2017-143790 with English translation dated Jul. 17, 2018 (9 pages).

* cited by examiner

OBJECT, METHOD, AND SYSTEM FOR DETECTING HEARTBEAT OR WHETHER OR NOT ELECTRODES ARE IN PROPER CONTACT

TECHNICAL FIELD

The invention relates to an object, method and system for detecting heartbeat or whether an electrode is in good contact, specifically relates to an object, a method and a system capable of picking up ECG signals, EMG signals or EEG signals and detecting posture, behavior pattern or mental state in a form of being worn on body.

BACKGROUND ART

For patients laying on bed, health people in daily activities, professional or amateur athlete and personnel taking part in high risk work, such as fireman, their physiological status must be known continuously without the wire constraint and obstructing normal activity, so it is necessary to take suitable measures, for example, the first-aid for myocardial infarction patients. It is one of the common solutions to realize the physiological monitoring function on the textiles worn in each day.

For example, U.S. Pat. No. 6,198,394 are provided with sensors (electrodes) on textiles; and the sensors are connected with the circuit by transmission lines. The defect is that some transmission lines suspended outside the textile can obstruct the action of a wearer and is not comfortable.

U.S. Pat. No. 6,080,690 amends the above defect; its realization method is that the transmission lines with insulation layers are woven together with the fibers of common textile so as to connect with the sensors (electrodes) and circuits. But defects still exist, namely, routing needs to arrange on the textile. It is very difficult to arrange multiple transmission lines, because junction is set on the transmission line woven in the textile to connect with the sensors or other electronic components; and it needs complicated processing flow.

U.S. patent application Ser. No. 12/209,288 pastes multiple electrodes on the body by one paster, so that the electrode can contact with the body well without using the clothes. However, the paster is arranged before the chest only and cannot obtain three complete limb lead ECG; and the user feels uncomfortable when the electrode is directly pasted on the body by the paster.

The electrodes of U.S. Pat. No. 7,474,910 are arranged on the fabric by the float yarn; and the electrodes are elastic and capable of stretch. The method for setting electrodes does not consider the effect generated by the friction force between the electrodes and the fabric or human body; it is not the design of three-dimensional space, so it adopts the close-fitting design only; if not, the electrodes and the skin can move relatively when the users walk.

CN201139563Y electrode is the design incapable of moving horizontally on the fabric.

In CN101801456A, the air bag swelling sends the sensing information to the control box 110 by the sensor 114; electric stimulus materials are used for warning the user the harmful conditions instead of strengthening the contact of the electrode and the human body; particularly under the movement behavior, for example, A electrode is pressed while B electrode is not pressed; air or liquid bag enables the air or liquid of A electrode to flow to B electrode and B electrode to contact with human body; the next action is that A electrode is not pressed and B electrode is pressed and the two electrodes contact with human body; the application is connecting pipe mainly; and the technology is not mentioned in CN101801456A.

In conclusion, the textile with physiological monitoring function provided in the existing technology cannot obtain excellent signals by using ECG signals to present on the surface of human body (ECG isopotential surface map) or avoid the sweat interference; the movement interference is reduced by adopting the separating electrode structure; and it can detect whether the electrode is the textile with good contact or not.

CONTENT OF THE INVENTION

It can be known from the existing heart medical science that factors related to ECG signal amplitude collected by body surface comprises:

1. ECG signal amplitude is in direct proportion to myocardial cell quantity (myocardium thickness).

2. ECG signal amplitude is in inverse relation with the distance between the position of physiological electrode and the myocardial cell.

3. ECG signal amplitude is related to the angle formed by the direction of the physiological electrode and the direction of the myocardial electrode; the bigger of the included angle, the smaller of the projection of the ECG signals on the lead and the weaker of the potential.

According to the above principle, some literature ("Simulation studies of the electrocardiogram. I. the normal heart", by W T Miller and D B Geselowitz, Circ. Res. 1978:43) has drawn isopotential surface maps, such as each wave of ECG P, Q, R, S and T by computer simulation; the isopotential surface line of R wave is as shown in FIG. 1 (a), which shows the position relation among the electrode, control box, framework of lead and ECG equipotential line of the excellent embodiment in the invention. The numerical value stands for the potential of the part; and the amplitude of R wave is the potential difference of the two electrodes.

By using the isopotential line diagrams, considering the interference caused by breathing and movement of human body as well as the feasibility of clothing design, the invention puts forwards to a new separating electrode framework as well as position, area and transmission line layout of the electrode in order to reduce the human movement interference. Thereby, the invention aims at overcoming the defect of the textile with physiological monitoring function and providing a new object, a method and a system for detecting heartbeat or whether an electrode is in good contact; the technical solution to be solved is that ECG signals can be continuously picked up by a wearable textile worn on body; the ECG signals can be accurately detected under the precondition of meeting the comfortable wearing and beautiful appearance; it is not interfered by body movement and sweat, etc; and it is very practical.

The other purpose of the invention is to provide an object, a method and a system for detecting heartbeat or whether an electrode is in good contact; the technical solution to be solved is that ECG signals can be picked up by dry electrode or capacitive coupling electrode along the change of environmental state; the processor can select the two best electrodes of the ECG signals by the noise in the ECG signals or the impedance of the electrode; or power consumption is saved by starting different circuits, firmware or software, so it is more practical.

Another purpose of the invention is to provide an object, a method and a system for detecting heartbeat or whether an electrode is in good contact; the technical solution to be solved is that by detecting the impedance or noise of the electrodes to determine whether the electrodes are close-fitting so as to overcome the limit of environment or body posture and pick up ECG signals continuously; and it is more practical.

Another purpose of the invention is to provide an object, a method and a system for detecting heartbeat or whether an electrode is in good contact; the technical solution to be solved is that the human movement, posture, mental state and psychological state can be detected by the noise; the mental state, tread or posture can be judged by the waveform of ECG, so it is more practical.

The purpose of solved solution of the invention is realized by the following solution. An object, a method and a system for detecting heartbeat or whether an electrode is in good contact provided in the invention comprise at least two electrodes and a control box; the electrodes select the position according to the equipotential line diagram; the electrode is provided with a separating structure not fixed on the clothes to reduce the interference caused by the body movement; a processor is arranged in the control box; the processor is provided with a microcontroller, in which firmware is arranged; the firmware can calculate heart rate and judge whether the electrode contacts with human body well or not by the impedance of the electrode or the noise along the ECG signals; and it can be used for detecting the posture, mental state and psychological state.

The firmware of the microcontroller is provided with automatic gain control capable of adjusting the linear range of the signal automatically; and the linear range of the signal can be used for estimating the movement interference. The contact of the electrode and the human body can be detected whether to be good by measuring noise, body surface impedance, muscle impedance and the like.

The object provided in the invention can fix the electrode by the magnetic force so as to reduce the movement interference.

For the object provided in the invention, an elastic container is arranged in the electrode; the container is provided with a hole, through which gas or liquid can get in and out; and the container can store the gas or liquid, generate negative pressure; the electrode is absorbed onto the skin; the electrical conductive liquid can be slowly released because of the capillarity or extrusion so as to solve the problem that the electrode is not fit with the body or it has poor conductivity.

The object provided in the invention can set the air bag or the liquid bag between the electrode and the textile so as to solve the problem that the electrode is not fit with the body.

When the system provided in the invention begins to use, the system detects the impedance between the two electrodes in the behavior act; for example, if the impedance is steady and in the setting range in first ten seconds, the control box is started to detect the ECG signals; if not, the processor informs the user tightening cross straps, increasing conductive liquid, increasing the third electrode or starting the active electrode and the like to improve the signal quality. In a similar way, the method is suitable for EMG, EEG, impedance pneumography, TENS, electric shock, etc.

Compared with the prior art, the invention has obvious advantages and beneficial effects. According to the above solution, the object, the method and the system for detecting heartbeat or whether an electrode is in good contact have the following advantages and beneficial effects:

The invention comprises a textile, on which at least two electrodes are arranged; a conductor is coated outside the electrode; the conductor comprises an elastomer, through which the conductor can be adhered to the human body comfortably; the electrode is connected with the connector by a transmission line; the other end of the connector is connected with the control box; the processor in the control box is provided with an analog circuit (capable of being arranged on the textile) so as to pretreat the physiological signal obtained by the electrode; a microcontroller is arranged in the processor; the physiological signal can be changed to digital signal by the microcontroller; and the physiological signal is sent to other communication equipment by wireless modules, such as Bluetooth and the like. The textile can obtain information by the method for processing the signal; and a system is formed after analyzing the information.

In terms of wearable electrode, the common trouble is that the signal cannot be obtained accurately when the contact of the electrode and the body is poor. The invention adopts 11 methods for detecting whether the contact of the electrode and the skin is poor or not.

The invention can infer the posture and action of the wearer by the contact condition of the electrode and the body; it can remind the wearer timely and detect the activity and mental state. The above method can be applied in EEG, EMG, transcutaneous electrical stimulation treatment and electric shock treatment electrode so as to detect whether the electrode is in a good contact or not.

When the textile is loose, the wearable electrode is likely to be in poor contact with the skin; in order to solve the problem, the invention can increase air bag or liquid bag on the electrode; it is pressurized on occasion to press the electrode to be close to human body. In addition, in order to increase the conductivity, the invention can increase an unpermeable thin layer in the wearable electrode selectively; the conductive moisture can be left in the electrode during the rinsing process; when the textile is worn, the moisture can be slowly released to the electrode and the skin because of capillarity or extrusion. In addition, when the air is contained in the thin layer, the interior of the thin layer is in negative pressure by the elasticity of the thin layer after the extrusion so as to absorb the skin of human body. Meanwhile, the conductive liquid (such as water) on the skin can be absorbed onto the electrode for the sake of electric conduction. In addition, in order to increase the conductivity, the invention installs a flexible conductor between the conductive cloth of the electrode and the elastomer selectively, for example, conductor woven from stainless steel fiber.

The invention discloses eight novel electrode frameworks to reduce the body movement interference.

The invention discloses two methods for judging whether the transmission line is broken or not.

In conclusion, the invention relates to an object, a method and a system for detecting heartbeat or whether an electrode is in good contact. The invention is provided with multiple textile electrodes on the textile. The heartbeat is detected by arranging multiple textile electrodes on the textile, using ECG equipotential line diagram, considering interference caused of human movement, designing a separating electrode structure, electrode position, area and lead layout in an innovative manner; the dry electrode or capacitive coupling electrode is selected along the changed environmental state so as to pick up the ECG signals; the contact between the electrode and the human body can be detected whether it is in a good state or not by measuring the noise, body surface impedance, muscle impedance and the like; in addition, the posture and action of human body can be speculated according to the wave mode and noise of the ECG signals. The invention has remarkable progress on technology and obvious active effect; and it is a novel, progress and practical design.

The above description is the overview of the solution of the invention. The invention can be implemented according to the content of the description in order to know about the technical means of the invention clearly; the excellent embodiments are taken for knowing about the invention, the purposes, the features and advantages easily; and the detail instructions are as follows according to the attached drawings.

The textile in the invention can be clothing, underclothes, coat, sheet, pillow, socks, shoes, scarf, kerchief, glove, apron, waistband, closestool seat, carpet, cap and seat cushion, steering wheel cover, watch, etc.

BRIEF DESCRIPTION OF DRAWINGS

FIG. 1 (b) is the amplifying schematic diagram of the control box in FIG. 1 (a).

FIG. 1 (c) is the schematic diagram of the electrode position decided by the relative displacement distance of the skin during movement.

FIG. 1 (d) is the schematic diagram of left side of the FIG. 1 (c).

FIG. 2 (b) is the profile map of the container in the electrode of the invention.

FIG. 2 (c) is the profile map of the bag formed by uneasily permeable or ventilated glue film in the electrode of the invention.

FIG. 2 (d) is the profile map of the fiber of conductive cloth with sucking disk structure in the invention.

FIG. 3 (b) is the side view of the electrode containing conductive bar in the invention.

FIG. 4 (b) is the side view of the arc-shaped electrode adopting helical transmission line with increased radius in the invention.

FIG. 4 (c) is the side view of the electrode fixed by two suspension bars in the invention.

FIG. 4 (d) is the schematic diagram of the electrode sewed on the textile by the braid as the suspension bar in the invention.

FIG. 5 (b) is the schematic diagram of the electrode of which the side provided with a passage in the invention.

FIG. 5 (c) is the schematic diagram of the textile at the electrode provided with a passage in the invention.

FIG. 5 (d) is the schematic diagram of the textile and the sides of the electrode provided with passages in the invention.

FIG. 6 (b) is the schematic diagram of the electrode provided with a hole, through which the connecting wire can pass in the invention.

FIG. 6 (c) is the schematic diagram of textile at the electrode provided with a hole, through which the connecting wire can pass in the invention.

FIG. 6 (d) is the schematic diagram of the connecting wires passing through the hole on the textile annularly in the invention.

FIG. 7 (b) is the schematic diagram of the second excellent implementation manner that the electrode is arranged on the sliding table in the invention.

FIG. 7 (c) is the schematic diagram of the third excellent implementation manner that the electrode is arranged on the sliding table in the invention.

FIG. 7 (d) is the schematic diagram of the electrode adopting crack separating structure before application of force.

FIG. 7 (e) is the schematic diagram of the electrode adopting crack separating structure under the external force.

FIG. 7 (f) is the schematic diagram of the opening separating electrode.

FIG. 7 (g) is the first schematic diagram that the electrode is provided with an anti-interference layer on the other face of the textile.

FIG. 7 (h) is the second schematic diagram that the electrode is provided with an anti-interference layer on the other face of the textile.

FIG. 8 (b) is the waveform of R wave obtained by the braid as the suspension bar at the side of the electrode when walking.

FIG. 8 (c) is the waveform of R wave obtained by the braid as the suspension bar at the side of the electrode when standing up.

FIG. 8 (d) is the waveform of R wave obtained by the braid as the suspension bar at the side of the electrode when lifting legs in situ.

FIG. 9 (b) is the schematic diagram of the second excellent implementation manner that the double-layer separating structure electrodes are combined by the braid in the invention.

FIG. 9 (c) is the schematic diagram of the third excellent implementation manner that the double-layer separating structure electrodes are combined by the braid in the invention.

FIG. 9 (d) is the waveform of walking R wave obtained double-layer separating structure electrodes in the invention.

FIG. 10 (b) is the schematic diagram of the equipotential line and electrode position of the left R wave in the invention.

FIG. 10 (c) is the schematic diagram of the equipotential line and electrode position of the back R wave in the invention.

FIG. 11 (b) is the ECG signal drawing detected by electrodes at the A and C parts of FIG. 10 (a) in the invention.

FIG. 11 (c) is the ECG signal drawing detected by electrodes at the B and H parts of FIG. 10 (a) in the invention.

FIG. 11 (d) is the ECG signal drawing detected by electrodes at the D and E parts of FIG. 10 (c) in the invention.

FIG. 11 (e) is the ECG signal drawing detected by electrodes at the F and G parts of FIG. 10 (c) in the invention.

FIG. 11 (f) is the ECG signal drawing detected by electrodes at I and J parts of FIG. 10 (b) in the invention.

FIG. 12 (b) is the ECG detected by electrode of which the area is 6*6 cm$^2$ in the invention.

FIG. 12 (c) is the ECG detected by electrode of which the area is 6*9 cm$^2$ in the invention.

FIG. 13 (b) is the waveform of R wave detected at Z and I parts of FIG. 10 (c) and FIG. 10 (b).

FIG. 13 (c) is the waveform of R wave detected at B and I parts of FIG. 10 (a) and FIG. 10 (b) as well as Z part of FIG. 10 (c).

FIG. 13 (d) is the waveform of R wave detected at B and I parts of FIG. 10 (a) and FIG. 10 (b) as well as Z part of FIG. 10 (c) when walking.

FIG. 15 (b) is the ECG obtained when the two arms are front.

FIG. 15 (c) is the ECG obtained when the two arms are back.

FIG. 15 (d) is the ECG obtained when the right arm is front and the left area is rear.

FIG. 16 (b is the waveform of R wave obtained in static when the electrode impedance is 30M Ohms.

FIG. 16 (c) is the waveform of R wave obtained when the electrode impedance is separated from human body in static state.

FIG. 17 (b) is the waveform of R wave obtained during walking when the electrode impedance is 10M Ohms.

FIG. 17 (c) is the waveform of R wave obtained when the electrode impedance is 10M Ohms and lifting legs in situ.

FIG. 17 (d) is the waveform of R wave obtained during in static when the electrode impedance is 0.8M Ohms.

FIG. 17 (e) is the waveform of R wave obtained during walking when the electrode impedance is 0.8M Ohms.

FIG. 17 (f) is the waveform of R wave obtained when the electrode impedance is 0.8M Ohms and lifting legs in situ.

FIG. 18 (b) is the schematic diagram of the second manner for using the two electrodes at the same time in the invention.

FIG. 18 (c) is the schematic diagram of the third manner for using the two electrodes at the same time in the invention.

FIG. 18 (d) is the schematic diagram of the fourth manner for using the two electrodes at the same time in the invention.

FIG. 18 (e) is the schematic diagram of the fifth manner for using the two electrodes at the same time in the invention.

FIG. 18 (f) is the schematic diagram of the sixth manner for using the two electrodes at the same time in the invention.

FIG. 18 (g) is the schematic diagram of the seventh manner for using the two electrodes at the same time in the invention.

FIG. 18 (h) is the schematic diagram of the eighth manner for using the two electrodes at the same time in the invention.

FIG. 18 (i) is the schematic diagram of the ninth manner for using the two electrodes at the same time in the invention.

FIG. 21 (b) is the side view that the two electrodes comprise air bags or liquid bags and are connected and repelled to each other.

FIG. 22 (b) is the schematic diagram adopting annular permanent magnetic substance.

FIG. 22 (c) is the schematic diagram that the permanent magnetic substance is arranged at the two sides of the electrode on the clothes.

FIG. 24 (b) is the waveform of R wave obtained when the surface capacitance is 21.7 nF.

FIG. 25 (b) is the signal generation drawing that the two electrodes are electrically connected in different shapes.

| 5: permanent magnetic substance | 10: snap fastener |
| 20: double-layer structure | 40: electrode |
| 50: control box | 60: connector |
| 65: conductive cloth | 75: conductor |
| 80: transmission line | 82: smooth materials |
| 83: Non-slip bar | 85: textile |
| 90: elastomer | 95: gap |

THE BEST WAY FOR REALIZING THE INVENTION

In order to explain the invention, achieve the technical means adopted for the purpose of the invention and the functions, an object, a method and a system for detecting heartbeat or whether an electrode is in good contact as well as the specific embodiments, structure, method, step, features and functions are explained in details as follows by combining the attached drawings and the best embodiments.

The previous statement of the invention as well as other technical content, features and the functions shall be clearly presented in the detail description of the best embodiment matched with reference drawing. The adopted technical means and functions for achieving the preset purpose shall be deeply and concretely known about by the description for the specific embodiment; the attached drawings provide reference and description only instead of limiting the invention.

The First Embodiment

Daily Clothes

Figures 1A, 1B:
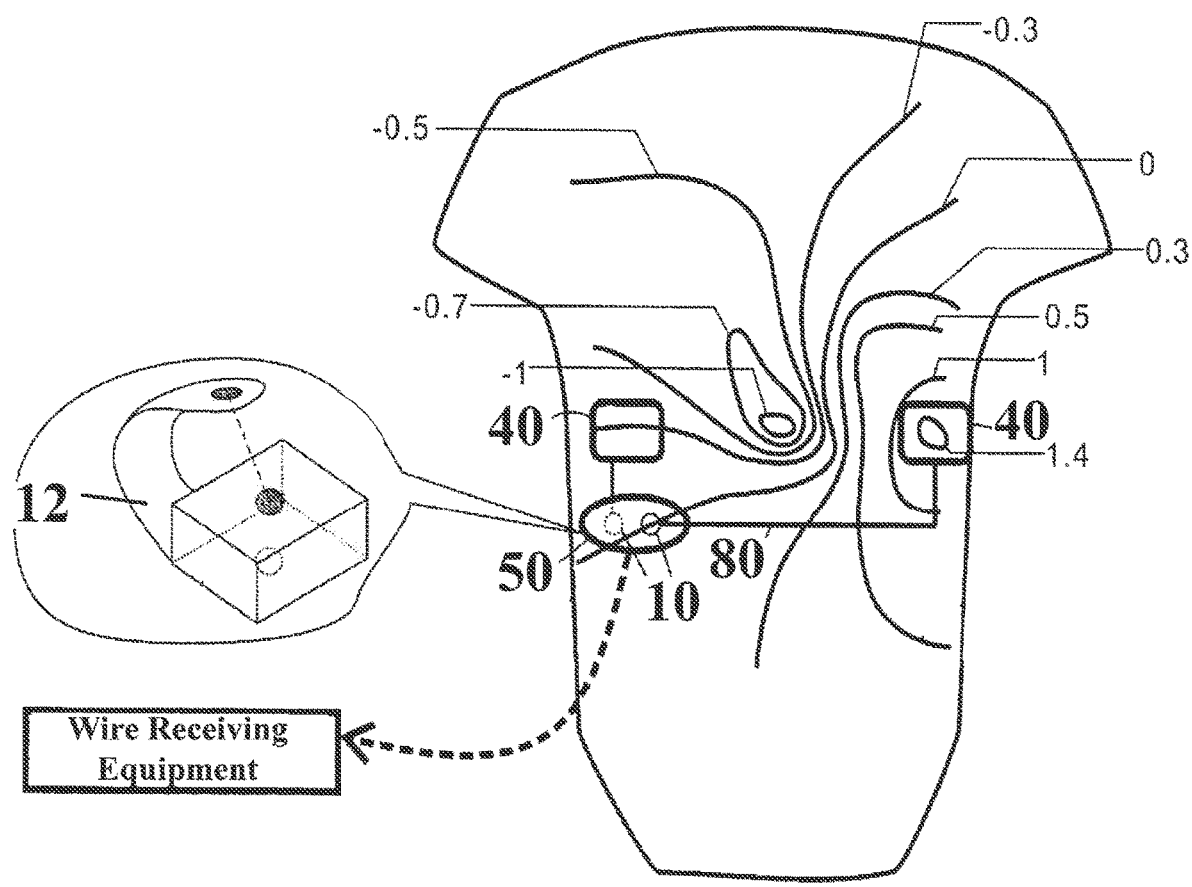
FIG. 1 (a) is the schematic diagram of the position relation among electrode, control box, framework of lead and ECG signal equipotential line.
Figure 1C:
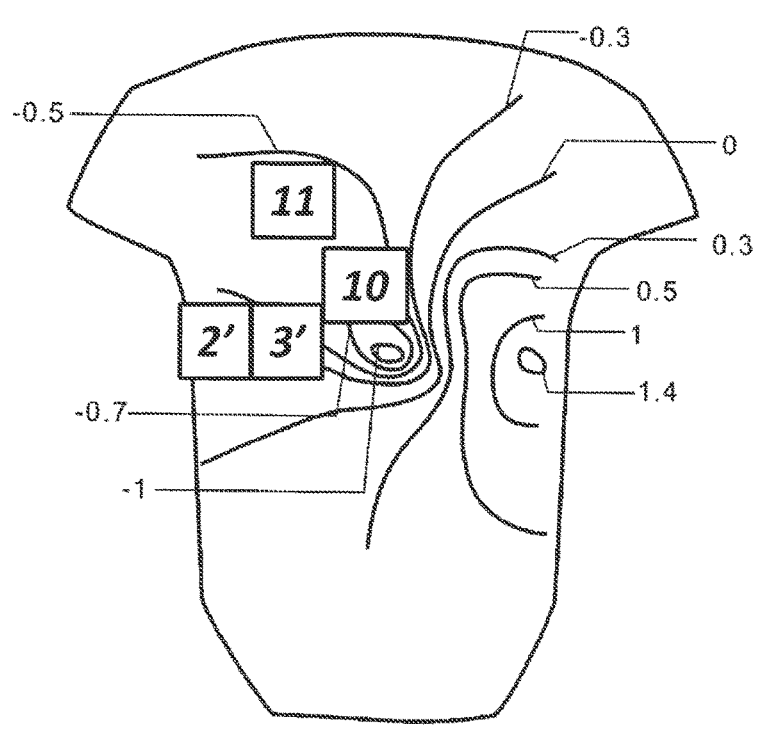
Figure 1D:
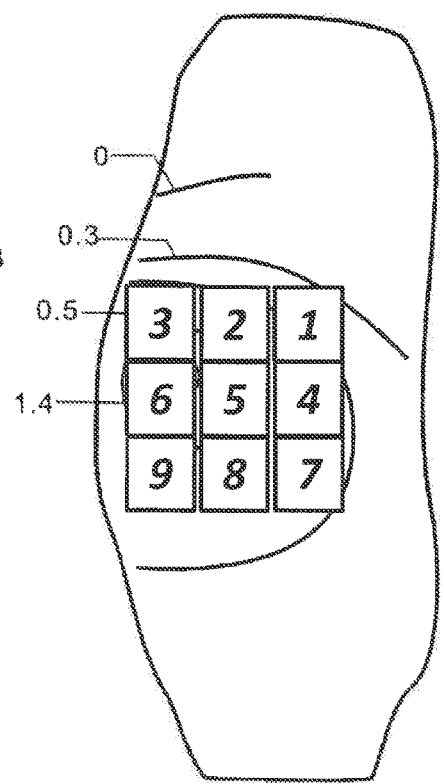
Figure 2A:
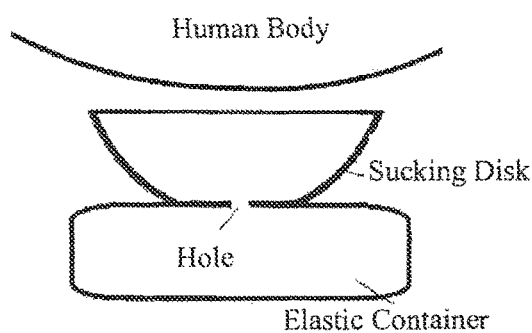
FIG. 2 (a) is the profile map of the electrode with sucking disk structure in the invention.
Figure 2B:
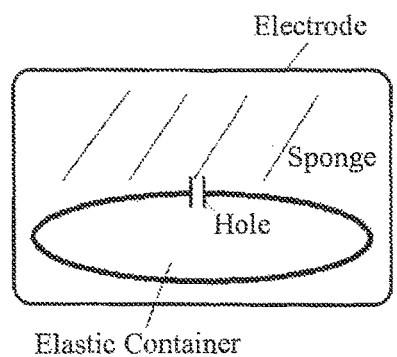
Figure 2C:
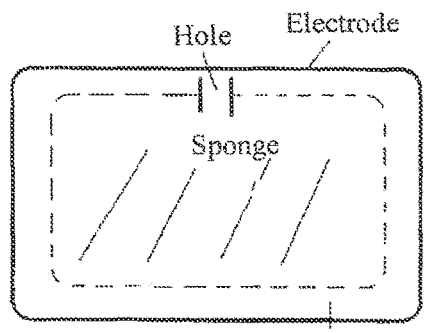
Figure 2D:
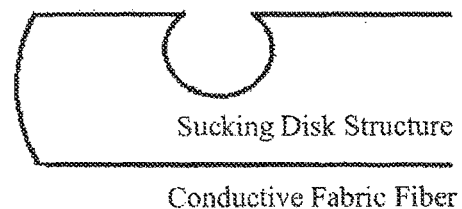

The daily clothes in the invention refer to the clothes worn during the daily activities and are as shown in FIG. 1 (*a*). FIG. 1 (*a*) is the schematic diagram of the position relation among electrode, control box, framework of lead and ECG signal equipotential line. The two electrodes 40 are respectively arranged below the left and right oxters of the daily clothes by the framework in the invention, wherein the electrode 40 below the left oxter is arranged in the area of the highest potential (+1.4); and in order to avoid the respiratory interference and position wearing the underwear of female users, the other electrode 40 is arranged below the right oxter of which the potential is −0.3 instead of the area of the lowest potential (01). Apart from the above two electrodes, the invention can increase a third electrode selectively as the electrode for inputting the feedback current into the human body to reduce the noise or working with the above two electrodes together to obtain three-lead ECG or stray capacitance between the control box and the human body is used as the feedback current to be input into the electrode. The snap fastener 10 is the connector for sending the ECG signals to the control box 50 and as shown in FIG. 1 (*b*); and FIG. 1 (*b*) is the amplifying schematic diagram of the control box in FIG. 1 (*a*). Two snap fasteners are arranged below and above the control box 50 and not located at the same level of the control box 50 so as to avoid being wetted by sweat or rain at the same time and affecting the signal transmission. The snap fasteners 10 can be replaced by conductive (hook-and-loop) Velcro tape to obtain the same function. The water absorbing materials (such as sponges) are arranged around the snap fasteners 10 or the (hook-and-loop) Velcro tape; the bottoms are provided with a waterproof layer, such as impervious materials, hot melt glue thin film, nylon cloth, hydrophobic material, plastic wrap and the like to prevent the sweat affecting the signal transmission. In order to reduce the interference caused when the limb movement pulls the electrodes, the daily clothes can be composed of upper and lower parts or upper, middle and lower parts; each part is made of different materials, for example, the first part of the electrode is made of Lycra cloth with stronger elasticity; or the fabric of the daily clothes is provided with elastic fiber, such as spandex, lycra, elastic yarn, or elastic wire, such as rubber wire; or the fabric of the daily clothes is provided with elastic strip, such as elastic cord with shakeproof and filtering functions; the electrode is fixed on the human body to reduce the body movement interference and reduce noise or obtain the filtering function; and the other parts are made of fabrics easy to extend, so that the Lycra cloth part is not easy to be pulled.

The control box 50 in the invention is electrically connected with the electrode by the snap fastener 10 used as the connector so as to sense the ECG signals. The instrumentation amplifier, band-pass filter, microcontroller and wireless communication module can be arranged in the control box 50 so that the signals can be sent to other communication equipment in a wireless manner and the user is not constrained by the wires.

In order to reduce the body movement interference, the relative displacement distance between the muscle and the skin involved in body movement is measured by the test firstly when selecting the setting position of the electrode; the relative displacement distance is as shown in FIG. 1 (*c*) and FIG. 1 (*d*); FIG. 1 (*c*) is the schematic diagram of the electrode position decided by the relative displacement distance of the skin during movement; and FIG. 1 (*d*) is the schematic diagram of left side of the FIG. 1 (*c*). 6*6 m$^2$ of square paper is respectively arranged on 11 preset positions of the human body; the center of the paper is adhered to human body only; and the other area can move freely. When the human body stands still, the human skin corresponding to the four corners of the paper is marked as the original points; when human body moves, the difference value of the four corners of the paper and the original point is recorded so as to obtain the relative displacement distance of the skin during the movement. The relative displacement distance of the skin caused by the typical body movement is listed in table 1. The surface structure of the electrode and the length of the connecting wire can be designed by watching the surface position displacement condition of human body from the image and the solid state (action drawing of movement line or body surface action); and they are as shown in table 1.

TABLE 1 relative displacement distance of skin of each position under three movements

| Unit cm | Front swing arm in natural walking | | Rear swing arm in natural walking | | Lifting hands upwards in limit | |
| --- | --- | --- | --- | --- | --- | --- |
|  | Horizontal movement | Vertical movement | Horizontal movement | Vertical movement | Horizontal movement | Vertical movement |
| Position 1 | 0.2 | 0.2 | 1 | 0.3 | 0 | 1 |
| Position 2 | 0.3 | 0.5 | 1 | 1 | 0 | 2.5 |
| Position 3 | 0 | 0.2 | 1 | 0.5 | 0 | 2 |

TABLE 1-continued relative displacement distance of skin
of each position under three movements

| Unit cm | Front swing arm in natural walking | | Rear swing arm in natural walking | | Lifting hands upwards in limit | |
|---|---|---|---|---|---|---|
| | Horizontal movement | Vertical movement | Horizontal movement | Vertical movement | Horizontal movement | Vertical movement |
| Position 4 | 0.5 | 0.5 | 0.2 | 0.5 | 0 | 0.8 |
| Position 5 | 0.3 | 0.5 | 0.5 | 0.8 | 0 | 1.5 |
| Position 6 | 0.3 | 0.2 | 0.8 | 0.8 | 0 | 1.0 |
| Position 7 | 0.2 | 0.1 | 0.1 | 0.2 | 0 | 1 |
| Position 8 | 0.3 | 0.1 | 0.1 | 0.2 | 0 | 0.5 |
| Position 9 | 0.1 | 0.2 | 0.1 | 0 | 0 | 0.3 |
| Position 10 | 0 | 0 | 0.2 | 0.1 | 0.5 | 1 |
| Position 11 | 0 | 0.2 | 0.2 | 0.2 | 1 | 1.5 |

The skin of human body is symmetrical in left and right directions, so the relative displacement distance of positions 2, 3 in the left side of human body is the same as that of positions 2', 3' in the right side. It can be seen from table 1 that the minimum relative displacement distance is position 9, secondary is position 1 and then position 3. Positions 9 and 3 have lower potential; and located in the concave side of human body, position 10 is bad for contacting with the electrode. From the potential diagram of R wave in ECG and relative displacement distance of skin, it is better to arrange the electrode at position 3, 3'.

Through a lot of tests, the detecting electrode is better to be arranged below the left and right oxters in the invention; the detecting electrode moves around 2-6 cm levelly along the sternum direction so that the electrode can detect two greatest positions of R wave in 1.4 and −1.0 areas of potential. The cuff of the daily clothes in the invention is greater 2-4 cm than common coats to avoid the movement interference caused by arms movement pulling the clothes and the movement of the electrode position. For female users, the electrode below left and right oxters can move 3-5 cm downwards in order to avoid the corsage.

The body movement shall interfere the detected ECG signals; the movement of skin and clothes during the movement results in movement of electrode relatively to the skin and the clothes; it can generate body movement noise, so the interference is caused. The amplitude of body movement noise is approached to each other and does not change along the position of the electrode. In order to reduce the body movement interference, the embodiment provides seven methods for setting the electrode on the textile; its purpose is that the electrode does not move relatively to the skin during the movement; and the purpose that the electrode does not move relatively to the clothes is hoped to be achieved further. When the invention is used, the impedance between two electrodes 40 in the behavior act shall be detected firstly; for example, in the first ten seconds, if the impedance is steady in the setting range, the control box 50 is started to detect the ECG signals; if not, the control box 50 informs the user tightening cross straps, increasing the conductive liquid, increasing the third electrode or starting the active electrode, referring to "Fabric-Based Active Electrode Design and Fabrication for Health Monitoring Clothing", IEEE TRANSACTIONS ON INFORMATION TECHNOLOGY IN BIOMEDICINE, VOL. 13, NO. 2, 2009) written by Merrit, etc so as to improve the signal quality. The specific seven methods are as follows:

The First Method: Sucking Disk Structure Type

The first sucking disk structure is arranged on the plane that electrodes contact with the human body, wherein the sucking disk structure is made of airtight material with better hydrophily; the sucking disk structure is connected with an elastic container capable of recovering to the original form after being pressed; and there is a hole on the container, so that the liquid or gas can get in and out. The container has a fabric or fiber; siphonage is generated by the fabric or fiber from the inside of the container to the outside of the container; the liquid is transferred to the electrode surface by the container; an elastomer is arranged in the container; when the textile is washed, the conductive liquid (water for washing textile) can be contained in the container; after the textile is stoved or dried, there is still liquid in the container. When the user wears the textile, the liquid in the container can seep according to the capillarity; or when the container is extruded, the liquid in the container is extruded to the electrode. When the container contains the air after the liquid in the container flows out, the interior of the container is in negative pressure by the elasticity of the container after being extruded so as to absorb the skin of human body; the electrode does not move relatively to the human body; meanwhile, the conductive liquid (water) on the skin can be absorbed on the electrode for the sake of electric conduction; it is as shown in FIG. 2 (*a*); and FIG. 2 (*a*) is the profile map of the electrode with sucking disk structure in the invention.

In order to store the liquid in the container well, a valve or a chock plug can be increased on the hole of the container; the valve or the chock plug can be opened so that the liquid can enter during the washing process; and when stoving or drying the textile, the valve or chock plug is closed so as to store the liquid in the container. A switch or valve sealed automatically can be arranged on the hole of the container; when the user inserts the hard pipe into the switch or valve, the liquid can be filled in the container; and when the user pulls the hard pipe out from the switch or valve, the switch or valve is sealed automatically so as to store the liquid in the container.

The other two similar electrode structures are as shown in FIGS. 2 (*b*) and 2 (*c*); FIG. 2 (*b*) is the profile map of the container in the electrode of the invention; FIG. 2 (*c*) is the profile map of the bag formed by uneasily permeable or ventilated glue film in the electrode of the invention, wherein the outer layer of the electrode shown in FIG. 2 (*b*) is the conductive cloth; an elastic container capable of being opened after being pressed is arranged in the electrode; and there is a hole on the container, so that the liquid or gas can get in and out. The function is same as the first sucking disk structure. In addition, elastic materials (such as sponge) with hole gap and capable of absorbing water are arranged between the conductive cloth of the electrode and the container; it can reduce the body movement interference or noise or obtain filtering function; and the elastic materials can store the liquid for the sake of electric conduction. The electrode shown in FIG. 2 (*c*) is a bag formed by an uneasily permeable or ventilated glue film arranged in the conductive cloth; and elastic materials (such as sponge) with hole gap and capable of absorbing water are arranged in the bag. The bag is opened so as to contain the liquid or gas; meanwhile, there is a hole on the bag, so that the liquid or gas can get in and out. The negative pressure generated by the two structures is not used for absorbing the human body totally instead of slowing and reducing the pressure. When the human body moves, the container or bag is pressed to generate new negative pressure; meanwhile, the liquid stored in the container or bag is slowly released. Similarly to FIG. 2 (a), the container and bag in FIG. 2 (b) and FIG. 2 (c) can provide conductive liquid; when being used, the conductive liquid is slowly released to the electrode and the skin. Meanwhile, the container and bag shown in FIG. 2 (b) and FIG. 2 (c) can be used as sucking disks directly, so that the electrode is adhered to the human body.

The second sucking disk structure is the tiny sucking disk structure arranged on the fiber of the conductive cloth of the electrode, so that the air in the sucking disk can be extruded when the electrode is extruded by the human body; meanwhile, the interior of the sucking disk is in negative pressure so as to absorb human body by the elastic materials of the sucking disk; it is as shown in FIG. 2 (d); and FIG. 2 (d) is the profile map of the fiber of conductive cloth with sucking disk structure in the invention. The friction force of the conductive cloth outside the electrode and the human body is greater than that of the textile and the human body by the structure so as to reduce the body movement interference. When the method is applied to the capacitive coupling electrode, common conductive fiber can be used for contacting with the human body.

The sucking disk structure can be separated from the textile by the electrode; a transmission line is arranged on the electrode; the length of the transmission line (not shown in the figure) is L; the electrode of the sucking disk structure is connected with the textile by the transmission line so as to achieve the purpose that the electrode does not move relatively to the human body. At this time, the electrode can resist to the interference generated by the body movement, so that the ECG signals are transmitted to the processor in the control box.

The Second Method: Brushing Structure Type

Figure 3A:
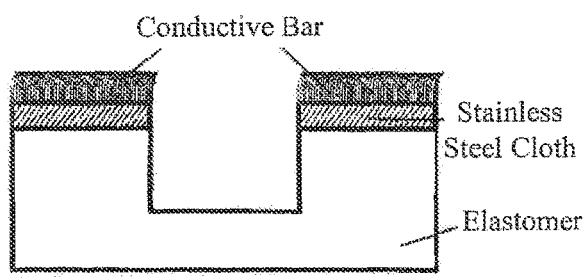
FIG. 3 (a) is the side view of the electrode containing conductive fibers in the invention.
Figure 3B:
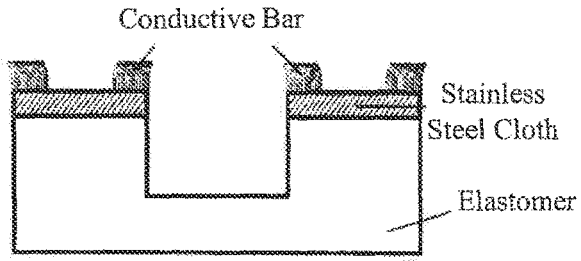

The brushing structure is composed of upright and flexible conductive fibers; the length is L; for example, it is composed of rubber containing graphite, sliver fiber, conductive macromolecule or conductive silica material; it is similar to the brushing structure of toothbrush so as to increase the friction force between the electrodes and the skin, wherein a conductor composed of flexible metal is arranged between the conductive fiber and the electrode, for example, stainless steel cloth woven from stainless steel fiber to increase the conductivity; it is shown as FIG. 3 (a); and FIG. 3 (a) is the side view of the electrode containing conductive fibers in the invention. When the human body moves, the conductive fiber located between the electrode and the skin can maintain the contact of the skin and the electrode in a certain range, so that the skin and the electrode cannot move relatively to enlarge the contact area of the skin and the electrode.

The flexible conductive fiber is easy to irritate the skin and result in inflamed reaction of the skin, so that two or three conductive bars made of flexible and smooth conductive materials are extended on the electrode in the invention, for example, silver fiber conductive cloth, conductive silica bar or macromolecule conductive cloth to replace the brushing structure composed of the conductive fibers; the brushing structure is arranged outside the electrode to increase the friction force between the electrode and the skin and achieve the effect similar to the brushing structure shown in FIG. 3 (a); meanwhile, adverse reaction of skin is not easy to be caused; it is as shown in FIG. 3 (b); and FIG. 3 (b) is the side view of the electrode containing conductive bar in the invention.

The two electrodes shown in FIG. 3 (a) and FIG. 3 (b) can be provided with an elastomer respectively; the electrode can be provided with a transmission line of which the length is L (0.2-3 cm); the electrode is connected with the textile by the transmission line, so the electrode can be separated from the textile (called separating structure below) to achieve the purpose that the electrode does not move relatively to the human body and reduce the body movement interference.

In the method, the friction between the electrode and the human body is greater than that between the electrode and the clothes, so that the electrode does not move relatively to the skin during the movement. In addition, the electrode in the method can be arranged on the clothes by the separating structure so as to achieve the purpose that the electrode does not move along the clothes; and the effect is same as that of the above method.

The Third Method: Suspension Structure Type

Figure 4:
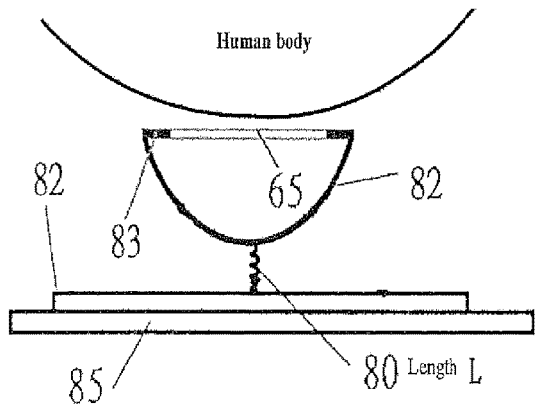
FIG. 4 (a) is the side view of the arc-shaped electrode sliding on the textile in the invention.
Figure 4:
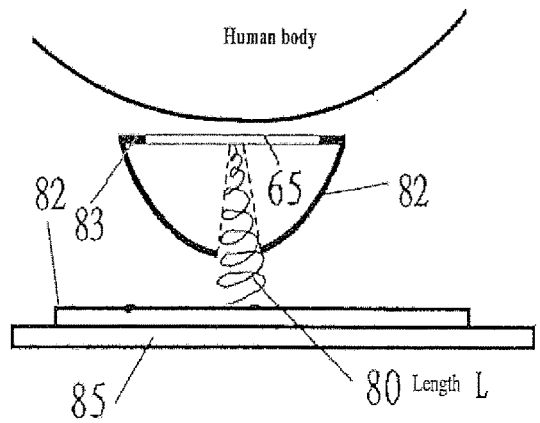
Figure 4:
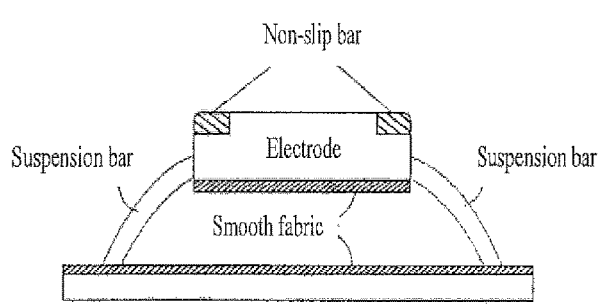
Figure 4:
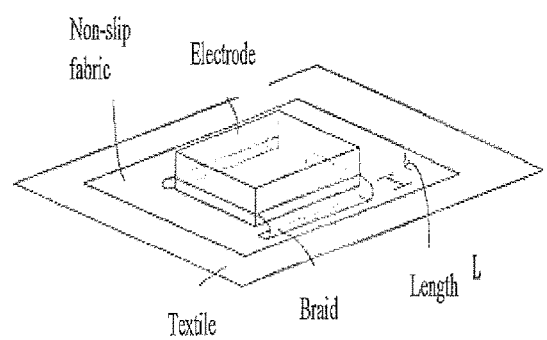

The electrode is arc-shaped as shown in FIG. 4 (a), FIG. 4 (b), FIG. 4 (c) and FIG. 4 (d) or flat type or other type; and the electrode is connected with the textile 85 contacting with human body by the transmission line 80. The transmission line 80 is elastic, for example, the transmission line 80 is woven on the elastic cord or other braids; the suspension length of the transmission line 80 is L (0.5-0.3 cm) in case of relative movement of the electrode and the textile. The surface of the electrode adopts the conductive cloth 65 with greater friction force, such as the conductive cloth with villi structure. At least one face of the contact faces of the electrodes and the textile is made of the smooth material with lower friction force, meanwhile, the materials have a certain rigid, such as lining cloth, waterproof smooth cloth, sheet iron, copper sheet, smooth plastic, stainless steel sheet, glass material or textile covered by Teflon and the like so that the electrode can slide conveniently. An elastomer, conductive silica gel or common textile and the like are arranged in the electrode. The non-slip bar 83 is selectively arranged outside the electrode to increase the friction coefficient between the electrode and the human body; at this time, the surface that the electrode contacts with the textile 85 can be made of smooth materials. When the human body and the textile move relatively, the electrode can slide or roll on the textile by the smooth materials 82 on the electrode; meanwhile, the conductive cloth 65 can contact with the human body still and be fixed so as to receive the signals rather than generating noise. The transmission line between the electrode and the textile 85 can be the helical transmission line with fixed radius shown in FIG. 4 (a); or it is the helical transmission line with increased radius shown in FIG. 4 (b) or folded (folding the braid for three times in FIG. 4 (d) transmission line for stretch. The helical or folded transmission line can be retracted when being lengthened so as to not occupy the space. FIG. 4 (a) is the side view of the arc-shaped electrode sliding on the textile in the invention. FIG. 4 (b) is the side view of the arc-shaped electrode adopting helical transmission line with increased radius in the invention. FIG. 4 (c) is the side view of the electrode fixed by two suspension bars in the invention. FIG. 4 (d) is the schematic diagram of the electrode sewed on the textile by the braid as the suspension bar in the invention.

In addition, the electrode can be flat, so the electrode is connected with the textile by at least two suspension bars of which the length is L, such as the suspension bars woven from nylon yarn or elastic yarn and the like shown in FIG. 4 (c); one suspension bar can be the transmission line; if all suspension bars are non-conductive, the electrode is connected with the textile by another transmission line. The suspension bar comprising the transmission line can be coated with an insulation layer, such as rubber coating copper wire, or not coated with the insulation layer, such as silver fiber; or the whole suspension bar is conductive material, such as stainless steel conductive bar; at this time, the suspension bar can be used as the electrode; the suspension bar can pick up ECG signals when contacting with human body to increase the chance of sensing the ECG signals; meanwhile, the increased transmission line can be reduced. The non-slip bar can be silica gel, rubber or (hook-and-loop) Velcro tape and the like, which can be the conductive materials or used as the electrode.

The suspension bar can be made of the braid with active length L on the electrode; it is shown in FIG. 4 (d); when the braid is combined with the textile, space with 0.2-3 cm of length can be left so that the electrode can move freely. When the human body moves, the electrode can move freely along the skin in the three-dimensional space with 0.2-3 cm of movement range instead of moving relatively to the skin; and it can achieve the purpose that the electrode does not move along the textile. In the embodiment, the non-slip bar 83 is directly woven on the textile 85 by the non-slip fabric so as to achieve the effect that the electrode does not move relatively to the human body and the body movement interference is reduced. When the non-slip fabric is stressed to move on the textile, the friction force relative to the skin is greater than the pulling force relative to the non-slip fabric. The structure of the non-slip fabric on the textile can be applied to other structures in the invention. The non-slip fabric can be silica gel, latex, rubber, villus, (hook-and-loop) Velcro tape or high-tension elastic fabric and the like, such as silk stockings. The braid can comprise transmission line 80 or be the conductive material; and when the braid is used as the electrode, the increased transmission line 80 can be reduced.

The Fourth Method: Passage Structure Type

Figure 5:
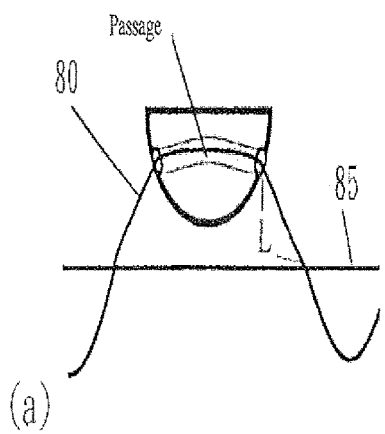
FIG. 5 (a) is the side view of the electrode provided with passage so that the electrode can slide along the transmission line in the invention.
Figure 5:
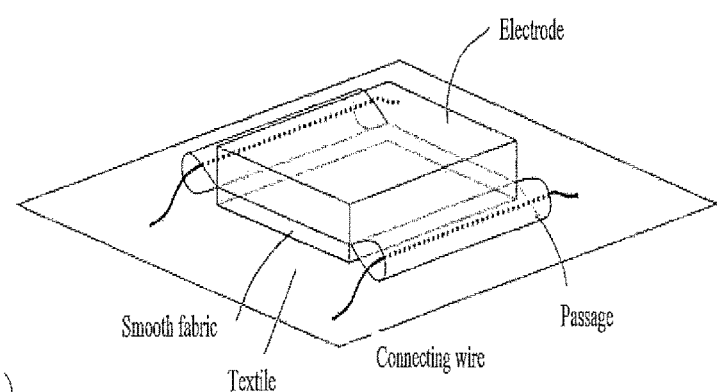
Figure 5:
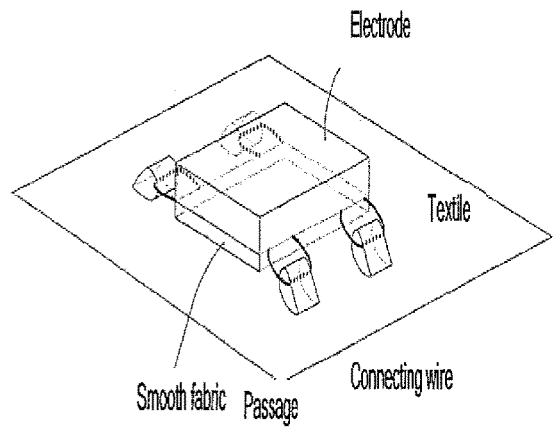
Figure 5:
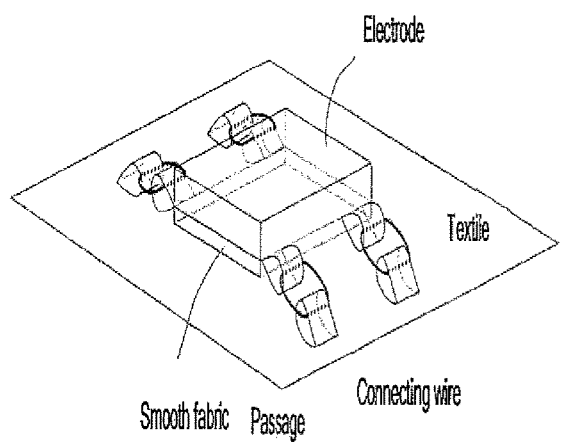

There is no passage in the electrode; the transmission line 80 can slid in the passage; the transmission line has redundant length L on the textile 85 so that the electrode can slid. In addition, if the transmission line 80 and the passage are conductors, another transmission line is not needed to set, shown in FIG. 5 (a); and FIG. 5 (a) is the side view of the electrode provided with passage so that the electrode can slide along the transmission line in the invention. The other example is as shown in FIG. 5 (b); and FIG. 5 (b) is the schematic diagram of the electrode of which the side provided with a passage in the invention. The electrode is the plane structure; the two sides of the electrode are respectively provided with a passage; each passage is provided with a connecting wire so that the electrode is fixed on the textile. The connecting wire can be nylon yarn, elastic yarn, cloth wire, cloth bar, metallic wire, plastic wire, plastic bar, conductive wire or conductive bar, etc; and it is better to select elastic and smooth materials.

In addition, the passage can be set on the textile; a connecting wire is arranged in each passage on the textile; the two ends of the connecting wire are fixed on the electrode, which is as shown in FIG. 5 (c); and FIG. 5 (c) is the schematic diagram of the textile at the electrode provided with a passage in the invention. Or the electrode and the textile are provided with passages, which are connected by the connecting wire, shown in FIG. 5 (d) and FIG. 5 (d) is the schematic diagram of the textile and the sides of the electrode provided with passages in the invention. The redundant length of the connecting wire is L (0.5-3 cm); the two surfaces that the electrode contacts with the clothes are made of smooth materials (such as lining cloth, waterproof smooth cloth, sheet iron, copper sheet, smooth plastic, stainless steel sheet, glass material or textile covered by Teflon and the like so as to reduce the friction force; and the electrode edge can be selectively provided with non-slip bar (not shown) or the non-slip fabric is arranged on the textile to increase the friction force. When the human body moves, the active range of the electrode is 0.2-3 cm of three-dimensional space; the electrode can move actively along the skin instead of moving relatively to the skin; and the purpose that the electrode does not move along the textile is achieved. Conductive material is arranged in the passage; and the conductive material can be coated or not coated with insulation layer. The connecting wire is the transmission line or conductive material, such as conductive cloth made of coating or not coating insulation layer; when the conductive cloth is not coated with the insulation layer, it can be used as electrode to pick up electro-physiological signals when contacting with human body. If the passage and connecting wire are not conductive, another transmission line is added to connect with the electrode to receive signals. The materials of the connecting wire are as shown above; and it is better to select elastic and smooth materials.

The Fifth Method: Perforated Structure Type

Figure 6:
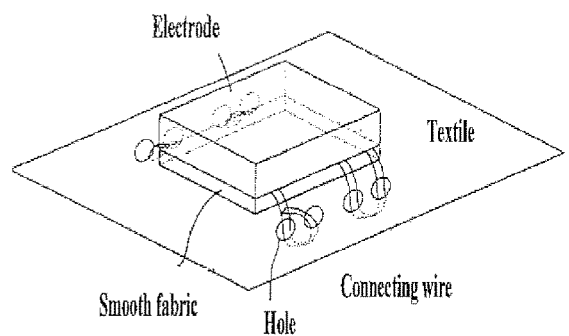
FIG. 6 (a) is the schematic diagram of textile at the electrode provided with a hole, through which the connecting wire can pass in the invention.
Figure 6:
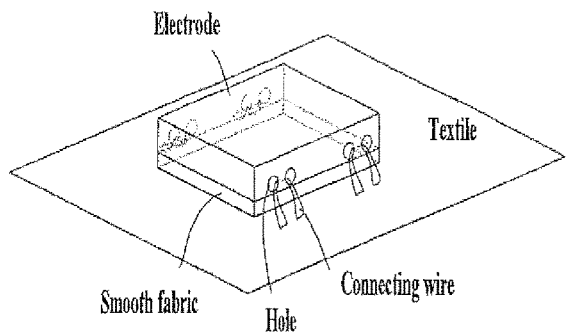
Figure 6:
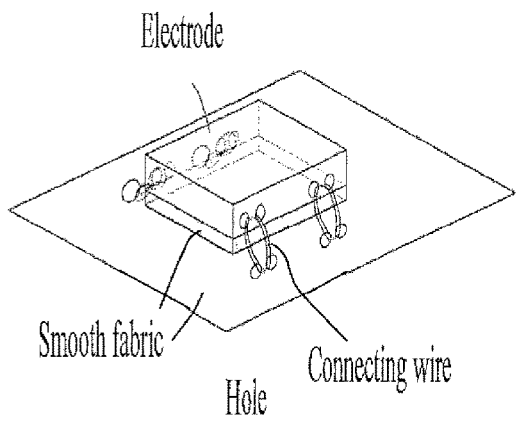
Figure 6:
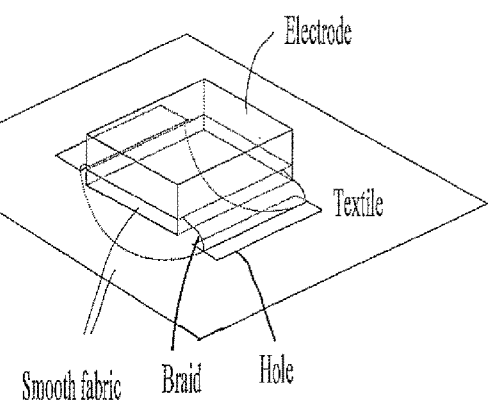

As shown in FIG. 6 (a), FIG. 6 (b), FIG. 6 (c) and FIG. 6 (d), FIG. 6 (a) is the schematic diagram of textile at the electrode provided with a hole, through which the connecting wire can pass in the invention; FIG. 6 (b) is the schematic diagram of the electrode provided with a hole, through which the connecting wire can pass in the invention; FIG. 6 (c) is the schematic diagram of textile at the electrode provided with a hole, through which the connecting wire can pass in the invention; and FIG. 6 (d) is the schematic diagram of the connecting wires passing through the hole on the textile annularly in the invention. There are holes on the electrode and/or textile; the connecting wire can pass through the hole; the contacting face of the electrode and the clothes is made of smooth materials to reduce the friction force; and non-slip bar can be selectively arranged at the edge of the electrode. Apart from being set on the textile shown in FIG. 6 (a), the holes can be arranged on the electrode, shown in FIG. 6 (b); or the electrode and the textile are provided with holes, shown in FIG. 6 (c). The hole can be circular hole shown in FIG. 6 (a), FIG. 6 (b) and FIG. 6 (c) or long and narrow hole shown in FIG. 6 (d); and the braid used as the connecting wire can pass through the hole. The two ends of the braid passing through the hole can be respectively fixed on the textile, electrode or connected to the annular shape. The conductivity of the non-slip bar, hole and the connecting wire is as shown in the third and fourth methods; the sliding length L of the connecting wire is around 0.2-3 cm to reduce the body movement interference effectively. The connecting wire can be the conductive material; if not, another transmission is added. The materials of the connecting wire are as shown in the fourth method.

In the example, if another transmission line is not added, a wireless transmission system is arranged in the electrode to send the signals obtained by the electrode.

All structures in the above methods can be implemented by setting the wireless transmission system in the electrode.

The Sixth Method: Sliding Block Structure Type

Figure 7:
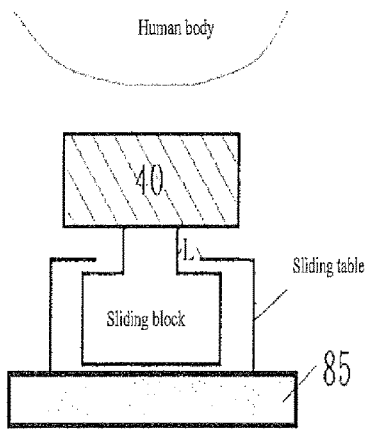
FIG. 7 (a) is the schematic diagram of the first excellent implementation manner that the electrode is arranged on the sliding table in the invention.
Figure 7:
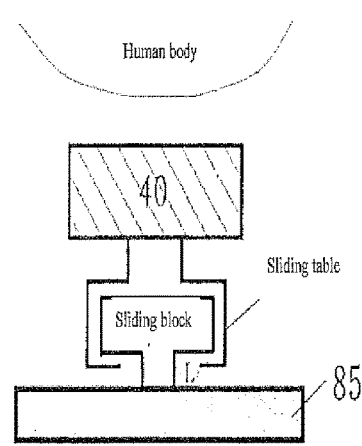
Figure 7:
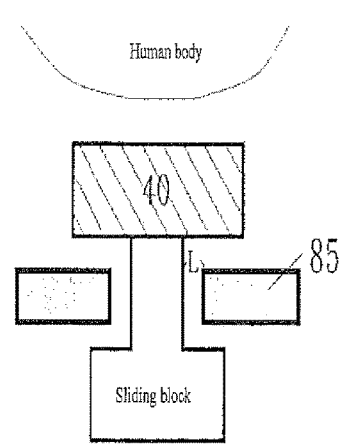
Figure 7:
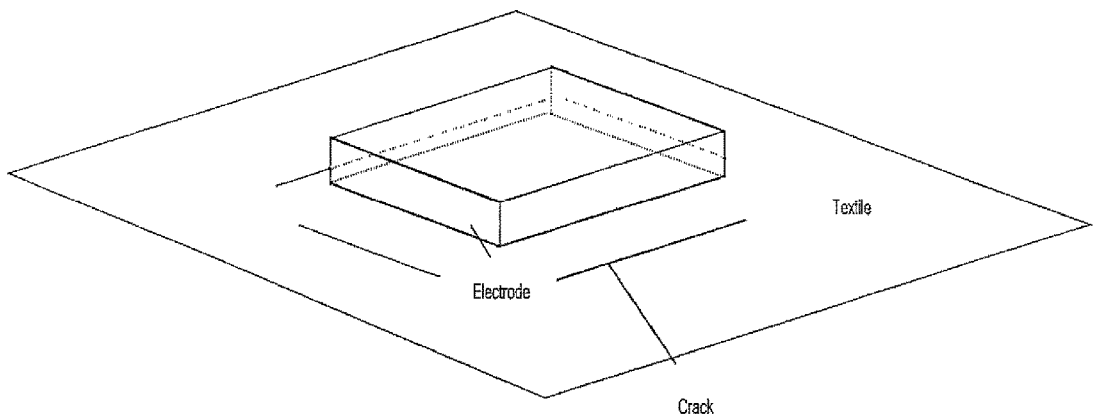
Figure 7:
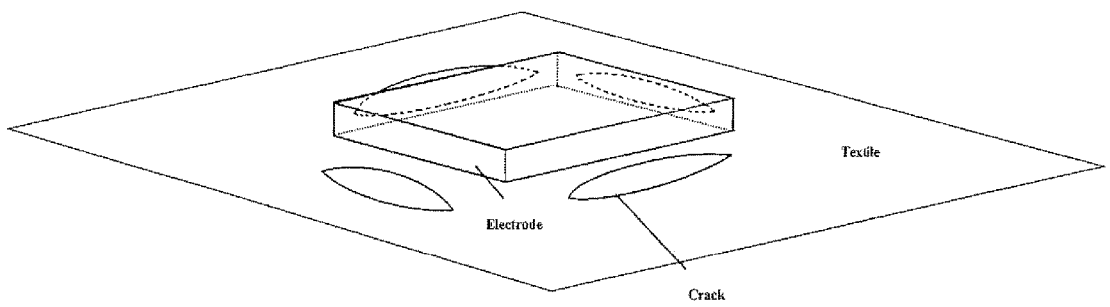
Figure 7:
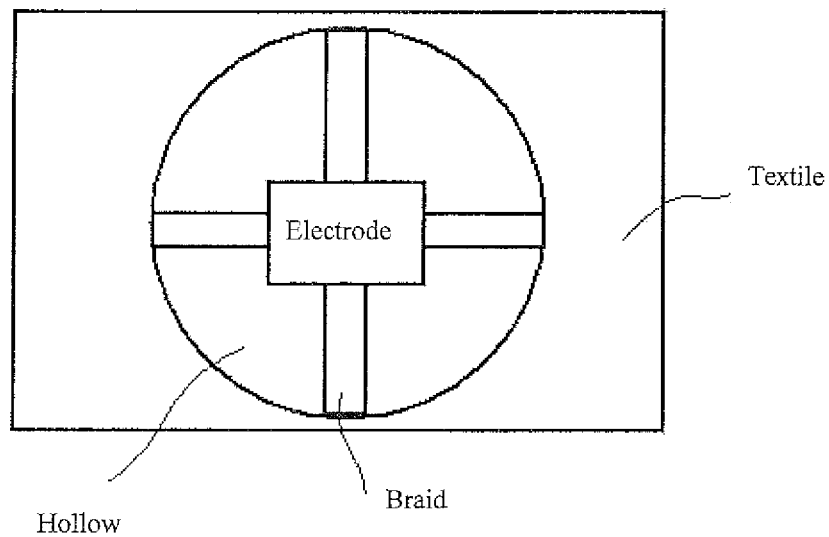
Figure 7:
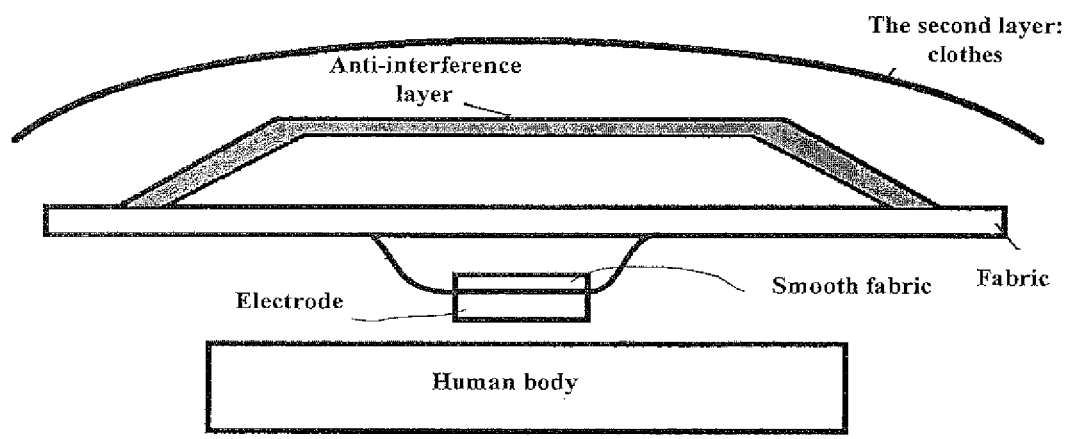
Figure 7:
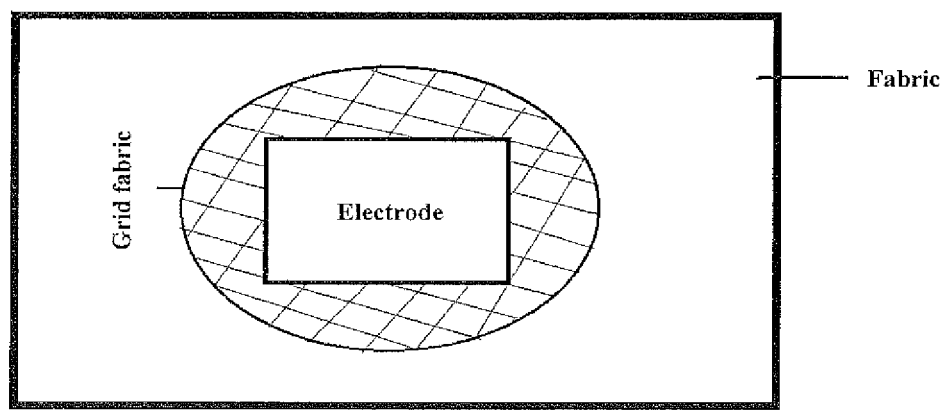

The electrode 40 is fixed on a sliding block of a sliding table instead of the textile; it is as shown in FIG. 7 (a); FIG. 7 (a) is the schematic diagram of the first excellent implementation manner that the electrode is arranged on the sliding table in the invention; or the electrode is fixed on the sliding table; a sliding block is arranged on the textile; it is as shown in FIG. 7 (b); FIG. 7 (b) is the schematic diagram of the second excellent implementation manner that the electrode is arranged on the sliding table in the invention, so that the electrode can slid in two-dimensional or three-dimensional direction of the sliding table by the sliding block; the movable range of the sliding block is L, so that the electrode 40 can follow the human body to reach the effect that the electrode does not move relatively to the skin; and it is a smooth surface between the sliding block and the sliding table.

The sliding block or sliding table can be elastomers capable of being recovered after being pressed or the external force disappears so as to reduce the body movement interference and noise or obtain filtering function, such as rubber, foam materials, sponge, spring, cotton, spandex, lycra, Styrene Butadiene Rubber (SBR), foam-based material, conductive sponge, conductive silica gel, air bag or liquid bag to increase the elasticity.

The electrodes shown in FIG. 7 (a) and FIG. 7 (b) can move on the same plane instead of three-dimensional space; the sliding block and the sliding table are conductors, so another transmission is not arranged on the electrode to send the ECG signals. In FIG. 7 (c), an opening is arranged on the textile 85; and the electrode 40 and the sliding block are respectively arranged above and below the opening to realize the three-dimensional movement. The movable range of the electrode 40 is L which is 0.2-3 cm. At this time, the transmission line is connected with the electrode to send the signals. Or there are conductive materials at the opening of the textile 85, so that the conductive materials of the electrode or the sliding block are communicated to send the signals.

The Seventh Method: Crack or Opening Separating Structure

The electrode is fixed on the textile; the textile around the electrode has crack opening; the textile is made of elastic Lycra cloth, netting fabric or Modal; FIG. 7 (d) is taken as example; the circular electrode with 4 cm of diameter is woven on the textile; 1-3 cm of crack is respectively arranged above or below the textile away 1-3 cm from the electrode or 1-3 cm of crack is respectively arranged at the left and right sides of the electrode; when the body moves, the textile moves; the crack opening of the textile is enlarged, shown in FIG. 7 (e); the effect that the electrode is not easy to move relatively is achieved; and the crack opening is closed or reduced when the body does not move. Certainly, the electrode can be made into the design electrode and textile separating structure, and the electrode is not interfered by the external force.

The more crack of the electrode, the smaller ability of recovering the original form; the factors interfered by the external force must be reduced; and it needs balance. The other method is opening type; there is a 0.2-7 cm of opening space around the electrode; the electrode is connected with the textile by at least one braid; the braid is 0.01-5 cm wide; the narrower the braid, such as one yarn, elastic yarn, stainless steel wire, metallic wire, the less the interaction between the electrode and the textile; it is not interfered by the body action; the wider the braid, the steadier the pressure between the electrode and the human body; the impedance between the electrode and the skin as well as the friction force can be reduced; and it needs to balance. We use 0.5 cm of braid below 2.5 cm of opening to achieve better effect; the braid is elastic or not elastic, shown in FIG. 7 (f); certainly, it has better effect when using separating electrode.

When there is a second clothes outside the textile electrode of the human body, the stability between the electrode and the skin can be interfered by the movement generated by the second clothes of the human body, so FIG. 7 (g) and FIG. 7 (h) adopt anti-external force structures; an anti-interference layer is arranged on the other textile of the electrode in FIG. 7 (g) and composed of smooth and rigid structure, such as buckram, silica gel, leather, sponge and the like; when the external force presses the electrode, it can prevent vibration and have filtering and anti-interference effect; we can adopt smooth materials at the other face that the textile electrode contacts with the human body, such as plastic fabric; the smooth materials contact with the second cloth to reduce the friction force; or a grid fabric can be arranged between the electrode and the textile fabric, the other anti-interference structure shown in FIG. 7 (h); when the second clothes generate interference electrode on the first clothes, the grid fabric has filtering function.

Figure 8:
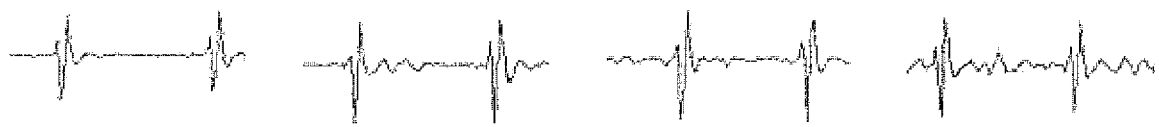
FIG. 8 (a) is the waveform of R wave obtained by the braid as the suspension bar at the side of the electrode when standing still.

In order to verify the effect that the separating electrode restrains the body movement interference, the invention conducts the tests of four postures and actions by the same user pasted with the physiological electrode paste under the left and right oxter (as shown in FIG. 1) in the same day and under the same temperature and humidity; the four postures and actions are standing and still, walking, standing up from the sitting posture and lifting legs from the original position. Meanwhile, the user must wear a coat outside the test underwear so as to obtain R wave. R wave is obtained by the separating electrode in FIG. 4 (d); the obtained results are as shown in FIG. 8 (a), FIG. 8 (b), FIG. 8 (c) and FIG. 8 (d); at this time, the direct current impedance is 0.6M (Ohms) FIG. 8 (a) is the waveform of R wave obtained by the braid as the suspension bar at the side of the electrode when standing still; FIG. 8 (b) is the waveform of R wave obtained by the braid as the suspension bar at the side of the electrode when walking; FIG. 8 (c) is the waveform of R wave obtained by the braid as the suspension bar at the side of the electrode when standing up; FIG. 8 (d) is the waveform of R wave obtained by the braid as the suspension bar at the side of the electrode when lifting legs in situ. The body movement interference of the separating electrode is slightly greater than that of the physiological electrode paste under the left and right oxters by comparing the result of the physiological electrode paste under the left and right oxters with the suspension structure electrodes shown in FIG. 8 (a), FIG. 8 (b), FIG. 8 (c) and FIG. 8 (d) and meets the actual application requirement. The results generated by the electrode of other design in the invention are similar.

The Eighth Method: Double-Layer Separating Structure

Figure 9:
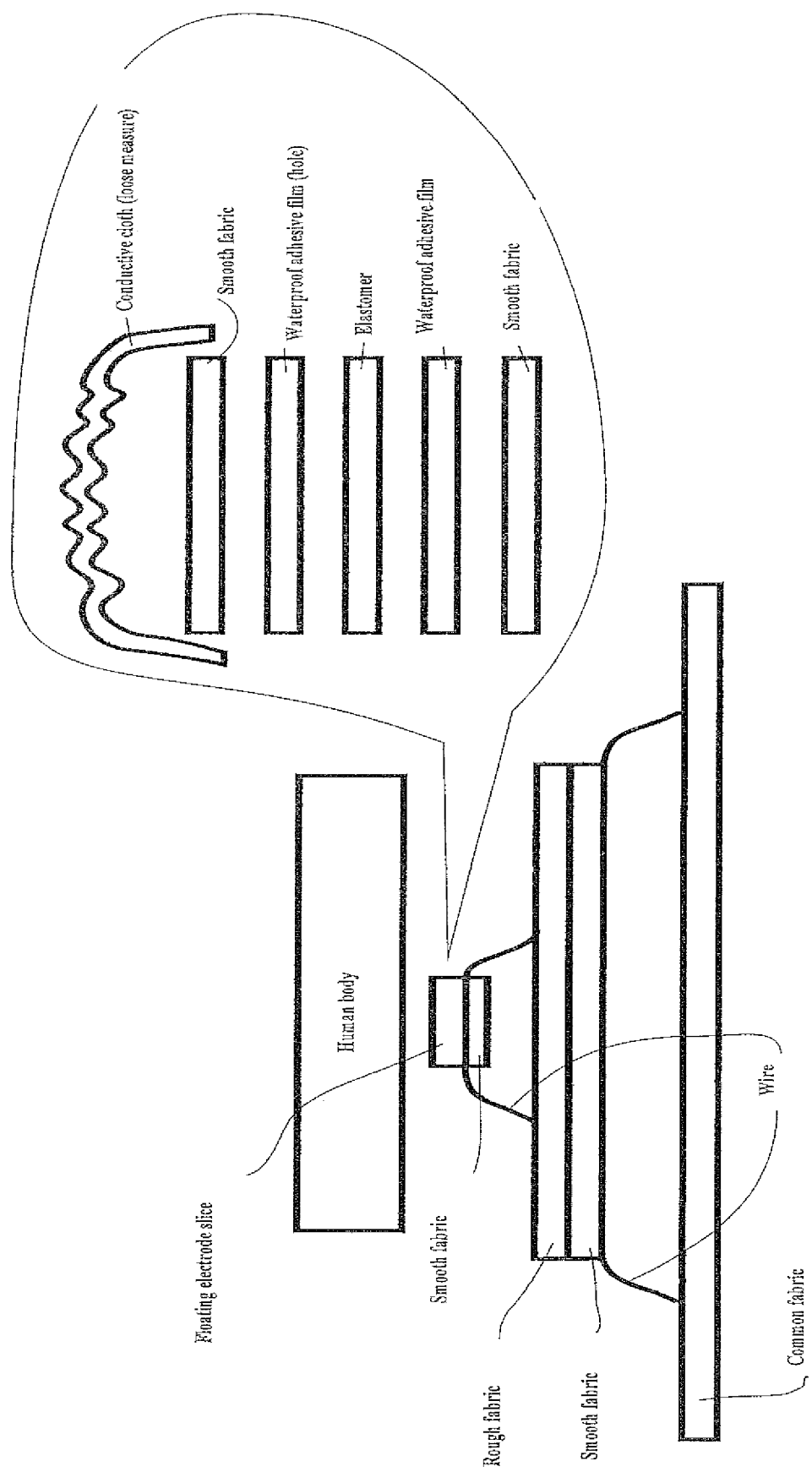
FIG. 9 (a) is the schematic diagram of the first excellent implementation manner that the double-layer separating structure electrodes are combined by the connecting wire in the invention.
Figure 9:
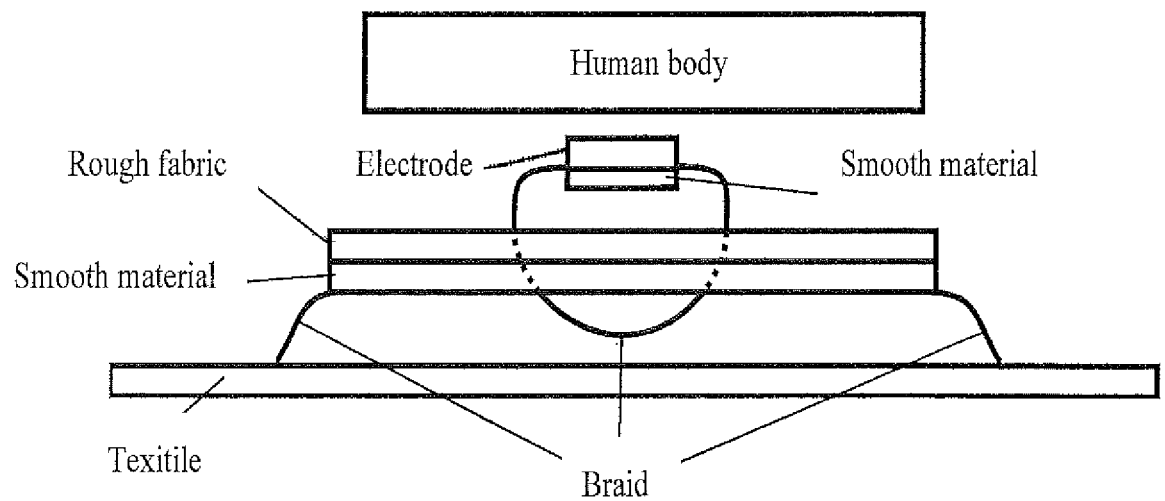
Figure 9:
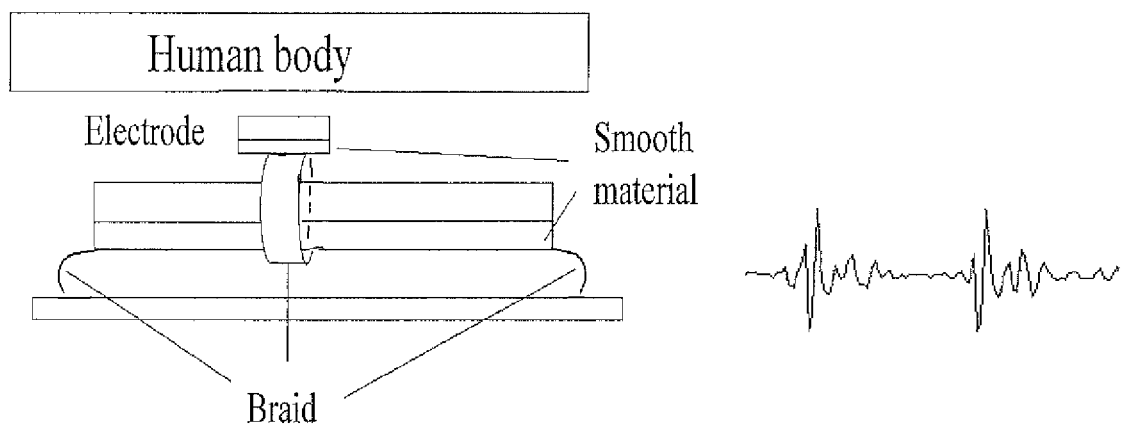

Taking FIG. 9 (a) as example, FIG. 9 (a) is the schematic diagram of the first excellent implementation manner that the double-layer separating structure electrodes are combined by the connecting wire in the invention. The electrode is connected with rough fabric with greater area by the connecting wire; the rough fabric is adhered to the other smooth material; the contacting face of the electrode and the rough fabric is provided with smooth materials with lower friction force so that the electrode can slide relatively to the rough fabric and the electrode does not move relatively to the skin when the body moves. The rough fabric is combined with the textile by the connecting wire; at least one face of the contacting faces of the textile and the rough fabric is the smooth material with low friction force so as to reduce the friction force between the fabric and the textile. When the textile moves relatively to the human body caused by the body movement, the textile can slide relatively to the rough fabric; and the body interference of the electrode is reduced.

When the rough fabric is adhered to the human body and does not slide on the human body, some local movements of the human muscle and the skin are likely to affect the electrode; and the local movements can be released by the separating structure between the electrode 40 and the rough fabric. The double-layer separating structure can restrain body movement interference effectively. Or the connecting wire in FIG. 9 (*a*) can be replaced by the braid; the braid passes through the rough fabric and the smooth materials below the electrode so as to form a ring, as shown in FIG. 9 (*b*); FIG. 9 (*b*) is the schematic diagram of the second excellent implementation manner that the double-layer separating structure electrodes are combined by the braid in the invention. The direction of the braid in the electrode is parallel to the rough fabric. The other way is that the direction of the braid in the electrode is vertical to the rough fabric; a ring is formed outside the rough fabric and as shown in FIG. 9 (*c*); FIG. 9 (*c*) is the schematic diagram of the third excellent implementation manner that the double-layer separating structure electrodes are combined by the braid in the invention; and the effect is as shown in FIG. 9 (*d*); and FIG. 9 (*d*) is the waveform of walking R wave obtained double-layer separating structure electrodes in the invention. The double-layer separating structure can select any two structures in the structures from 1-8 methods; the upper and lower separating structures can be realized by the same or different structures. Moreover, a layer or many layers can be added on the double-layer separating structure to form multi-layer separating structure; the double-layer or multi-layer separating structure can be applied to the capacitive coupling electrode; and the specific content is described in embodiment 3. The materials of the connecting wire in the double-layer separating structure are as shown in the fourth method.

In 1-8 methods, non-slip bar or non-slip fabric can be selectively added on the electrode or the textile so as to reduce the friction force between the electrode and the textile and the relative movement between the electrode and the skin.

The object connecting the electrode with the textile in 1-8 methods, such as connecting wire and suspension bar and the like can be connected by the snap fasteners; the snap fasteners are connected by the any movement in two-dimensional direction and three-dimensional direction or (hook-and-loop) Velcro so as to dismount and replace the electrode shown in table 2. The electrode and the textile around the electrode can be used as the antenna; the connecting wire, suspension bar, snap fasteners or (hook-and-loop) Velcro connecting the separating electrode and the textile can be used as the antenna.

The sponge is used as the elastomer; and the water storage feature of the sponge can help the electrode conduction as shown in FIG. 9 (*a*); the upper and lower faces of the elastomer are provided with waterproof glue films; and smooth fabric is arranged outside the glue films. The smooth fabric and the waterproof glue film are not permeable; holes are needed on the upper-layer smooth fabric and the waterproof glue film so that the sponge can absorb water when being washed; and when the sponge is used, the water is slowly released to the conductive cloth close to human body. When the textile is worn, the sponge is dried and does not contain water; after the textile is worn, the waterproof glue film can prevent the sweat evaporation; the sweat leaves in the conductive cloth and the sponge to help the electrode conduction.

An elastomer is arranged below the conductive cloth of the electrode so as to reduce the body movement interference and the noise or obtain the filtering effect, such as sponge, silicon glue, spring or similar material as shown in FIG. 9 *a*; smooth materials are arranged between the elastomer and the conductive cloth to reduce the friction force of the electrode and the elastomer; meanwhile, the area of the electrode is greater above 0.4 cm$^2$ that the elastomer so that the conductive cloth can move and deform when the skin moves and deforms; for example, the square can be changed to rhombus and not be limited by the elastomer. The elastomer is covered by the smooth materials or the elastomer is separated by the above method instead of directly connecting or adhering to the elastomer.

The surface of each electrode adopted in the invention is the elastic conductive cloth or conductive sheet (silver fiber and stainless steel sheet); and an elastomer containing a conductor is arranged in the electrode so as to increase the conductive ability of the electrode; and when the electrode is washed or damaged when worn, the electrode can keep the sensing ability so as to increase the service life of the electrode.

The conductor on the contacting face of the electrode and the human body can be materials with great friction force, such as wool and non-slip bar; or the friction force can be increased by enlarging the electrode area. The elastomer added in the electrode has shakeproof and filtering functions; elastic and water-absorbing sponge, silica glue or similar material can be selected; or the elastomer can adopt spring or similar material (water swelling rubber, WSR); and water-absorbing water-retaining agent can be added in the elastomer. The water-retaining agent is not insoluble in water, absorbs water which is 100 times of the weight of the water-retaining agent and restrains the water evaporation effectively. The water-retaining agent is divided into two types: the first type is acrylamide-acrylate copolymerization cross-linking agent (polyacrylamide, sodium polyacrylate, potassium polyacrylate, ammonium polyacrylate and the like); the other type is starch grafting acrylate copolymerization cross-linking agent (starch grafting acrylate). The common water-retaining agent is amorphous particles, powder, smalls, sheet and fiber. Or the elastomer is conductive material and electrode; the elastomer can keep water and has shakeproof and filtering functions, so the conductivity can be increased and stabilized. In addition, in order to increase the conductivity, the invention can add an uneasily permeable film layer, semi-permeable film layer or needle non-permeable textile, print non-permeable glue coating, waterproof textile and waterproof strip outside the elastic and in water-absorbing material selectively to prevent moisture adding in the material. Or the elastomer has semi-permeable function so that the moisture leaves in the elastomer and seeps slowly. When the textile is washed, the moisture leaves in the electrode; the fabric of the dried or stoved textile is dried, the moisture in the electrode can still be kept. When the user wears the textile, the body can press the elastomer, so that the liquid stored in the elastomer can release slowly to the electrode and the skin. When the liquid contained in the elastomer is replaced to the air, the interior of the elastomer is in negative pressure after being pressed so as to absorb the skin of human body; meanwhile, the conductive liquid (water) on the skin can be absorbed in the electrode for the sake of conductivity. In addition, the invention adds a conductor between the conductive cloth of the electrode and the elastomer selectively in order to increase the conductivity, such as the conductive woven by the stainless steel fiber. The control box can promote the electrode or the temperature of the around textile by the heating element or heat the electrode or the around textile, so that the human body or the electrode surface temperature rises and the sweat increases to reduce the impedance between the electrode and the human body. There is a heating method; at least one electrode or the around textile has warming or natrium aceticum heating function.

There is also a method for increasing conductivity, namely, add a layer of functional warm clothing in the electrode position and surrounding textile, such as feather warm cloth, so as to improve the skin temperature of the electrode position and increase sweat. In order to enable the product of the invention to be used both in winter or summer, the functional warm cloth can be made into removable type; it will be taken off in hot weather and put on in cold weather, as shown in table 2. The primary results of our experiment shows that the electrode impedance is reduced from 40 M Ohms at the beginning of wearing to 20 M Ohms after 30 min gradually, and then, it maintains stable, and the heartbeat is available. Similarly, the experimental results show that the skin temperature, electrode impedance and ECG signal quality are associated with each other closely. In the invention, a thermistor can be arranged within the electrode to detect the electrode temperature, and then proper strategies are to be adopted, see table 2 for details.

The temperature and humidity of body surface are not exactly the same. The distribution situation of temperature and humidity on body surface can be drawn up by an isothermal line or a constant moisture line, similar to the ECG equipotential diagram. The isothermal line or the constant moisture line of body surface will be changed along the environmental temperature and humidity, and will be different in summer and winter. According to the invention, the interference caused by ECG equipotential diagram, isothermal diagram, constant moisture line, constant moving line, electromyogram or body breathing and movement can be integrated to select better electrode positions, electrode structures or lengths of connection lines. For example, in hot weather, the conductivity of all body skin is good, at this time, only the EGM can be taken into account to determine the electrode position, as shown in FIG. 1(a); in cold weather, the highest chest temperature is at the precordium, the farther away from the precordium, the temperature is lower, at this time, isothermal diagram will be taken into account, the temperature of the position as shown in FIG. 1(a) is lower than the temperature of precordium, it is unfavorable for conductive ECG signal, thus, the electrode can be moved about 2-6 cm to the precordium to obtain better ECG signal, see details in table 2.

Figures 10A, 10B, 10C:
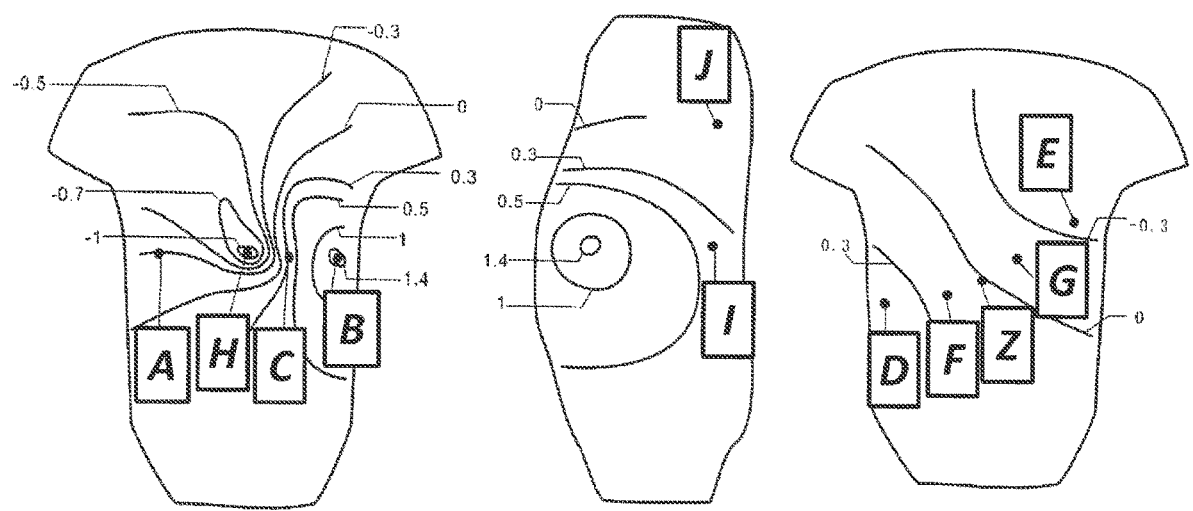
FIG. 10 (a) is the schematic diagram of the equipotential line and electrode position of the front R wave in the invention.
Figures 11A, 11B, 11C, 11D, 11E, 11F:
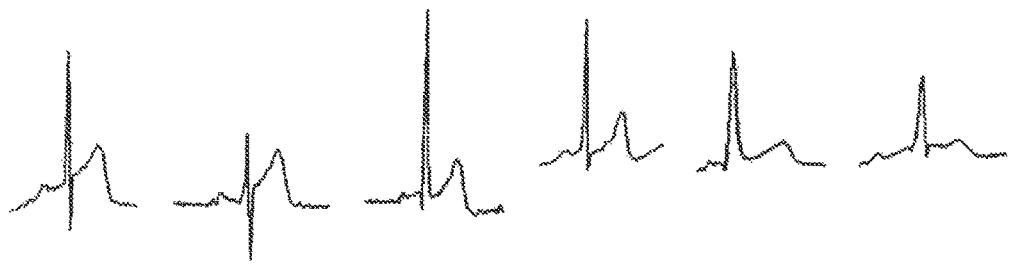
FIG. 11 (a) is the ECG signal drawing detected by electrodes at the A and B parts of FIG. 10 (a) in the invention.

When the electrodes are respectively arranged at A (−0.3 equipotential line) close to front chest of the right axilla as shown in FIG. 10(a) and at B (1.4 equipotential line) close to front chest of the left axilla, the detected electrocardiogram is as shown in FIG. 11(a), where the amplitude of R wave is about 1.8 mV; FIG. 11(b) is the electrocardiogram detected by respectively arranging the electrodes at A and C (between 0.3 and 0.5 equipotential line) of FIG. 10(a), where the amplitude of R wave is about 0.7 mV, this matches with the simulated results in aforementioned literature, it can be determined that the R wave with large amplitude can be obtained by the electrodes at A and B. FIG. 11(c) is the electrocardiogram detected by respectively arranging electrodes at B (1.4 equipotential line) and H (−1.0 equipotential line) of FIG. 10(4), where the amplitude of R wave is maximum, about 2.2 mV, however, the respiratory is easy to be disturbed here, and the equipotential lines here are intensive, the potential changes a lot, the electrodes are easy to shift, even go across the zero equipotential line to reach the positive potential area, in this way, in this way, not only the amplitude is shortened, but the peak direction may be reversed, thereby hard to identify the figure; in addition, this part is further easily blocked by female bra, thus, the electrodes shall be arranged at A and B instead of H (−1.0 equipotential line). As shown in FIG. 10(a), the principal for selecting electrode position in the present invention is that one electrode is arranged at the positive potential area, the other electrode is arranged at the negative potential area, and the zero equipotential line is adopted as the boundary and is not allowed to stridden.

Similarly, if the electrode is arranged at the back of the body, R wave also can be obtained. FIG. 11(d) is the electrocardiogram detected by respectively arranging electrodes at D (0.3 potential line) and E (−0.3 potential line) of the body back of FIG. 10(c), where the amplitude of R wave is about 0.6 mV; FIG. 11(e) is the electrocardiogram detected by respectively arranging electrodes at F (between 0.3 and 0 equipotential lines) and G (between −0.3 and 0 equipotential lines) of FIG. 10(c), where the amplitude of R wave is about 0.45 mV, that's to say, the closer the back electrode is arranged in the internal side, the smaller the amplitude of the obtained R wave is obtained, this matches with the simulated results in aforementioned literature.

Similarly, if the electrodes are arranged at the left and right sides of the body, R wave also can be obtained. FIG. 11(d) is the electrocardiogram detected by respectively arranging electrodes at I (between 0.3 and 0.5 potential lines) and J (zero potential line) of the left body side in FIG. 10(b), where the amplitude of R wave is about 0.4 mV; this matches with the simulated results in aforementioned literature.

Compared with FIG. 11(a) and FIG. 11(f), the sizes of T waves are different, for example, the T waves of 11(a) and 11(b) are bigger than that of 11(c), and T waves of 11(d) and 11(e) are bigger than that of 11(f), and moreover, the proportions between the amplitudes of T waves and R waves are different, because the equipotential line graphs of T waves, R waves, Q waves, S waves and P waves are different.

As the potential of equipotential line of R wave at body back is not high, it is not so intensive as the front chest, the amplitude differences of the obtained R waves from D and E is only 0.15 mV, where the proportions of R waves and T waves are different with that of FIG. 11(a), FIG. 11(b) and FIG. 11(c). If the electrode with larger area is adopted at the back, it should be better to adopt the electrodes extending along the right lower or left lower direction, namely, leave the equipotential line with the center as zero, and turn to higher or lower equipotential line, in this way, bigger amplitude will be obtained.

Similarly, the equipotential lines of P, Q, R, S and T weaves are different; thus, the wave structures of various waves in the electrocardiogram can be used for estimating which electrode can help to obtain the ECG signal.

FIGS. 10(a) to 10(c) can be used for inferring the influence of electrode area size to the ECG signal. As the electrode adopted in the present invention is a plate instead of a little, the output potential thereof shall be the average unit value of the coverage area thereof. In terms of the electrode located at D or E, as the potential lines thereof are relatively sparse, the output potential is still close to the potential at 0.3 or −0.3; in terms of the small area electrode at B (in the 1.4 equipotential line), the output potential can reach 1.4, however, the electrode with larger area located in the same place enables the output potential to be reduced as about 1 mV or lower due to possibly cover the area outside the equipotential line 1. Based on the principle, according to the invention, electrode with large area can be arranged at the area with low intensive equipotential lines, thus, the amplitude is not reduced and the friction of the electrode can be increased.

Figure 12:
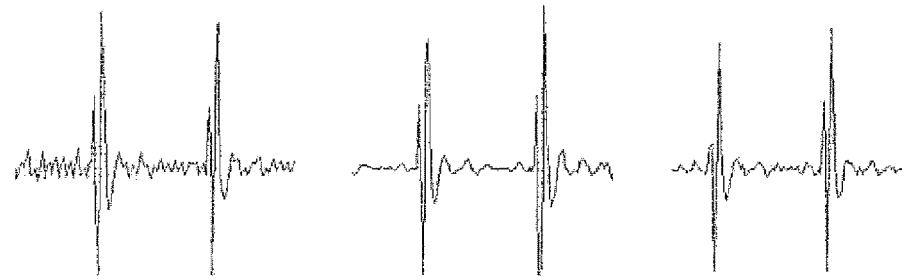
FIG. 12 (a) is the ECG detected by electrode of which the area is 6*3 cm$^2$ in the invention.

As shown in FIGS. 12(a) to 12(c), they are R waves detected by arranging electrodes with different areas at A and B of FIG. 10(a), where the electrode corresponding to FIG. 12(a) is 6*3 cm<2>; the electrode corresponding to FIG. 12(b) is 6*6 cm<2>; and the electrode corresponding to FIG. 12(c) is 6*9 cm<2>. It can be seen that with the increase of electrode area, the amplitude attenuation is not significant. In addition, non-slip bar is arranged on the electrode or the non-slip fabric is arranged in the textile, so that the electrode does not produce obvious shift relative to the textile, by adopting such mode, even when the electrode area is further shortened to 2*2 cm<2>, stable ECG signal can also be read.

There are two good things for enlarging the electrode area: firstly, poor contact is hard to occur, secondly, the friction to skin can be increased thereby reducing body movement interference. The electrode is used for adult size, in terms of child or infant, it can be shortened according to the proportion of commercially available adult and infant electrode.

The feasibility to use bare transmission line or connection terminal by the present invention is further can be discussed according to FIG. 1(a) of the present invention. The transmission line between electrode 40 and control box 50 can also be provided with a lead with an insulation layer or a bare wire without insulation layer, if the insulation layer is failed or adopting bare wire may be subject to two effects, namely, subject to the influences of sweat or rainwater and static electricity. However, the electrostatic interference can be processed by adopting circuits or firmware, thus, the influence thereof is little. When the insulation layer is failed or when the adopted bare wire is in contact with the sweat or rainwater on skin or clothes, an unexpected electrode may be formed, thus, the ECG signal is conducted to the control box 50 to cause unexpected interference. If the unexpected electrode is located in the area with a potential higher than 0.3 or lower than −0.3, the amplitude is at least +/−0.3 mV, which is available for judging R wave; if the unexpected electrode is located in the area with a potential between 0.3 and −0.3, once the insulation layer is failed or bare wire is in contact with sweat or rainwater, the amplitude will be smaller than 0.6 mV, thus, the insulator is arranged in the areas between 0.3 and −0.3 in the present invention, except adopting the transmission line with an insulation layer, impervious textile can be additionally arranged or impervious mortar coating can be printed between body and transmission line, or after using waterproof textile and waterproof stickers to package the bare wire, the bare wire is arranged on the textile, so as to prevent moisture from penetrating.

Similarly, the input terminal on the control box 50 connected with the transmission line further can conduct the ECG signal of the area to the processor in the control box 50 due to sweat or rainwater, thus, the position for the control box 50 shall be preferably avoided the highest or lowest equipotential line areas such as 1.4 or −1, and the best position is the area nearby the zero potential (M point as shown in FIG. 1(a)), in this way, even if one of the input terminals forms into electrode due to sweat or rainwater, at least the ECG signal picked up by the terminal is close to zero, and there is further an input terminal which is not interfered by sweat or rainwater capable of transmitting the ECG signal of the electrode located at 1.4 or −0.3 equipotential lines of FIG. 1 to the processor, and 0.5 mV amplitude further can be obtained. As the equipotential lines are not symmetrically extended from zero, namely, the positive end can reach +1.4 mV, and the negative end is only −1.0 mV, even if the control box is located at W (+0.5 equipotential line) of FIG. 1(a), the input terminal of the control box 50 for receiving the negative end signal may cause the potential as +0.5 due to sweat, but 0.9 mV amplitude can still obtained. It shows that in the present invention, the suitable area for arranging the control box 50 is the area with the R wave equpotential lines from 0 to 0.5.

If the two terminals of the control box 50 are located at the zero equipotential lines close to the precordium, as the equipotential lines here are intensive (namely the potential changes severely), and further due to the extendability of the textile, under sweat wet situation, the terminals of the control box 50 is possibly in contact with the area with quite higher or lower potential instead of zero. Therefore, even if under the sweat wet situation, the processor of the control box 50 can read the R wave with large amplitude. And meanwhile, the length of the transmission line can be shortened if the control box 50 is arranged here.

In addition, in order to reduce the influence of the sweat or rainwater, the two input terminals connected with the control box 50 with the transmission line are respectively arranged at upper and lower two surfaces of the shell of the control box 50, so as to avoid the two terminals simultaneously being stained with rainwater or sweat to lead the ECG signal to become zero potential, and resulting in that the processor in the control box 50 cannot receive signals. In a word, in the two terminals on the control box 50 of the present invention, if one of the terminals is not affected by the moisture to cause two terminals to be on the same potential, obvious R wave can be detected. Similarly, significant signals of P, Q, S and T waves can be obtained by the same design.

By utilizing FIGS. 10(a) to 10(c), the embodiment discloses a method of "complementary electrode set" to reduce the body movement interference, as shown in FIGS. 10(a) to 10(c), electrode is respectively arranged at B, I and Z, and the electrode at B and I are connected together to the positive input terminal of the control box 50, and the electrode at Z is connected with the negative input terminal of the control box 50. The electrode at Z is selected at the middle of a body, and due to the zero equipotential line, the middle of the body suffers minimum interference from left and right arms swing, while locating at the zero equipotential line enables the Z electrode to match with the electrode located at the high equipotential line (such as +1.4 equipotential line at B) and the low equipotential line (such as 0.3 equipotential line at I) to detect R wave. As shown in FIG. 13(a), the amplitude of R wave detected by the electrode at Z and the electrode at independent B is 1.2 mV; as shown in FIG. 13(b), the amplitude of R wave detected by the electrode at Z and the electrode at independent I is 0.3 mV; as shown in FIG. 13(c), the amplitude of R wave detected by the electrode at Z and the electrode parallel at B and I is 0.6 mV; as shown in FIG. 13(d), when the left arm moves forwards, the left side of a coat is extended forwards to cause pressure reduction between the electrode at B and the body, but meanwhile, the pressure between the electrode at I and the body is increased; conversely, when the left arm moves backwards, the left side of the coat is extended backwards to cause pressure increase between the electrode at B and the body, and meanwhile the pressure between the electrode at I and the body is reduced. Thus, the electrode at B and the electrode at I become a pair of complementary electrode, no matter the left hand is in the front or at the back, there will be at least one electrode having enough pressure to pick up R wave on the body. If the amplitude of the R wave is detected by means of FIGS. 13(a) to 13(d), the position of the arm can be predicted, if the amplitude is close to 1.2 mV, it shows that backward moving of arm will cause poor contact of the electrode at I; if the amplitude is close to 0.3 mV, it shows that forward moving of the arm will cause poor contact of the electrode at B; and if the amplitude is close to 0.6 mV, it shows that the middle position of the arm will result in good contact of the electrode at B and I. When the arm moves backwards or forwards, some noise interference is produced, and R wave as shown in FIG. 13(d) will be produced, it is the waveform of R wave detected by the parallel electrode at B and I and the electrode at Z in walking, although there is interference, the R wave can be visible, thus, the complementary electrode can obtain lower body movement interference.

Figure 14:
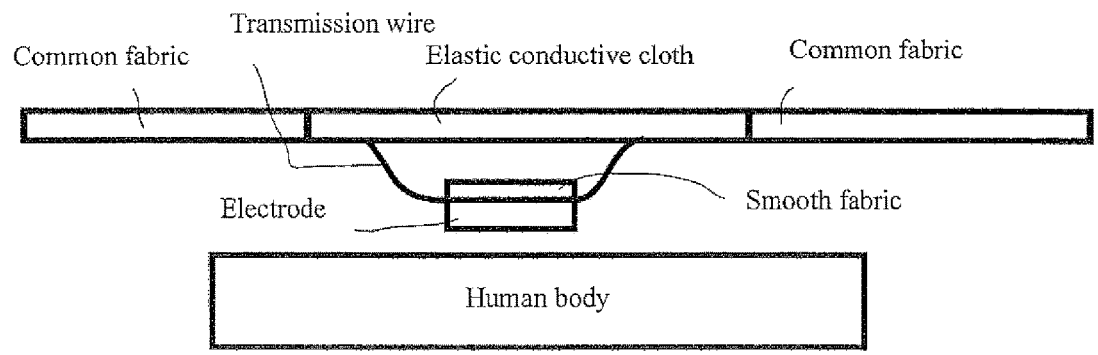
FIG. 14 is the side view that the separating electrode is arranged on the elastic conductive cloth in the invention.

Beside the electrode located at the zero potential is arranged at Z of the back, it also can be arranged at M as shown in FIG. 1(a), the similar effect will be obtained. In addition, the complementary electrode can also be arranged between elastic conductive cloth and a body by adopting separate electrode as shown in FIG. 14. According to the embodiment, large-area elastic conductive cloth is used as the electrode at B, and the separate electrode is used as the electrode at I.

Similarly, two electrodes can be further arranged at the right of the body, one of the electrodes is arranged at −0.7 equipotential line of the front chest, and the other electrode is arranged at the −0.3 equipotential line of the back, in this way, the posture state of the right hand can be obtained.

Similarly, in the present invention, the separate electrode can be introduced, and the separate electrode can be arranged below the elastic conductive cloth and the body, so that the body movement interference can be reduced, and at this time, the elastic conductive cloth can so also be used as the electrode, as shown in FIG. 14.

When the user wears short-sleeve or long-sleeve daily clothes, an electrode is respectively arranged at the front and rear two sides of left and right armpits, and the two electrodes at each side are in parallel connection with the processor of the control box. When the arm uplifts forwards, the sleeves will tract the armpit cloth to move forwards, so that the electrode arranged at the rear side of the armpit is close to the body, while the electrode arranged at the front side of the armpit is far away from the body. Similarly, when the arm moves backwards, the electrode arranged at the rear side of the armpit is far away from the body, while the electrode arranged at the front side of the armpit is close to the body. Different gestures of the arm will result in different positions of the electrode for capturing the ECG signal, and the shapes of the ECG signal are different, as shown in FIGS. 15(a) to 15(d). Where, FIG. 15(a) is the electrocardiogram obtained when the right arm is at the rear side and the left arm is at the front side; FIG. 15(b) is the electrocardiogram obtained when the both arms are at the front side; FIG. 15(c) is the electrocardiogram obtained when the both arms are at the rear side; and FIG. 15(d) is the electrocardiogram obtained when the right arm is at the front side and the left arm is at the rear side.

Figure 15:
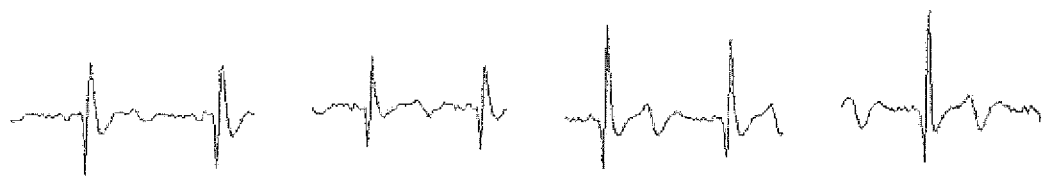
FIG. 15 (a) is the ECG obtained when the right arm is rear and the left area is front.

Compared with FIG. 15(a) and FIG. 15(d), it shows that relative to R wave, the Q wave of FIG. 15 (a) is larger, while the Q wave of FIG. 15(d) is smaller; the T wave of FIG. 15(a) is smaller, while the T wave of FIG. 15(d) is larger.

Compared with FIG. 15(c) and FIG. 15(d), it shows that relative to R wave, the Q wave of FIG. 15(d) is smaller, while the Q wave of FIG. 15(c) is larger.

Compared with FIG. 15(b) and FIG. 15(d), the T wave of FIG. 15(b) is smaller, while the T wave of FIG. 15(d) is larger.

Above is only used for giving examples, actually, the posture of a body can be identified by the proportions of R, Q, R, S and T waves of electrocardiograms obtained through the electrode with different areas or located in different positions, such as the electrode located at sleeve opening, chest, rear arm and the like.

Compared with the followed second embodiment, in this embodiment, the posture is obtained by analyzing the waveform under the condition that the ECG signal is clear and recognizable, while in the second embodiment, the movement thereof is obtained through analyzing the noise, they are complementary to each other.

When the electrode is tightly close to the body, the impedance between the electrode and the body is low, and the ECG signal with lower noise can be obtained. According to the ECG signal obtained in different positions, the proportions of Q, R, S and T waves are different. The two principles can also be used for judging the sleeping posture of the wearer. In the embodiment, two electrodes are respectively arranged at the front chest, back, left side and right side. When the wearer lies on his/her back, the electrode arranged at the back is pressed by the body to produce good conductivity; although the rest electrode is in contact with the body, the conductivity is not good, thus, the electrocardiogram waveform is not affected lot. Similarly, when the wearer lies in other sleeping gestures, the different electrode sets will provide ECG signal. Comparing the electrocardiograms, the sleeping gestures of the wearer can be predicated. According to the embodiment, R wave can be read in daytime body movement, and complete electrocardiogram can be read when the body is still at night.

The invention aims to enable users to feel comfortable and convenient in use, the adopted electrode is dry electrode made of textile instead of physiological electrode patches commonly used in hospitals. As the impedance between the dry electrode and the body is large and unstable, the ECG signal with good quality cannot be obtained under certain environments (such as low temperature and low humidity), for example, the impedance is easily interfered by body movement, or when the body is still, there is still electromagnetic interference caused by power supply. Therefore, the embodiment puts forward corresponding countermeasures targeted on this topic, so that the present invention can meet the practical requirement better.

Figure 16:
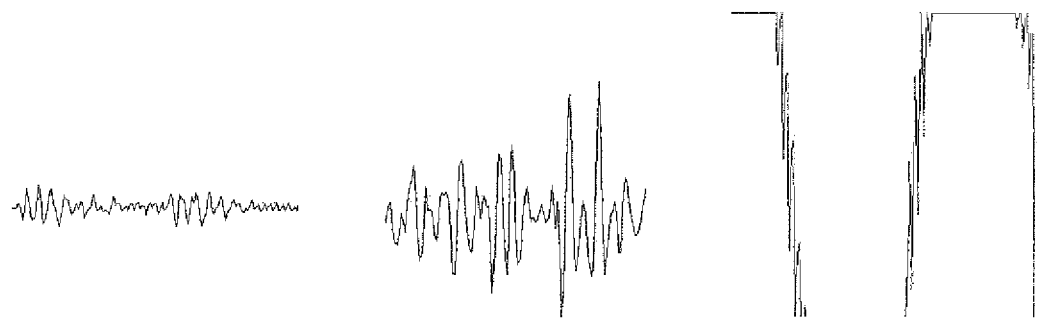
FIG. 16 (a) is the waveform of R wave obtained in static when the electrode impedance is 15M Ohms.

When a user only wears above daily clothes under low temperature and low humidity (16° C. of temperature and 55% of humidity) environment, the waveform is detected by dry electrode made of textile, and meanwhile, the direct current impedance between two electrodes is detected (see detailed method in 8th method of the 6th embodiment), FIG. 16(a) is the waveform diagram of R wave obtained when the electrode impedance is 15M Ohms and when the body is still; and FIG. 16(h) is the waveform diagram of R wave obtained when the electrode impedance is 30M Ohms and when the body is still. At this moment, the impedance between the skin and the electrode is too high, the ECG signal is hard to be conducted, the power coupling enters electromagnetic interference of the processor, relatively, the electromagnetic interference is bigger than the ECG signal, so the R wave cannot be recognized; even if the electrode is pressed forcibly, it still cannot be improved. If one electrode is removed from the body, the impedance is larger, and the noise waveform floats to the upper saturated area or the lower saturated area as shown in FIG. 16(c). Comparing FIG. 16(a), FIG. 16(b) and FIG. 16(c), it shows that the higher the impedance, the bigger the noise is.

Figure 17:
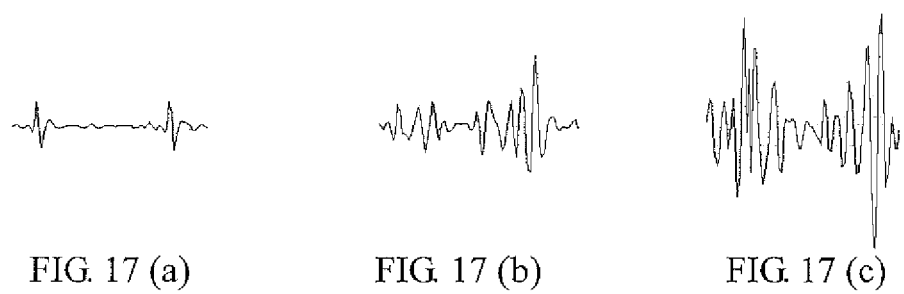
FIG. 17 (a) is the waveform of R wave obtained in static when the electrode impedance is 10M Ohms.
Figure 17:
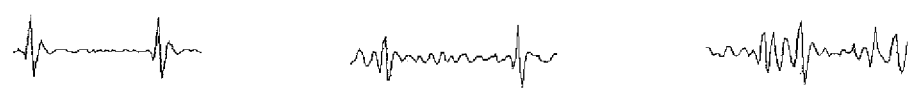

When the direct current impedance is reduced to 10M Ohms, R wave can be picked up at the static state, as shown in FIG. 17(a), however, it is hard to recognize the R waves of body movement interference such as walking and leg lifting in the original place, as shown in FIG. 17(b) and FIG. 17(c). When the direct current impedance is reduced to 0.8M Ohms, the R wave can be picked up in static and walking states, as shown in FIG. 17(d) and FIG. 17(e), however, the body movement interference such as leg lifting in the original place is still large, thus it is hard to recognize the R wave, as shown in FIG. 17(f). When the direct current impedance is reduced to 0.6M Ohms, R wave can be recognized in various movements such as leg lifting in the original place, as shown in FIGS. 8(a) to 8(d). From FIGS. 8(a) to 8(d); 16(a) to 16(c) and 17(a) to 17(f), it shows that the rules are as follows: the lower the direct current impedance is, the lower the noise is; the larger the body movement interference, the higher the direct current impedance is; if the noise is large when the body is still, the noise is larger when the body moves. The aforementioned rules are vice versa. Referring to the rules, when the machine is turned on, the electrode impedance can be continuously detected for a period of time (such as 10 seconds), and meanwhile, the movement state of the user can be predicated by the change of the electrode impedance (see detailed method in following material), thus, the ECG signal can be read in what movement situation of the user can be estimated. If the impedance is low enough, the capturing of ECG signal begins; if the impedance is too high, the processor in the control box will adopt a proper countermeasure, so that the whole system is optimized, and then the capturing of ECG signal begins. For example, when the direct current impedance is detected as 10M Ohms, the R wave can be read when the body is still, however, the R wave cannot be read when the body is in the movement state. If the current impedance is too high to meet the requirement of the user, for example, the requirement is to recognize the R wave in walking; the countermeasure disclosed by the embodiment is as follows.

The primary experimental result shows that when the electrode impedance is less than 1M Ohms, the heartbeat can be detected by the control box as shown in FIG. 1(a), and moreover, the interference caused by body movement is relatively low, even if the separate electrode structure is not adopted, the R wave in walking can be read, and at this time, the capacitance value between the two electrode is about more than 10 nF. When the electrode impedance is between 1M and 2M Ohms, the R wave in walking can be detected by adopting the separate electrode structure, and the capacitance value between the two electrodes is about more than 5 nF. When the electrode impedance is more tan 2 M Ohms, only the noise is easily to be detected by the control box as shown in FIG. 1(a), while the noise size is in positive correlation with the movement; if the electrode impedance is between 2 M and 20 M Ohms (at this time, the capacitance value between two electrodes is about 0.5 to 5 nF), generally speaking, only starting the negative feedback circuit can reduce the noise to recognize the static heartbeat, and the position of the electrode connected by the negative feedback circuit can be selected by the equipotential line graph as show in FIG. 1(a), as long as in the area where the potential electrode is more than 0.4 lower than the higher potential electrode and higher than the lower potential electrode, namely the potential is in the area from 0.1 to 1.0, the noise can be effectively inhibited and the ECG signal is not reduced significantly; if the electrode impedance is between 20 M and 30 M Ohms (at this time, the capacitance value between the two electrodes is about 0.33 to 0.5 nF), generally speaking, only starting the positive electrode circuit (arranging the preamplifier circuit close to the electrode) can reduce the noise to recognize the heartbeat in still state, and if the electrode impedance is between 30 M and 40 M Ohms (at this time, the capacitance value between the two electrodes is between 0.25 to 0.33 nF), the negative feedback circuit and the positive electrode circuit must be started to sufficiently reduce the noise thereby recognizing the heartbeat in sill state. If the detected impedance is more than 40 M Ohms (at this time, the capacitance value between the two electrodes is about less than 0.25 nF), the processor guide the user to tighten the clothes ribbons, add clothes, add functional warm cloth, replace the electrode position or add conductive liquid on the electrode through the communication equipment, and when the impedance is less than 40 M Ohms, the detection of heartbeat can be started, otherwise the heartbeat cannot be detected, and only the noise can be detected, thus, the power supply is waste, however, the movement state of body can be detected based on the noise. If the electrode impedance is reduced less than 40 M Ohms, while the noise is still large and the heartbeat is hard to be detected, the control box can start the aforementioned circuit which is not activated, or start the capacitance coupling electrode circuit (see details in the third embodiment) and firmware or software inhibiting body movement and power interference to detect the heartbeat. These circuit can be in off or hibernation state when the electrode impedance is very low so as to reduce power consumption. Based on the result, in the embodiment, the electrode impedance will be firstly detected when the machine is turned on, and different circuit will be started, as shown in table 2.

TABLE 2

Countermeasures adopted by the processor under various electrode impedances in power-on

| Electrode impedance (unit of resistance: M Ohms, unit of capacitance: nF) | Activated circuit, firmware, software or guide users |
|---|---|
| The resistance is less than 1; the capacitance is more than 10 | The control box as shown in FIG. 1 is able to not adopt the separate electrode structure to realize comfort. |
| The resistance is less than 2; the capacitance is more than 5 | The control box as shown in FIG. 1 must adopt the separate electrode structure. |
| The resistance is between 2 to 20; the capacitance is between 0.5 to 5 | Firstly start the negative feedback circuit, if the heartbeat is hard to be detected, start the positive electrode circuit, capacitance coupling electrode circuit, heat or humidify the electrode, or the firmware or software inhibiting body movement and power inference. |

TABLE 2-continued

Countermeasures adopted by the processor under
various electrode impedances in power-on

| | |
|---|---|
| The resistance is between 20 to 30; the capacitance is between 0.5 to 0.3 | Start the positive electrode circuit, if it is still hard to detect the heartbeat, start the negative feedback circuit, the capacitance coupling electrode circuit, heat or humidify the electrode, or the firmware or software inhibiting body movement and power interference. |
| The resistance is between 30 to 40; the capacitance is between 0.33 and 0.25 | Start the negative feedback circuit and the positive electrode circuit, if it is still hard to detect the heartbeat, start the capacitance coupling electrode circuit, heat or humidify the electrode, or the firmware or software inhibiting body movement and power interference. |
| The resistance is more than 40M; the capacitance is less than 0.25 | Guide the user to tighten the clothes ribbons, add clothes, add functional warm cloth, replace the electrode position or add conductive liquid on the electrode. |

The resistance value is only used for the explained examples, in large-scale application, the resistance value shall be adjusted according to the actual environment. The embodiment will memory the resistance values under various situations in a database as the basis of judgment.

Similarly, the method also can be applied in EEG, EMG, TENS or electrodes used in electric shock.

According to the temperature, resistance and capacitance of the electrode listed in table 2, when the electrode is stable and close to the body, the value is stable, otherwise, the value changes severely, maybe the electrode is not tightly close to the body or it is caused by severe movement of the user, and this time, the ECG signal cannot be obtained. Thus, the temperature, resistance and capacitance of the electrode can be used as the indexes for obtaining the ECG signal, particularly, the sampling rate can be lower and easily be recognized, this is not like the ECG signal which is complex in sampling rate and hard to be recognized. The temperature, resistance and capacitance of the electrode can be used for the processor to put forward proper countermeasures, and further can be sent to the monitor center at the remote end through the communication equipment, so that the proper circuit, firmware, software or guidance are activated by the remote end.

If the listed countermeasures are adopted, and the electrode impedance cannot be reduced to obtain the ECG signal with lower noise, the processor can output a special code instead of outputting the noise unable to recognize the heart-type wave, so as to reduce power consumption.

Similarly, the countermeasure is can be implemented in a reverse way. When the electrode impedance is reduced below a certain threshold (such as 2 M Ohms) and maintains a period of time (such as 30 seconds), small noise can be obtained if the body is still, and the processor can select a band-pass filter (0.1-40 Hz) with wide frequency band to capture the complete ECG, and the processor further can suggest the user to loose the clothes ribbon slightly to get a comfort state. If the electrode impedance is between 2 and 20 M Ohms, the processor can select the band-pass filter (10-30 Hz) with narrow frequency band to capture the R wave and meanwhile reduce the interference, or detect the heart rate through Hilbert-Huang transform. Thus, the present invention can optimize power-conservation, comfort and signal quality based on the actual situations. This method is also suitable for EEG, EMG, TENS or electrodes used in electric shock.

In this embodiment, the first method in the sixth embodiment is adopted to simultaneously measure the capacitance value among the texture electrodes, if the capacitance value is not still low (such as 10 Nf) and the resistance value is very high (such as 10 M Ohms), the electrodes are still on the bodies and not easily conductive due to the too dry skin. If the capacitance value is very low and the resistance value is very high, it is very likely that the electrodes are dropped or the transmission lines appear faults, at the moment, the users shall detect or exclude the faults in the invention through the communication equipment.

Said electrode impedance shall be quickly changed along the body movement, for example, for the users, during the still, the resistance value of the electrode is 2.3 M Ohms while the capacitance value thereof is 5.2 nF; during walking, the resistance value is 5.7 M Ohms while the capacitance value is 2.6 nF; during running, the resistance value is 9.3 M Ohms while the capacitance value is 1.2 nF. This is because the electrode is not tightly contacted with the body under the body movement, the resistance value is risen and the capacitance value is declined, the electrode impedance cannot be quickly changed under other changing factors (such as ambient temperature and relative humidity, and sweat caused by non-sports factors). Based on the characteristic, we may estimate the human motion state in accordance with the change of the electrode impedance, namely, the larger variation amplitude is and the stronger movement is. In the same way, the moving disturbance on used textures, smooth materials or inhibition bodies of non-slip bars in the invention can be speculated in comparison with the difference of the impedance under still and movement. The larger difference between them is and the lower moving disturbance of the inhibition body is. For the purpose of increasing the accuracy of the human movement speculated by the electrode impedance, the processor shall selectively read signals from the accelerometer, the gyroscope, the camera or other sensors capable of sensing the human movement to confirm the human movement.

For the condition that the noise wave model is shifted to upper and lower saturation areas, in the embodiment, the capacitor in the filter circuit is in parallel connected with an electronic switch (composed of field effect transistors), controlled by the microcontroller and connected to the ground wire of the circuit. When the signals don't reach to the saturation regions, the electronic switch is turned off and the filter circuit is normally operated. When the signals reach to the saturation regions, the electronic switch is turned on by the microcontroller, so that the charge of the capacitor is leaked to the ground and the signals are quickly returned from the saturation regions to the center, in this way the transient response time of the filter circuit can be shortened and the R wave shall be also identified with more time.

For acquiring ECG signals under poor contact of electrodes or transmission lines, except for two electrodes in FIG. 1(a), an electrode is provided for the embodiment, the ECG signals can be acquired by optionally selecting two of said three electrodes. The third electrode is arranged around the zero equipotential line to own the better effect. As shown in FIG. 10 (a), one electrode is located at B (1.4 equipotential line) while the other electrode is located at the −0.3 equipotential line, they both can acquire a lead ECG signal whose amplitude is 1.7 mV; if one more electrode is located at the zero equipotential line, three lead ECG signals can be acquired, the amplitudes thereof are respectively 1.7 mV, 1.4 mV and 0.3 mV; even if the electrode at the 1.4 equipotential line is damaged, the amplitude of the unique acquired ECG signal is 0.3 mV, and the R wave still can be obviously identified. Whereas, if the third additional electrode is located at the −0.3 equipotential line and the electrode at the 1.4 equipotential line is damaged, the amplitude of the unique acquired ECG signal is 0 mV, and the R wave cannot be identified. Considering that the equipotential line is not zero symmetric extension, the third electrode is arranged between 0 to +0.5 equipotential lines, for example, when the third electrode is located at the +0.5 equipotential line, the ECG signals with 1.7 mV, 0.9 mV and 0.8 mV amplitude can be acquired; if the second electrode is located at the −1.0 equipotential line, the effect is better.

In the embodiment, left and right arms, and the left leg of the day clothes are respectively provided with an electrode, not only Lead I, Lead II and Lead III limb lead is generated, but also the reference potential for measuring chest lead is generated. One or more electrodes with the 2*2 cm area value are arranged between −1 to +1.4 equipotential lines, namely V1 to V6 chest lead. The texture is very likely to move towards the areas due to elasticity, the processor shall acquire the ECG signals from V1 to V6. The reference potential can be acquired by the way that the connector is connected with the clothes, the trousers, the hat and the glove except for the limb lead.

The Second Embodiment

Estimate the Human Movement by the Noise

In the body movement, it's hard to avoid the relative displacement between the electrodes and the skin, the body ions shall be also moved, this moment, the ECG signals will contain quite a number of noise due to disturbance. On the contrary, the noise is as the index of the body movement. In the embodiment, five methods for estimating the situations of the human movement are proposed.

The First Method: Estimate the Human Movement by Times Misjudging Noise as the R Wave In the embodiment, when the human movement is estimated through noise analysis, much noise is misjudged as the R wave if being restrained by the filter firmware. Because the interval time of the noise is far lower than that of the normal heartbeat, under the normal condition, the heartbeat within one minute is impossible from 72 times under the general activity (the R wave interval is 0.833 seconds) to 200 times under the extreme strenuous movement (the R wave interval is 0.3 seconds), the noise can be easily identified by the microcontroller in the control box, and the identifying rules are shown below: take the most-time heart rate within one minute, set the interval of the R wave thereof as one, take a part (such as ½ or ⅔) of the R wave interval less than one as noise. The times of the noise interval in the statistical chart is accumulated as the pointer of the noise amplitude, namely the movement amount amplitude.

In sleeping, the body is less likely to move, but the noise may be formed under turning or involuntary movement of hands and feet. The movement amount within a certain time (for example seven-hour sleeping) is formed into a statistical chart, thereby obtaining the sleep activity chart and knowing about the sleep quality of the user. Thereinto, the noise time accumulation is ad the sleep activity chart of the activity index, the horizontal axis is time while the longitudinal axis is noise time accumulation as the activity amount. The noise magnitude can be represented by the noise amplitude on the horizontal axis of the electrocardiogram, the larger amplitude is and the larger movement is.

Similarly, the day's activities can be formed into a day's activity chart. If the noise is regular, for example, every 0.5 seconds much noise is generated once for three minutes, it is concluded that the user performs the regular movement, such as walking; if much noise is occasionally generated, it may be caused of anxiety; or a lot of electromyographic signals shall disturb the electrocardiogram based on strained wearers. Thus, the day's activity chart can be applied to the home care old, and the caretakers can hereby judge the behavior of the old for real-time intervention.

The Second Method: Estimate the Movement of Human Body by Peak Amplitude

The signal cannot reach saturated state under small body movement interference; the microcontroller can identify R wave and obtain noise; and the noise amplitude can change irregularly. The normal R wave amplitude is steady, not big or small and has rule. By the feature, the processor can record the maximum value (amplitude of the peak) in each small period; the time is taken as the horizontal axis and the amplitude is taken as the vertical axis to draw a figure; and the figure can show the degree of body movement interference. When there is no body movement interference, the figure presents a straight line; and the stronger the body movement is, the bigger of the line fluctuates.

The Third Method: Estimate the Movement of Human Body by Time Scale of Upper and Lower Saturation When the body movement is fierce, the ECG signal is easy to shift to the upper saturation area or the lower saturation area. The signals reaching to the saturation area cannot read R wave; and the time scale reaching to the saturation area can stand for the degree of the movement interference. In a certain time, the longer of the time reaches to the saturation area, the fiercer of the movement interference is.

The Fourth Method: Estimate the Movement of Human Body by the Linear Range

Figure 13:
FIG. 13 (a) is the waveform of R wave detected at Z and B parts of FIG. 10 (c) and FIG. 10 (a).

FIG. 13 (d) shows the signals in the movement; the firmware can adjust the gain value automatically and enlarge the linear range so that the whole signal is unsaturated in the linear range. Comparatively speaking, if the user is in the static state, the signal cannot change shapely; at this time, the firmware can adjust the gain value automatically and shrink the linear range so as to obtain excellent resolution ratio; and it is the existing well-known Auto Gain Control. The degree of the body movement can be estimated by the gain value or change of the linear range, namely, the gain value (linear range) shows the slow body movement; conversely, it is fierce.

The Fifth Method: Estimate the Movement of Human Body by Normal R Wave in Unit Time It is known from FIG. 17 (a), FIG. 17 (b), FIG. 17 (c), FIG. 17 (d), FIG. 17 (e) and FIG. 17 (f) as well as the fourth method that R wave cannot be read when signal shifts to the upper saturation area or the lower saturation area because of the body movement interference. Conversely, R wave presents steadily in the reasonable time under the normal condition; in the embodiment, the normal R wave in unit time is taken as the indicator; the lower R wave shows fierce body movement.

When the electrode is not adhered to the body, the signal can shift so as to occur the noise under the similar movement interference. The embodiment can add posture sensors, such as an accelerometer, a gyroscope, a magnetometer or an inclinometer and the like in the control box or on the textile selectively; and the measured accelerated speed and the like are used as the indicator of the action or noise.

The Third Embodiment

Capacitive Coupling Electrode

Not like the physiological electrode used in hospital, the above electrode does not comprise gel containing water and potassium chloride to increase the conductivity, so it is called as dry electrode.

Under the condition that the temperature and humidity is low or the user has dry skin, the conductivity between the dry electrode and the skin is low, which does not help to pick up ECG signals; and capacitive character is left only. Capacitive coupling electrode or circuit can be used under the condition, namely, there is no DC conductivity between the electrode and the skin; and the ECG signals are delivered by the capacitive coupling. As far as physiological monitoring clothes, it must bear the washing force; the insulation layer on the capacitive coupling electrode can be damaged when washed; and it is not the perfect capacitance and has conductivity. In a word, practical application condition must be considered; and the physiological monitoring clothes have the dry electrode and the capacitive coupling electrode at the same time to adapt to the environment variation.

The insulation layer of the capacitive coupling electrode is dielectric substance, which selects the materials with higher relative dielectric constant and lower perveance, such as nylon (nylon, the relative dielectric constant is 3.2), silicon dioxide (the relative dielectric constant is 3.9), polyvinyl chloride (PVC, the relative dielectric constant is 3), copper calcium titanate (CCTO, the relative dielectric constant is 10,000) and the like. The whole dielectric substance can be adhered to the textile apart from being adhered to the conductor. For example, the dielectric substance is mixed with the solvent or the adhesive; and then cotton yarn is soaked in the mixture so that the cotton yarn is adhered to the dielectric substance and woven into the cloth; or the cotton yarn is twisted into yarn with other fiber and woven into cloth, namely, it is made into the textile with high dielectric coefficient; and the textile is used as the insulation layer of the capacitive coupling electrode. The other example is that the cotton yarn in the above example is replaced by the conductive fiber to be woven into cloth, namely, a capacitive coupling electrode; when the capacitive coupling electrode is connected with other conductors, the dielectric substance can be removed by physical or chemical method; and the conductive fiber can be exposed and connected with other conductors.

The conductor and dry electrode of capacitive coupling electrode can be arranged on the textile by different methods; for example:

1. The conductor and the dry electrode can be woven from the non-conductive fiber and conductive fiber by a textile process; the textile process is knitting, weaving, tatting, embroidering or other suitable processes.

2. The conductor and the dry electrode can be woven by embedding, bonding or sewing the conductive metal sheet into the textile.

3. The conductor and the dry electrode can be woven by sewing the conductive filaments in the textile.

4. The conductor and the dry electrode can be woven by coating or covering conductive substance on the textile.

5. The conductor and the dry electrode can be woven by adhering or sewing the conductive textile on the textile.

6. The conductor and the dry electrode can be woven by conductive silica gel or rubber. Or the electrode is formed in such a manner that the conductive fabric is fixed on the fabric by pasting, weaving or (hook-and-loop) Velcro and the like; in addition, the electrode can be the conductive parts used for clothing, such as button, sequin, bead and the like. The electrode can contain the high-density materials, such as metal or glass, so that the electrode is vertical to the earth's core.

The non-conductive fiber includes but not limited to cotton, linen, nylon, etc., but the conductive fiber includes but not limited to multimolecular conductive fiber or conductive metal fiber, or it is formed by blending the stainless steel fiber with the non-conductive fiber, or formed by coating or permeating the conductive material on the in the insulation fiber, wherein the conductive material accounts for 1% to 100% of the conductive area.

The simultaneous use method of the dry electrode and the capacitive coupling electrode which are installed on the textile of the embodiment comprises the following steps of:

1. Inserting the conductor 75 into the elastomer 90 arranged below the conductive fabric, wherein the conductor 75 is the capacitive coupling electrode as shown in FIG. 18(a), FIG. 18(a) is the schematic diagram of the first simultaneous use form of the two electrodes.

2. Coating an insulation layer on the conductor 75, arranging between the textile 85 and the body, and locating beside the dry electrode 40 as shown in FIG. 18(b), wherein FIG. 18(b) is the schematic diagram of the second simultaneous use form of the two electrodes.

3. Inserting the conductor 75 into the textile 85, and locating the conductor 75 on the lateral surface of the dry electrode 40 as shown in FIG. 18(c), wherein FIG. 18(c) is the schematic diagram of the third simultaneous use form of the two electrodes.

4. Arranging the conductor 75 on the outer surface of the textile 85, and locating beside the dry electrode 40 as shown in FIG. 18(d), wherein FIG. 18(d) is the schematic diagram of the fourth simultaneous use form of the two electrodes.

5. Coating an insulation layer on the conductor 75, arranging between the textile 85 and the body, and locating above the dry electrode 40 as shown in FIG. 18(e), wherein FIG. 18(e) is the schematic diagram of the fifth simultaneous use form of the two electrodes.

6. Inserting the conductor 75 into the textile 85, and locating above the dry electrode 40 as shown in FIG. 18(f), wherein FIG. 18(f) is the schematic diagram of the sixth simultaneous use form of the two electrodes.

7. Arranging the conductor 75 on the outer surface of the textile 85, and locating above the dry electrode 40 as shown in FIG. 18(g), wherein FIG. 18(g) is the schematic diagram of the seventh simultaneous use form of the two electrodes.

Figure 18:
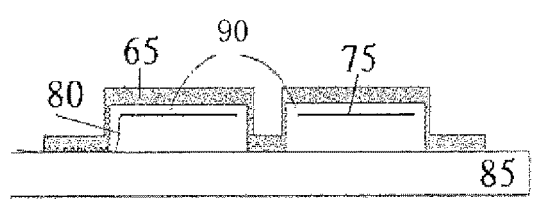
FIG. 18 (a) is the schematic diagram of the first manner for using the two electrodes at the same time in the invention.
Figure 18:
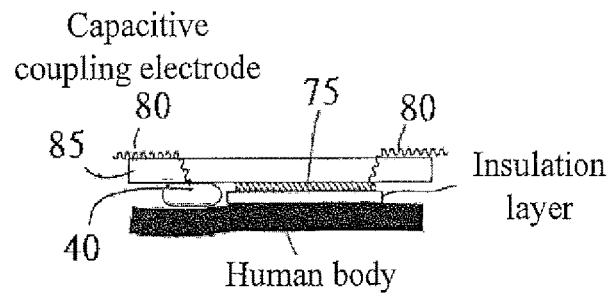
Figure 18:
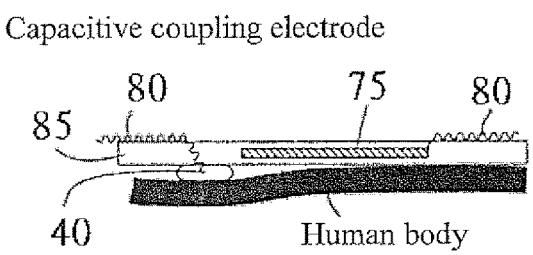
Figure 18:
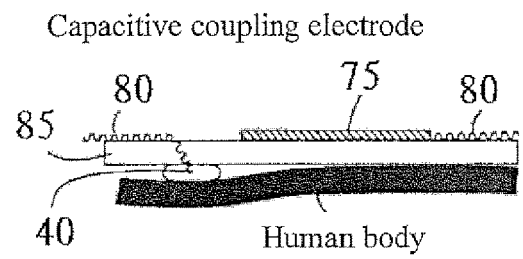
Figure 18:
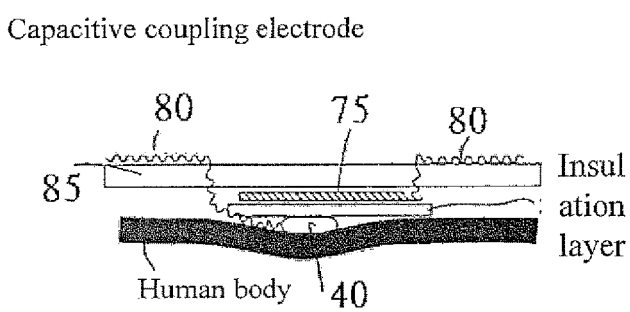
Figure 18:
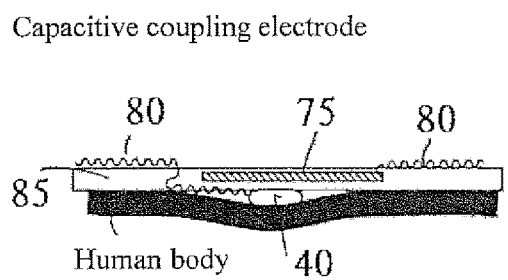
Figure 18:
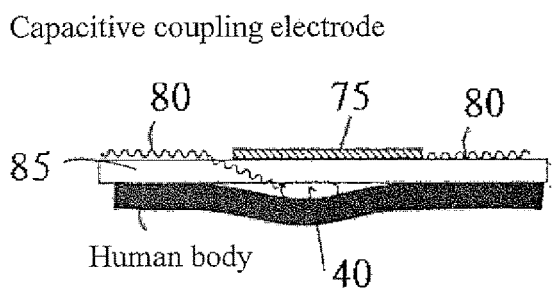
Figure 18:
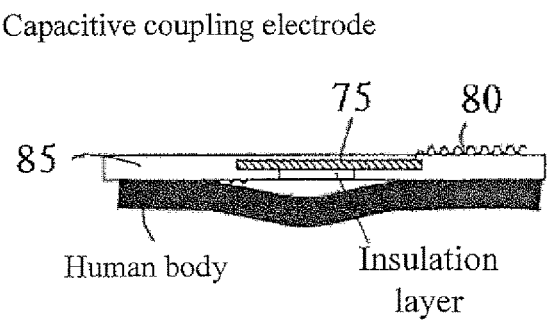
Figure 18:
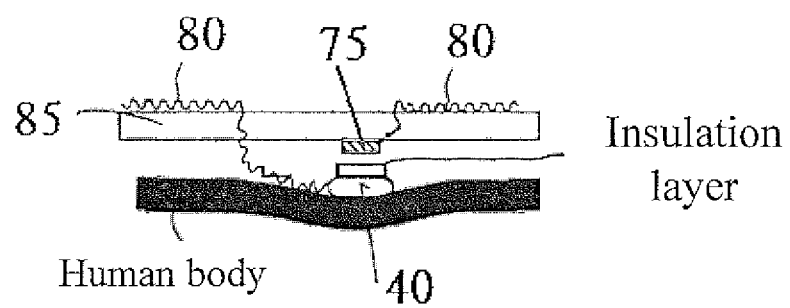

8. Adopting the conductor 75 as the electrode to be arranged in the textile 85, so that the conductor 75 not only can be adopted as the dry electrode, but also can be adopted as the capacitive coupling electrode; when the skin is dry, the resistance is large, the microcontroller in the control box can switch to use the circuit of the capacitive coupling electrode and capture the ECG signal, and when the skin is wet, the resistance is small, the control box can switch to use the circuit of the dry electrode and capture the ECG signal (as shown in FIG. 19, the negative feedback electrode is selectively used according to the size of the noise, an insulation layer is selectively arranged below the electrode to be adopted as the dielectric substance so as to increase its capacitive character as shown in FIG. 18(*h*), and FIG. 18(*h*) is the schematic diagram of the eighth simultaneous use form of the two electrodes in the invention);

9. Arranging the elastic conductor 75 on the inner surface of the textile 85, and locating above the dry electrode 40, wherein the dielectric substance of another insulation layer is coated on the dry electrode 40 as shown in FIG. 18(*i*), but the dry electrode 40 is connected and adhered to the textile 85 through the elastic belt (not shown in FIG. 18(*i*), and FIG. 18(*i*) is schematic diagram of the ninth simultaneous use form of the two electrodes in the invention);

In order to reduce the external interference, the capacitive coupling electrode is possibly close to the electrode along the position set by the preamplifier circuit, namely the active electrode.

Figure 19:
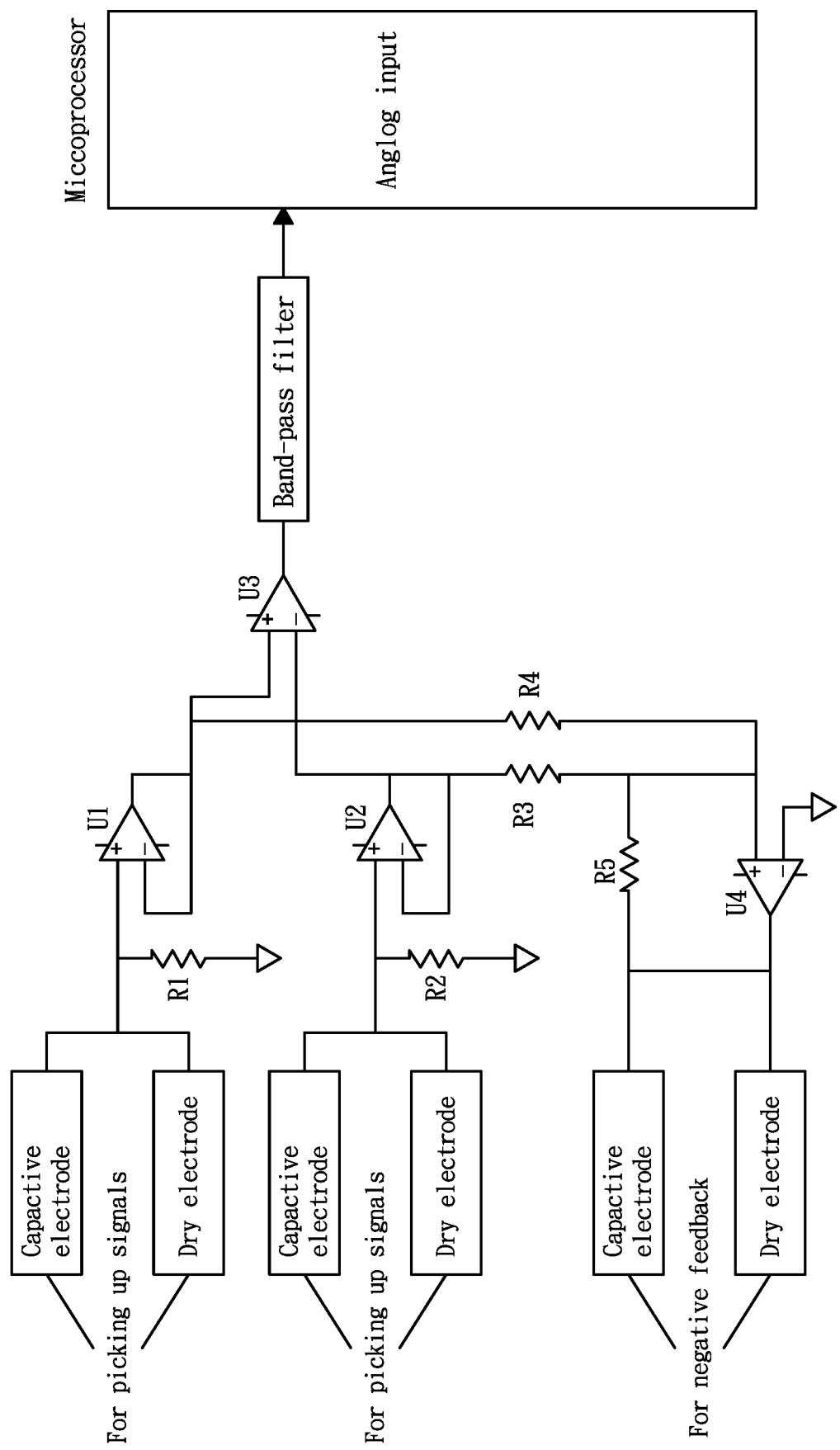
FIG. 19 is the schematic diagram that the capacitive coupling electrode and the dry electrode share a circuit.

In the other specific embodiment, the dry electrode and the capacitive coupling electrode share the same transmission line as shown in FIG. 19, and FIG. 19 is the schematic diagram that the capacitive coupling electrode and the dry electrode share a circuit. When the skin is wet and the conductive character is good, the ECG signal is transmitted to the amplifier through the dry electrode, or transmitted through the capacitive coupling electrode.

For the capacitive coupling active electrode, because the signal is small, the external electromagnetic interference must be prevented through a good shielding and guarding skill. In the invention, in order to be matched with the textile, the shielding and guarding can be realized trough the conductive fabric (such as the sliver fabric or the steel fabric) or the copper foil originally used in the ordinary circuits, the conductive coating film and so on, or the active electrode is used on the textile, or replaced with other conductive fabric or conductive materials to achieve the shielding and guarding purposes.

Embodiment 4

Increase of Air Bag and Liquid Bag in External Part or Inner Part of Electrode

Figure 20:
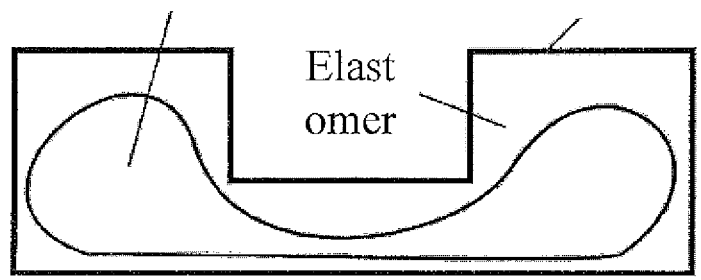
FIG. 20 is the side view of the electrode containing air bag or liquid bag in the invention.

The air bag or the liquid bag can be arranged below the conductive fabric as shown in FIG. 20, the air bag or the liquid bag (containing fluid, such as air, water, oil, etc.) is arranged in the inner part of the electrode; when the body is compressed at one side, the fluid in the air bag or the liquid bag flows to the other side so that the conductive fabric at the other side is closer to the body to improve the conductivity. Elastomers, such as sponge, silica gel, and springs and so on, can be selectively arranged in the air bag or the liquid bag, preferably the hydrophilic material is better, and has buffer action.

Figure 21:
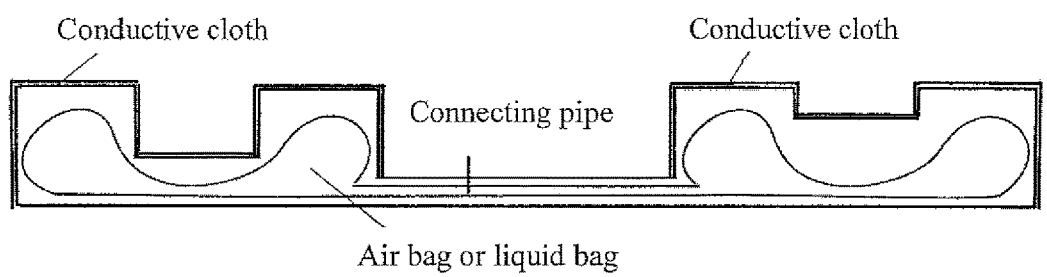
FIG. 21 (a) is the side view that the two electrodes comprise air bags or liquid bags and are connected and auxiliary to each other.
Figure 21:
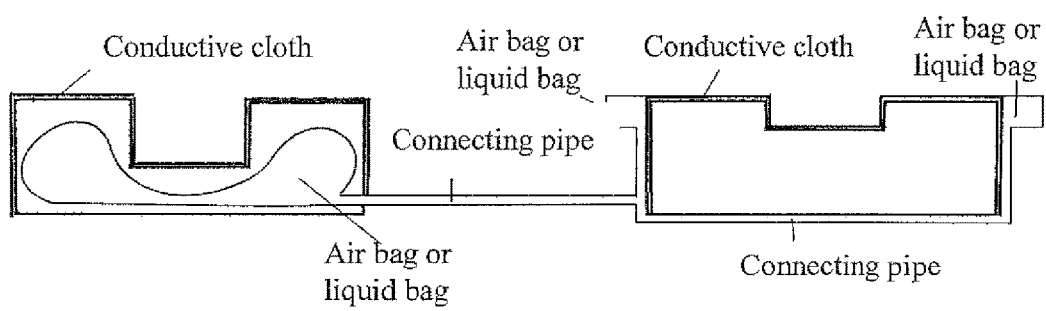

The air bag or the liquid bag can be applied to the electrodes arranged on the different positions, for example, if one electrode is arranged on the right axilla, and the other electrode is arranged at the right loin. Ideally, when person sleeps on the right side, the right axilla and the right loin will be compressed by the body, but because the curve of the body or the concave and convex shapes of the beds, one of the electrodes may be completely compressed, and the contact situations of the other one are not good, if one group of the air bags or the liquid bags (two) at this time there are connected with each other through the connecting pipe as shown in FIG. 21(*a*), when one electrode is compressed, the electrode at the other side is closer to the body, and the conductivity is improved.

One group of the air bags or the liquid bags which are connected with the connecting pipe can be used for preventing the other electrode from contacting the body, for example, in the embodiment 1, the sleeping postures are judged through the waveform of the ECG signal, ideally, when person sleeps on right side, only the right axilla and the right loin are compressed by the body, but the electrode in the prothorax will be occasionally compressed by hands, which mistakenly touches the body. In the embodiment, the air bag or the liquid bag can be arranged on the right axilla or in the prothorax, and the two bags can be connected through the connecting pipe, but the air bag or the liquid bag is not located between the conductive fabric and the clothes, but located around the conductive fabric in a ring shape as shown in FIG. 21(*b*), so that the centre can be exposed outside to contact the conductive fabric with the body. When person sleeps on the right side, the air bag or the liquid bag on the right axilla will be compressed, so that the air bag or the liquid bag in the prothorax swells, and the body cannot be easily and mistakenly touched by compression of the hands.

The electrode is the dry electrode, but the capacitive coupling electrode is also applied to touching the body as well. Or a small sheet or zonal material with high relative dielectric constant is arranged on the electrode, such as nylon (the relative dielectric constant of the Nylon is 3.2), silica dioxide (the relative dielectric constant is 3.9), polyvinyl chloride (the relative dielectric constant is 3), copper calcium titanate (the relative dielectric constant of CCTO is 10000) and so on as shown in the embodiment 3, to increase the capacitance.

The liquid bags containing water adopt the elastic structure which can be unfolded when not compressed and lightly leaky, namely non completely sealed, so that water can be absorbed when washing, trace water can be leaked on the electrode when used and compressed to increase the conductivity. If the liquid bag is provided with the elastomers, the water in the liquid bag can be prevented from leaking quickly. When the liquid bag contains the air, because of the elasticity of the liquid bag, negative pressure is formed inside the liquid bag after compressed to absorb the skin of the body, at the same time, the conductive liquid on the skin (such as water) can be absorbed on the electrode to conduct.

In the invention, the microcontroller can control a pump to drive the air, oil or water, the pump is connected to the air bag or the liquid bag which is fixed between the electrode and the textile through a sealed pipe. When the signal is small because of any electrode impedance is too high, the microcontroller can open the pump so that the air bag or the liquid bag swells, and the electrode can be close to the skin via the compression of the air bag or the liquid bag. When the liquid bag swells by using oil or water, an oil or water storage groove can be arranged in the control box.

Embodiment 5

Figure 22:
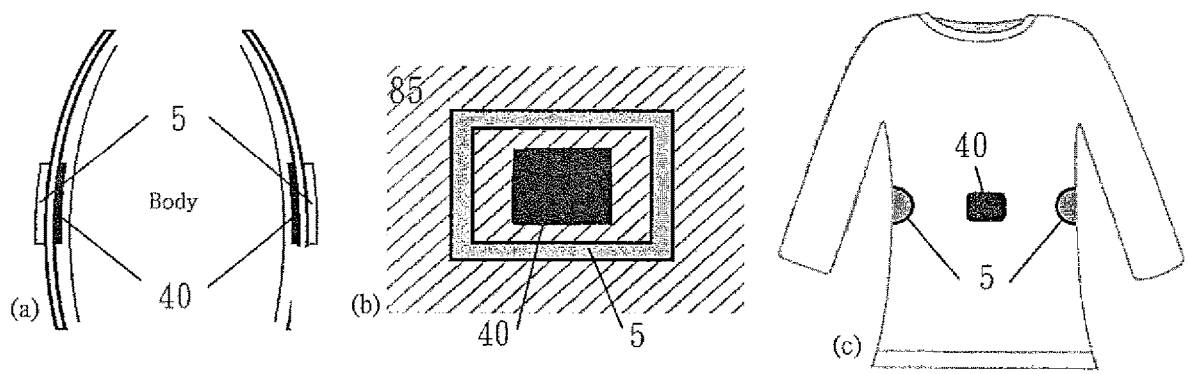
FIG. 22 (a) is the schematic diagram that the textile and the electrode are respectively provided with a magnet.

Reduction of Body Movement Interference by a Manner of Fixing Electrode with Magnetic Force The first method in the embodiment comprises the following steps of: arranging the permanent magnetic material 5 outside or beside the electrode, such as Al—Ni—Co (AlNiCo), ferrite (Ferrite), samarium cobalt (SmCo) and neodymium iron boron (NdFeB); arranging the magnetic conductive material such as silica steel or the permanent magnetic material 5 of which polarity is different from the former permanent magnetic material at the corresponding side of the body; using the principle of heteropolar attraction, which is to produce the absorbing force for the electrode 40 so that the force that the electrode is adhered to the body is stronger to reduce the body movement interference as shown in FIG. 22(*a*), wherein FIG. 22(*a*) is the schematic diagram that the textile and the electrode are respectively provided with a magnet; similarly, arranging the magnetic conductive material 5 outside or beside the electrode, or arranging the permanent magnetic material at the corresponding side of the body, wherein the effects are the same. In addition, the electrode is the permanent magnetic material 5 or the magnetic conductive material, such that the stainless steel and the silica steel are magnetic and conductive, so that the permanent magnetic material or the magnetic conductive material can be adopted as the electrode; AlNiCo, SmCo and NdFeB are conductive, so they can be adopted as the electrode 40; the permanent magnetic material 5 or the magnetic conductive material (Ferrite) can be threaded, or arranged in the hollow fiber, or combined with other materials and then threaded, or coated on the ordinary yarns by a manner of dyeing or electrically plating, or combined with the electric conductor (such as sliver fiber) by a manner of entwisting or blending to form the conductive fabric which is not only conductive but also magnetic.

The second method in the embodiment comprises the following steps of: using the principle of poles repel to drive the electrode 40 into the body, for example, the permanent magnetic material 5 is arranged outside the electrode on the oxter, and then arranged on the inner side of the upper arm at the same time, so that the same poles of the two permanent magnetic materials are opposite and then repel each other, the electrode 40 on the oxter is driven into the body, and the body movement interference is reduced; similarly, arranging the permanent magnetic material 5 on the objects (such as beds, chairs, etc.) close to the body, the same poles are opposite to drive the electrode 40 into the body; similarly, arranging the permanent magnetic material 5 on the outerwear or the brassiere, and arranging the electrode and the permanent magnetic material 5 on the underwear; arranging the permanent magnetic material 5 on the pants and the shoes; arranging the electrode and the permanent magnetic material 5 on the stockings, and driving the electrode into the body through the repulsive force produced because same poles repel.

For example, in FIG. 22(*a*), the electrode 40 and the textile 85 are respectively provided with the permanent magnetic material of which the poles repel, and then the electrode 40 can be driven into the body; similarly, in FIGS. 4(*a*) to 4(*d*), the separated electrode 40 and the textile 85 are respectively provided with the permanent magnetic material 5 of which the poles repel, and then the electrode 40 can be driven into the body; similarly, in FIG. 21(*b*), the air bag or the liquid bag and the conductive fabric are respectively provided with the permanent magnetic material 5 of which the poles repel, and then the electrode 40 can be driven into the body.

In addition, the sliding block and the textile shown in FIG. 7(*a*) can be selectively provided with the permanent magnetic material 5 of which the poles repel, and then the electrode 40 can be driven into the body; or the sliding block and the textile shown in FIG. 7(*b*) can be selectively provided with the permanent magnetic material 5 of which the poles repel, and then the electrode 40 can be driven into the body; or the sliding block and the textile shown in FIG. 7(*c*) can be selectively provided with the permanent magnetic material 5 of which the poles repel, and then the electrode 40 can be driven into the body.

The embodiment can adopt the annular permanent magnetic material 5 to increase the stability of the mutual exclusive magnetic force as shown in FIG. 22(*b*), and FIG. 22(*b*) is the schematic diagram adopting annular permanent magnetic substance. The electrode 40 can be located in the annular shape and is not easy to move outside because of the mutual exclusive force around the annular permanent magnetic material 5 and the electrode 40.

The permanent magnetic material 5 can be arranged at the two sides of the electrode 40 to adhere the electrode to the body through the absorption magnetic force as shown in FIG. 22(*c*), and FIG. 22(*c*) is the schematic diagram that the permanent magnetic substance is arranged at the two sides of the electrode on the clothes. The permanent magnetic material 5 which is located at the two waists gets the magnetic conductive material or the permanent magnetic material 5 arranged below or around the electrode 40 closer to the chest so that the electrode can be close to the body. The electrode 40 also can be closer to the body through the magnetic conductive material or the permanent magnetic material 5 arranged below or around the electrode 40 which is arranged on the shoulder or the permanent magnetic material 5 arranged at the lower front and back sides of the shoulder.

The permanent magnetic material 5 can be a complete solid body and also can be formed with multiple small blocks, the south pole is connected with the north pole, and the permanent magnetic material 5 can be curved after assembled along the outline changes of the body, so that the effect of the magnetic force is better, and user can more comfortably use it.

Embodiment 6

Detection of Poor Contact of Electrode

Figure 23:
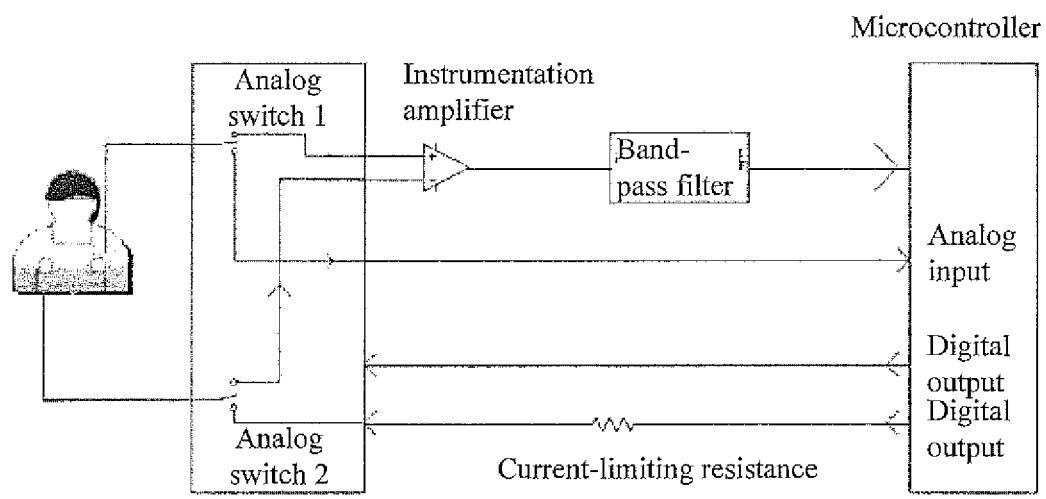
FIG. 23 is the schematic diagram that the pulse wave detects whether the electrode is in good contact or not.
Figure 24:
FIG. 24 (a) is the waveform of R wave obtained when the surface capacitance is 2.7 nF.

When the electrode and the skin are poorly contacted (high impedance) or the transmission line is broken off, R wave is difficult to see. So the invention provides eight methods for detecting whether the electrode is poorly contacted with the skin:

The first method which is only used in fields containing two electrodes as shown in FIG. 23, and FIG. 23 is the schematic diagram that the pulse wave detects whether the electrode is in good contact or not. The method comprises the following steps of: producing a pulse wave by the microcomputer or the oscillator (such as LM555); selectively connecting to the electrode after passing through the current-limiting resistor and the analog switch, wherein the analog switch 1 and the analog switch 2 are controlled by digital output; detecting whether the electrode is poorly contacted by a manner of connecting the electrode with the pulse wave or connecting to the instrument amplifier so as to obtain the ECG signal, wherein when the analog switch 1 and the analog switch 2 select the method of connecting the electrode with the pulse wave, the electrode is connected to the analog input end of the microcomputer, then the impedance between the two electrodes can be obtained by measuring the amplitude or the frequency or the effective cycle of the electrode; the method is similar to the method for measuring the capacitor by using the multimeter, which is to detect the impedance between the electrode and the skin of the body, but the conductive method of the skin of the body is based on the capacitance, so that the value obtained by using this method is the capacitance value, the method for measuring the capacitor by using the multimeter can be adopted, and the result refers to Table 2; if the impedance is larger than some critical value, the contact is poor. FIGS. 24(a) to 24(b) show the electrocardiograms of the same group of the electrodes obtained by a same user under different capacitance, wherein the capacitance value in FIG. 24(a) is 2.7 nF and the pulse frequency produced by the oscillator is 16.8 K Hz; the capacitance value in FIG. 24(b) is 21.7 nF and the pulse frequency produced by the oscillator is 2.1 K Hz; the former noise is larger than the latter after comparing 24(a) with 24(b), and the vibration frequency is greatly larger than the latter. In the invention, 5 nF is set as the critical value; when the capacitance value is smaller than 5 nF, various measures shall be taken as shown in Table 2.

For the situation of more than two electrodes, to detect whether each electrode is poorly contacted, the electrode which is encircled on the body, the arms or the thighs can be arranged on the textile to ensure that the electrode is not poorly contacted because of body movements, the pulse wave can be conveyed inside by the electrode and then read by other electrodes to detect the whether each electrode is poorly contacted. The method refers to the PCT International patent case PCT/CN2010/001931 provided by the applicant, wherein the method elaborates that when pressure, pull force, torsion or tension exists between the body and the electrode, the impedance between the skin of the body and the electrode changes, especially the capacitance changes, then one circuit sends the signal, and the impedance changes are shown in forms of changes of frequency, voltage or current. The method not only can be used for judging whether the electrode is poorly contacted, but also can be used for reading the respiration and postures or analyzing the gaits, for example, the electrode is directly contacted with the body, when person lies down, the pulse frequency produced by the oscillator is 170 kHz, when person stands, the pulse frequency is 120 kHz, and when person sits down, the pulse frequency is 80 kHz, because the gravity direction and the postures change the chest circumference and the abdominal circumference, and then the pulse frequency is changed. At this time, the pulse frequency is changed while breathing, if the respiration can be detected, the electrode is perfectly contacted with the body, and relevant circuits can be activated to measure the ECG signal. Similarly, the method can be used for the capacitive coupling electrode, and the electrode does not be contacted with the body, because the circuit sends the pulse wave not the direct current, therefore the capacitance value of the electrode can be measured. Meanwhile, the electrode is separated from the clothes but not directly contacted with the clothes.

Figure 25:
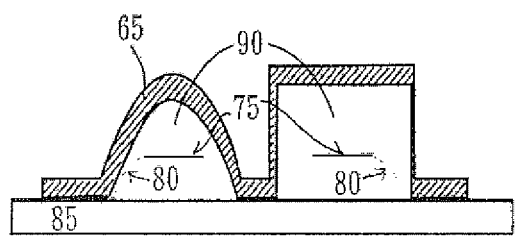
FIG. 25 (a) is the schematic diagram that the two electrodes in the invention are electrically connected in different shapes.
Figure 25:
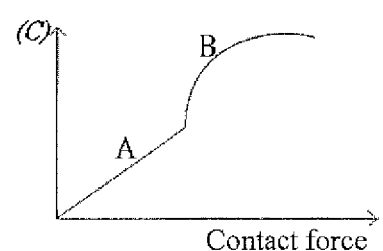

The method can be applied by matching with the electrodes of which the shapes, sizes and materials are different as shown in FIG. 25(a). FIG. 25(a) is the schematic diagram that the two electrodes in the invention are electrically connected in different shapes.

Figure 26:
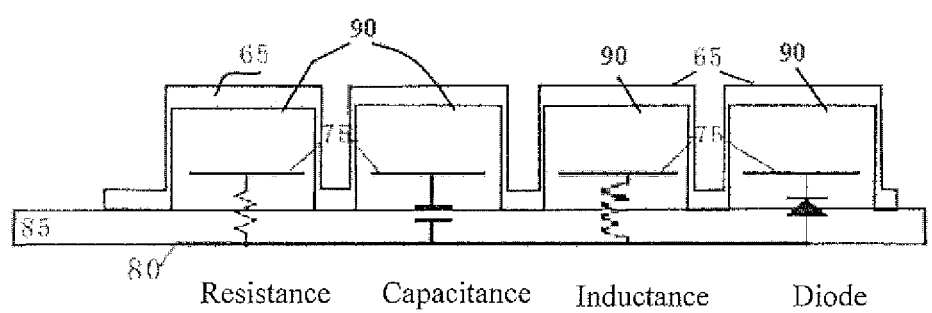
FIG. 26 is the schematic diagram of four electrodes connecting with different electronic components in the invention.

The method can be further applied by matching with the extra electronic components of the electrode as shown in FIG. 26. FIG. 26 is the schematic diagram of four electrodes connecting with different electronic components in the invention. The two electrodes which are electrically connected but serially connected or parallelly connected have different reaction when receiving the pulse input, the waveforms, the phases, the impedance and the resonant frequency of the electrodes are changed, for example, for the electrodes connected to the capacitors, their waveforms are in forms of exponential function when charging or discharging, not the primary pulse wave. The microcomputer can distinguish those changes, so that which electrode is contacted with the body can be inferred, therefore the electrode which is contacted with the body can be used for receiving the ECG signal. Further, the postures of the electrode can be inferred, for example, when the electrodes on the left and right oxters contact with the body, whether the left and right arms are close to the body or do not move can be inferred, otherwise, leave the body.

The second method comprises the following steps: referring to the former embodiment 1, if the microcomputer dose not receive the interval time (normal interval time is about 1.5 s to 0.3 s) of normal R wave, Q wave or S wave within an extended period (for example 1 minute), the signal is judged as noise, the following situations may be appeared: I. the electrode is poorly contacted with the skin or the skin is different to conduct because of dry; II. The interference produced by body movement is large, the signal is saturated upwards or downwards and the R wave is difficult to read; III. The external electromagnetic interference is large.

Figure 27:
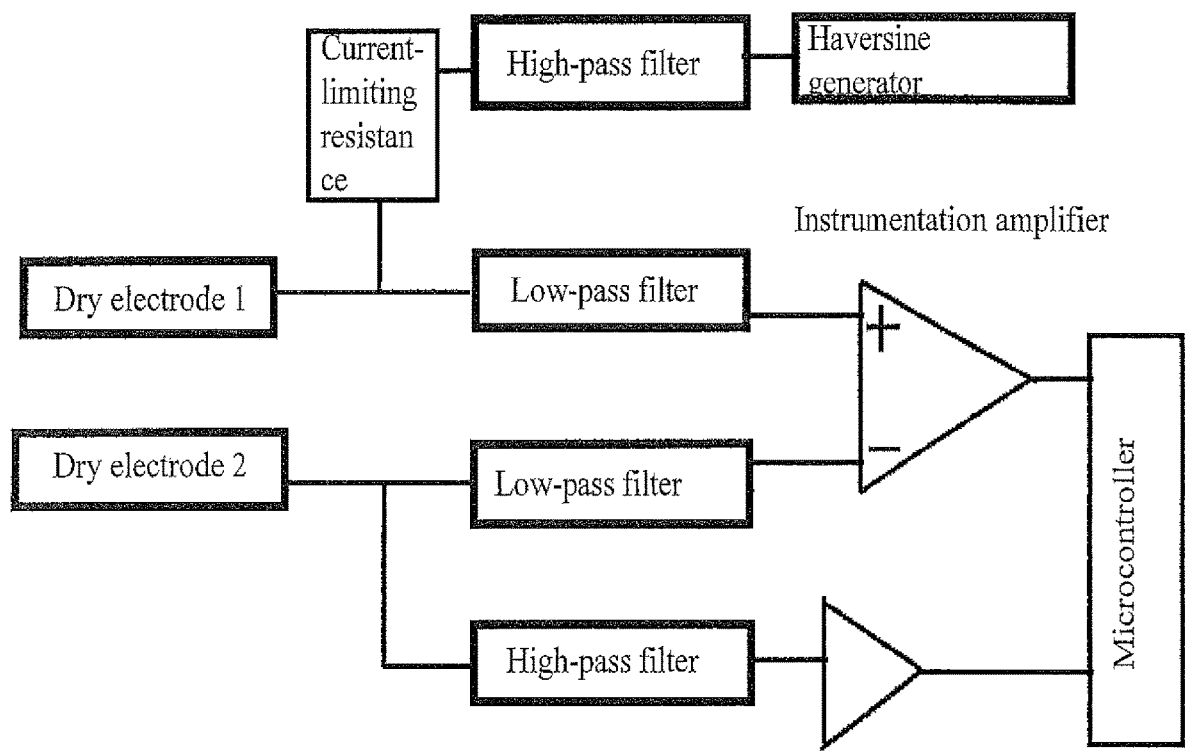
FIG. 27 is the schematic diagram that the sine wave detects whether the electrode is in good contact or not.

The third method is as shown in FIG. 27. FIG. 27 is the schematic diagram that the sine wave detects whether the electrode is in good contact or not. The current-limiting resistor (about 10 K Ohms), the high-pass filter formed by passive components and the high-frequency signal generator (such as the sine-wave generator) are connected on the input end of any electrode in turn; the high-press filter and the amplification circuit are connected on the input ends of other electrodes in turn, and finally connected to the analog input end of the microcomputer. If the sine-wave frequency is high enough, it can enter the muscular tissues and can return to the processor from the other electrode. If the amplification circuit of the electrode can obtain enough sine-wave, the impedance of the electrode is low. The low-pass filter is connected on the front end of the instrument amplifier, the low-frequency ECG signal (lower than 40 Hz) can be transmitted to the instrument amplifier, the sine-wave is prevented from entering so that the ECG signal is not interfered, meanwhile the ECG signal can be obtained, whether the electrode is poorly contacted can be detected through the sine-wave. As shown in FIG. 27, the circuit of the active electrode can be arranged to reduce the external electromagnetic interference and be beneficial to judge the noise.

The fourth method is applied by the current impedance pneumogram technology; if the respiratory rate can be read by the pneumogram, the electrode is adhered to the body; oppositely, if a large amount of high frequency components appear in the pneumogram, the high frequency is inferred as noise, because the breathing frequency of normal person is low (smaller than 1 Hz), the noise is responsible for poor contact.

Figure 28:
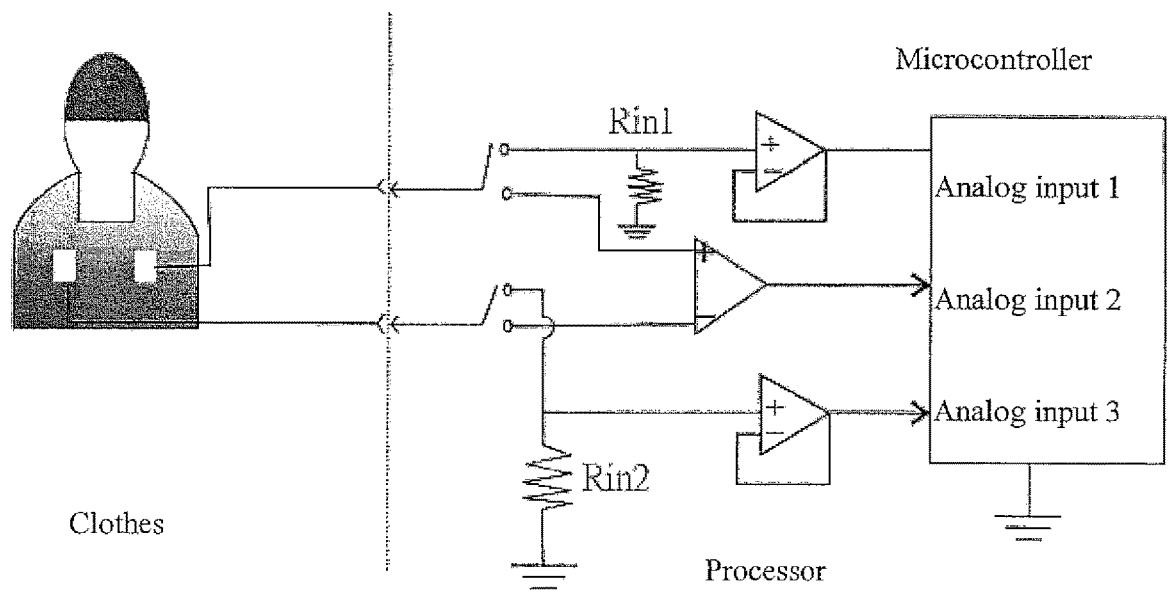
FIG. 28 is the schematic diagram of the fifth method for judging whether the contact of electrode and the skin is good or not.

As the circuits on the textile and the control box shown in FIG. 28, the fifth method is not to transmit any signal to the electrode so that the level of the electrode is close to floating, and then capture the single electrode to obtain the signal, wherein the impedance of the input end of to the calculation amplifier is its own inner resistors (shown as Rin1, Rin2). For enabling the input end to float with the external noise, the calculation amplifier of which the input impedance is larger than 100 M Ohms shall be adopted. In this case, if the electrode is perfectly contacted with the body, the body becomes a good conductor and is easily, capacitively and inductively coupled with the 50 or 60 Hz power supply, at this time, the single electrode can obtain a strong 50 or 60

Hz interference source, or the single electrode is not easily coupled to the 50 or 60 Hz interference source coming from the power supply because of short transmission wires, and only the weak irregular background noise which is similar to white noise is obtained.

Figure 29:
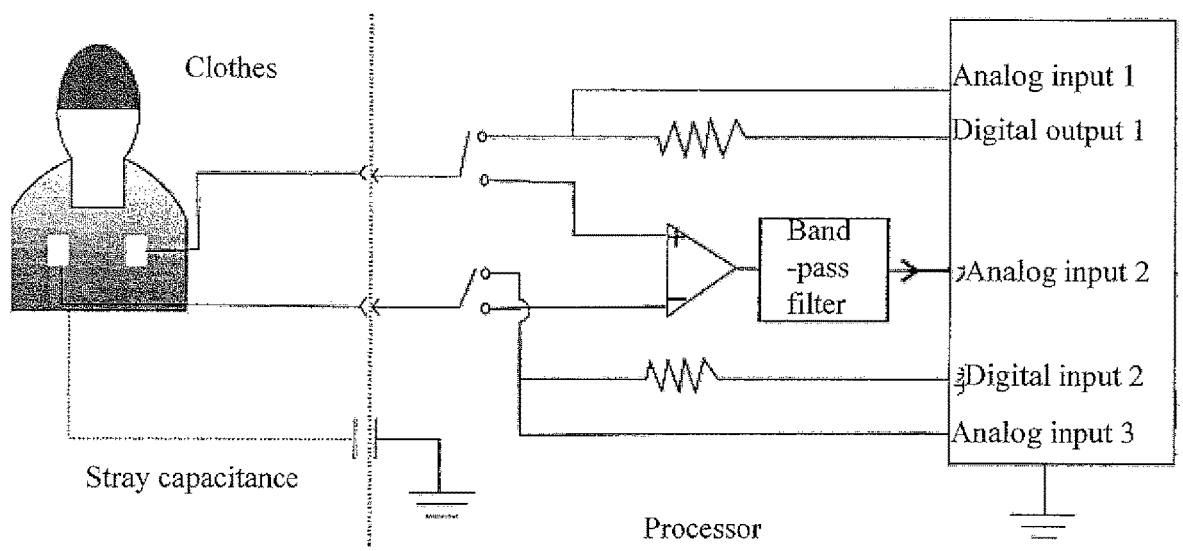
FIG. 29 is the schematic diagram of the sixth method for judging whether the contact of electrode and the skin is good or not.

As the circuits of the textile and the processor shown in FIG. 29, the sixth method is to transmit a pulse wave to the electrode, and record the voltage changes during the charging and discharging period. If the electrode is perfectly contacted with the body, the capacitance is formed between the body and the electrode, the closer contact, the higher capacitance value, the longer charging and discharging time. The processor is charged or discharged by the electrode, the current passes trough the stray capacitor between the processor and the body and then return to the processor arranged in the control box, oppositely, if the electrode is poorly contacted with the body, the capacitance value is low, and there is little charging and discharging time. The process can measure single charging and discharging time or measure the vibration frequency after continuously charged and discharged by the oscillating circuit (such as LM555), as shown in the embodiment 5, whether the electrode is poorly contacted with the skin can be judged. In order to increase the capacitance between the electrode and the body, a small sheet or a belt material with high relative dielectric constant can be selectively arranged on the electrode, such as nylon (the relative dielectric constant of the Nylon is 3.2), silica dioxide (the relative dielectric constant is 3.9), polyvinyl chloride (the relative dielectric constant of PVC is 3), copper calcium titanate (the relative dielectric constant of CCTO is 1000); and the method can be realized through the sine-wave.

Figure 30:
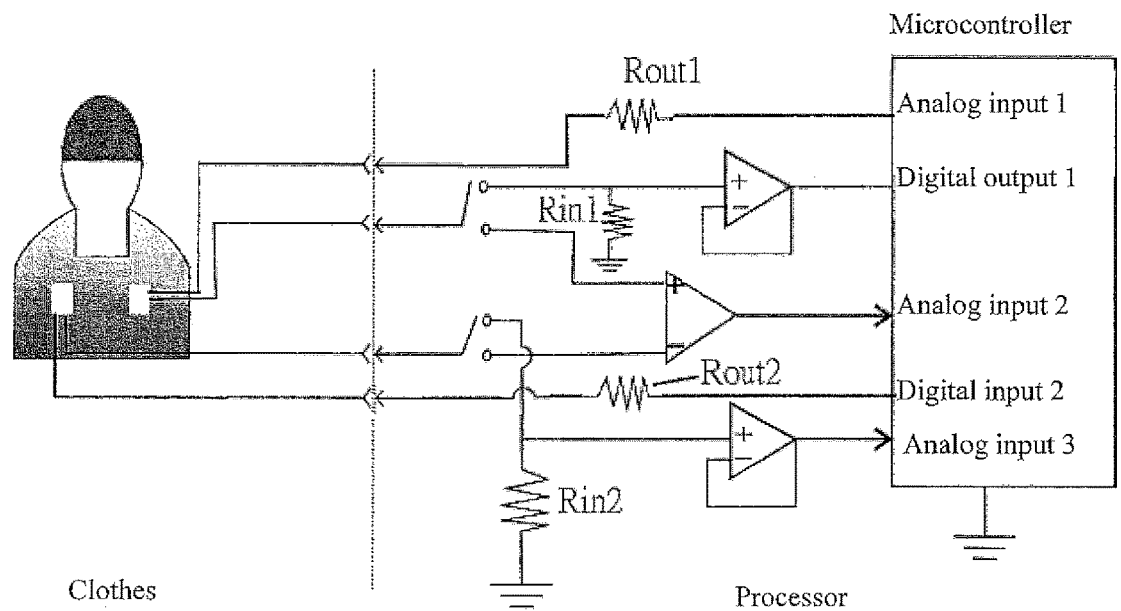
FIG. 30 is the schematic diagram of the seventh method for judging whether the contact of electrode and the skin is good or not.

The inner structure of the processor in the seventh method is shown in FIG. 30: one electrode comprises two transmission wires to connect the electrode with the processor; the microcomputer sends the sine-wave or the pulse wave, connect them to the electrode through one transmission wire and return to the microcomputer through the other one transmission wire; Rout1 and Rout2 adopt the impedance above 10M Ohms to be the same as stray capacitance and inductance. According to the analysis of the fifth method, if the electrode is perfectly contacted with the body, the body becomes a good conductor and is easily capacitively and inductively coupled with the 50 or 60 Hz power supply, the 50 or 60 Hz interference can be obtained by simulating to enter 1 or 3, or the 50 or 60 Hz interference can be easily obtained, thus whether the electrode is poorly contacted with the body can be judged, meanwhile, if the input signal does not have sine-wave or pulse wave, the transmission wire or the electrode may be damaged.

Figure 31:
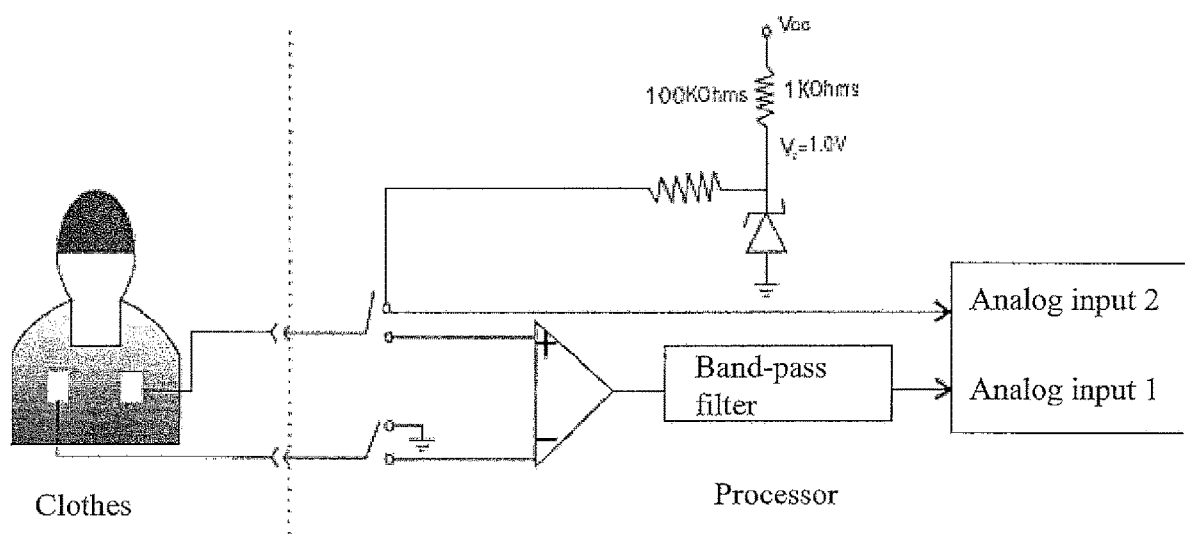
FIG. 31 is the schematic diagram of the eighth method for judging whether the contact of electrode and the skin is good or not.

The eighth method comprises the following steps of: evaluating whether the electrode is perfectly contacted by a manner of measuring the direct current resistance of the skin through the dry electrode, which is to arrange the analog switch on the input end of the processor as shown in FIG. 31, produce the direct current power supply of which the voltage is 1 Volt through the resistor and Zener diodes or similar reference voltage source to measure the direct current resistance; adopting the low voltage, which is to prevent the polarization and water electrolysis reaction on the electrode end, wherein the purpose of using the direct current is that the direct current cannot pass through the outermost cuticle of the skin, only small amount of direct current can enter the body through the sweat gland, a large amount of the direct current can flow to the other electrode from one electrode through the sweat on the skin, if the skin is drier, the electro-physiological signals cannot be easily transmitted to the electrode, namely the electrode is poorly contacted with the body.

In the embodiment, from the experimental results, when the direct current resistance of the electrodes on the left and right oxters is larger than 5000K Ohms, the skin is dry and the quality of the ECG signal is not good. The method similarly uses the multimeter to measure the resistance, the processor can detect whether the electrode is perfectly contacted by measuring; when the skin is dry, the processor can momentarily obtain the ECG signal through the dry electrode, and then obtain the ECG signal through the capacitive coupling electrode, or inform the user to wear clothes for keeping warm through the communication equipment, so that the sweat on the skin can be increased, and the quality of the ECG signal can be improved as shown in Table 2; when the direct current resistance of the skin is measured, whether the electrode is adhered to the skin is detected at the same time, if the value is stable, the electrode is not stably contacted, if the resistance value is large, one electrode is not adhered to the body.

The ninth method is to arrange the sensor near the electrode based on the textile to detect whether the electrode is adhered to the body and whether the part of the body moves. The textile sensor can adopt the textile strain gauge in the U.S. Pat. No. 7,750,790 provided by the applicant, or the fissure type tension sensor in the PCT/CN2008/001571, or the pressure sensor in the PCT/CN2008/001570, or other similar sensor. Meanwhile, the pressure and tension sensors can be adopted as one part of the electrode. FIG. 1(*a*) is presented to show that if detecting whether the electrodes on the left and right oxters are perfectly contacted, the textile sensor can be installed on the clothes between the two electrodes, when person wear the clothes and feel comfortable, the elasticity of the clothes textile will produce the pull force, pressure on the body will be produced by the pull force, and the textile sensor can detect the pull force or the pressure, oppositely, if the clothes is loose, the clothes does not have enough pressure or pull force to ensure that the electrode is perfectly contacted. On the other hand, if the pull force or the pressure detected by the textile sensor is maintained in a certain range and not changed, the user does not move, namely there is no body movement interference, otherwise, if the pull force or the pressure is changed, the user moves, namely there is body movement interference.

The tenth method is to clamp an insulated fabric between the two conductive fabric to form the capacitive pressure or tension sensor, wherein the insulator can be the elastomer or the material with high dielectric constant. Under the action of the external pressure or the pull force, the capacitance value is changed. The processor can adopt the circuit in the first method in the embodiment 5 to measure the capacitance value. The capacitive pressure or tension sensor can be arranged between the clothes and the body, the capacitance value is changed while the postures of person are changed. The processor can set a critical value, namely under a certain level of the pressure, the physiological signals are received, for example, when the pressure is larger than the critical value, the electrocardiogram detection is started. If the capacitance value is greatly changed, there is the body movement interference. Meanwhile, one of the two conductive fabrics which is close to the body can be adopted as the resistance (dry) electrocardiogram electrode, and the other fabric can be adopted as the capacitive coupling electrocardiogram electrode, so that the two conductive fabrics form a capacitor which is adopted as a switch; at the same time, the conductive fabrics can be adopted as the electrodes, so they can detect the poor contact.

In the embodiment 2 above, the invention discloses the method for estimating the body movement by noise, similarly, the embodiment can adopt the method for estimating the body movement by detecting the impedance of the electrodes, for example, some electrode is arranged on the oxter, when the electrode is poorly contacted, the arms are not close to the body.

In addition, the embodiment can be applied to the electrodes used for testing whether the electrodes are perfectly contacted in electroencephalogram, electromyography, transcutaneous electrical nerve stimulation and electric-shock treatments.

The eleventh method is to adopt other physiological signal sensors to judge whether the electrodes is close to the body. Except the electrocardiogram electrodes, other physiological signal sensors can be installed on the textile which is contacted with the body, for example, stethoscopes (must be completely contacted with the body but can detect the heart and lung sound without waiting for the transient response), ultrasonic probes, thermometers (must wait for the transient response for 3 min, if the body temperature is suddenly changed, the sensors are not close to the body), blood oxygen saturation meters (must be wait for the transient response for 20 s), sphygmomanometers (if the blood pressure value is not stable, person moves), etc. The embodiment can arranged the electrocardiogram electrodes beside the sensors, when the electrocardiogram electrodes are perfectly contacted, the sensors are perfectly contacted, and good signals can be obtained. The embodiment can arrange other biosensors beside the electrodes, for example, electromyography sensors, blood oxygen saturation meters, thermometers, heart and lung sound sensors, or ultrasonic rheometers, etc. The body movement interference can be estimated by analyzing the signals or the noise of other biosensors, for example, when the electromyography sensor capture the large signal, the muscle activity is intense, namely there is the body movement interference; similarly, when the blood oxygen saturation meter capture the violent shaking noise but does not have the stable pulse wave, there is the body movement interference.

Otherwise, if the sensors have good signal, the electrocardiogram electrodes are perfectly contacted.

From the methods above, the processor can measure the impedance of each electrode to select the two electrodes of which the impedance is lowest, or select the electrode by using other methods to capture the ECG signal and obtain the best signal quality.

Z In the eleven methods above, the output value used for judging whether the electrode is perfectly contacted with the body, for example, the pulse frequency which is changed while the capacitance value is changed, is changed because of the body movement. The amplitude of the output value is responsible for the level of the movement, the more intense movement, the larger amplitude; if the body is under the standing conditions or the electrode is perfectly contacted with the body, the output value is stable, therefore, the level and the states of the body movement can be judged according to the amplitude of the output value.

If adopting any method above, whether the electrode is perfectly contacted with the body can be detected, but the long-term stable heartbeat signal cannot be obtained, which means that the electrode or the transmission wires are poorly contacted. At this time, the method in the embodiment 7 is adopted to inspect and maintain as follows.

Embodiment 7

Judge Whether Transmission Wires or Electrodes Poorly Conducted

Figure 32:
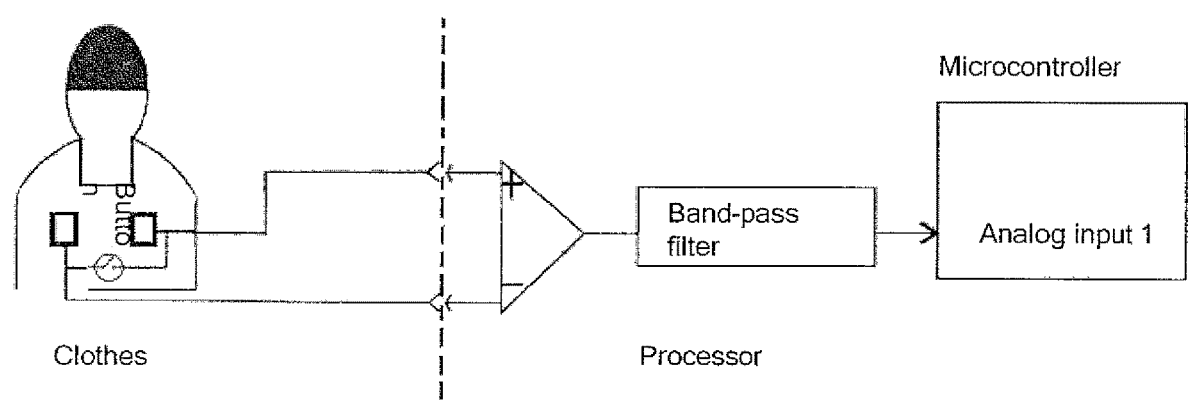
FIG. 32 is the schematic diagram for judging whether the transmission line has poor breakover or not.

In the invention, kneading in the normal washing can be born, if the kneading force is large, the transmission wires or the electrodes may be damaged, and the ECG signal cannot be transmitted to the control box. The embodiment provides two methods:

The first method is to judge whether the transmission wires are poorly conducted by using the processor as shown in FIG. 32. Take the dry electrodes on the left and right oxters as example, except that one transmission wire is connected to the processor, the other transmission wire is connected to the two electrodes, serially connected with a push button switch or a toggle switch, and arranged on the textile in the invention. The transmission wires are not conducted when the push button switch is not pressed. The button is pressed when user wants to inspect whether the transmission wires or the electrodes are poorly conducted or damaged; if the transmission wires are good channels, the signal output is a horizontal beeline which approximates to zero; if the transmission wires are damaged, the signal output is troublous noise. The signal outputs in the two conditions are greatly different, whether the transmission wires or the electrodes are poorly conducted by eyes of users or the program in the control box according to the amplitude of the noise.

The second method is the same as the first method on the textile, which is to connect the two electrodes through another transmission wire, wherein the transmission wire is serially connected with the push button switch or the toggle switch, the difference is that the processor adopts the structure in FIG. 29 or FIG. 30, the pulse wave or the sine-wave transmitted by the processor through the output resistor, the electrode and the transmission wires is adopted as the carrier wave for test, and passes through the other transmission wire which connecting the two electrode, the serially connected the push button switch or the toggle switch, and the other electrode with the transmission wire thereof; if the wires or the electrodes of this path are not damaged, the carrier wave returns to the control box, by which judges whether the transmission wires are damaged. In addition, the amplitudes of the output wave and the return wave are compared, if the difference is large, the conductivity of the transmission wires is not good; the system has faults, shall be maintained and not be continuously used. Similarly, we can use the same method to judge whether some section of the electrode or the wire is poorly conducted, which is to arrange another transmission wire on the two ends of the electrode or the wire to be tested, wherein the transmission wire is serially connected the push button switch or the toggle switch. Meanwhile, comparison of the frequency spectrums of the output wave and the return wave means the external noise interference. For example, we know the frequency spectrum of the carrier wave and its signal-to-noise ratio (S/N) near the main frequency zone, and then analyze the S/N near the main frequency zone of the frequency spectrum of the return wave, the difference of the two is the quantitative pointer of the external noise interference. If the transmission wires and the electrodes are perfectly conducted, the difference of the two is extra small, or extra large.

Generally speaking, the process that the conductivity of the transmission wires or the electrodes becomes bad from good even is damaged is a gradual process, and the conductivity will be gradually reduced, not instantly disappears. Therefore, in the invention, the threshold value of the quantitative pointer (noise amplitude in the first method, the S/N difference between the carrier wave and the return wave near the main frequency zone in the second method) of the output in the two methods can be set for each transmission wire and electrode, for example, threshold value of the first method is 50% of the factory value, when the electrode or the transmission wire is damaged and the quantitative pointer reaches the threshold value, users are reminded to maintain to ensure the good working quantity. The maintaining method is to arrange the sutures on the connection points of the conductors of the poorly-conducted electrodes and transmission wires so as to strengthen the conductivity, or sew one conductor or conductive fabric.

The descriptions above are the better embodiments of the invention, which does not limit the invention in any form, though the better embodiments of the invention are disclosed, the invention is not limited; any technician who is familiar with the specialty can use the disclosed method and the technical content to change or decorate the content within the scope of the technical scheme of the invention to form the equivalent embodiments which are equally changed, but for the content within the scope of the technical scheme of the invention, in accordance with technology in the invention, the any simple and essential modification, equivalent changes and decorations of the embodiments are within the scope of the technical scheme of the invention.

The invention claimed is:

1. An object for detecting heartbeat or whether an electrode is in good contact with a wearer's body, comprising:
   a textile,
   at least two electrodes for picking up ECG (electrocardiogram) signals, wherein said at least two electrodes are separated electrodes that are separated from the textile and constructed with a first surface and a second surface,
   a smooth fabric arranged between a first surface of the textile and the second surface of the separated electrodes,
   a first non-conductive wire connecting the at least one separated electrode and the smooth fabric, and a second non-conductive wire connecting the smooth fabric and the textile, wherein said first non-conductive wire is configured to suspend the at least one separated electrode from the first surface of the textile,
   wherein the at least one separated electrode is slideable or rollable above on the textile when the at least one separated electrode is pressed by the wearer's body.

2. The object of claim 1, wherein a position of the separated electrodes and a length of a transmission line are set by considering any or all of: the isopotential map of ECG signals, relative skin displacement distance, isothermal line, and/or constant moisture line.

3. The object of claim 1, wherein the at least two electrodes are selected from a group consisting of dry electrodes, capacitive coupling electrodes, and combination thereof.

4. The object of claim 1, wherein the first or second non-conductive wire is selected from a group consisting of suspension bars, nylon wire, elastomeric yarn, cloth wire, cloth strip, braid, plastic wire, plastic strip, helical connecting wire, helical connecting wire with increasing radius, strip connecting wire, belt connecting wire, and suspended strip.

5. The object of claim 1, wherein the textile is one or more selected from a group consisting of shirt, sportswear, casual wear, pajamas, wearpants, panties, underwear, underclothes, coat, sheet, pillow, socks, shoes, scarf, kerchief, glove, apron, waistband, toilet seat, carpet, cap, seat cushion, steering wheel cover, and watchband.

6. The object of claim 1, wherein the separated electrodes are in connection with a control box, the control box is configured to detect a heartbeat from a measured R wave of the wearer when an electrode impedance between the separated electrodes is less than 2 MΩ or a capacitance value between the separated electrodes is more than 5 nF.

7. The object of claim 1, wherein a length of the first or second non-conductive wire is determined based on the distance of relative movement of skin with respect to the textile.

8. The object of claim 1, wherein the separated electrodes are in connection with a control box, a processor arranged in the control box, the processor being configured to calculate the heart rate or determine whether the separated electrodes are in good contact with the wearer's body by measuring an impedance of the separated electrodes or noise in the ECG signals and human motion or posture is estimated by using the noise drawn by the processor or the obtained ECG signals or the impedance.

9. The object of claim 8, wherein the control box comprises a microcontroller and a circuit for measuring the impedance of the separated electrodes; the microcontroller is configured to activate different circuits, firmware or software based on the impedance between the separated electrodes, or the microcontroller is configured to start an electrocardiogram, electromyogram, electroencephalogram, impedance pneumograph, transcutaneous electrical nerve stimulation, electric shock circuit, body fat meter or sweat meter.

10. The object of claim 1, wherein a wireless transmission system is arranged in the at least one of the at least two electrodes to send the signals.

11. An object for detecting heartbeat or whether an electrode is in good contact with a wearer's body, comprising:
    a textile,
    at least two electrodes for picking up ECG signals arranged at a position between the textile and a skin surface, wherein said at least two electrodes comprise at least one separated electrode separated from the textile and constructed with a first surface, the at least one separated electrode is also constructed with a second surface opposite to the first surface, and
    a connecting wire connected with the textile and the at least one separated electrode, and configured to suspend the at least one separated electrode from the first surface of the textile when the first surface of the at least one separated electrode is not in contact with the skin surface,
    wherein the at least one separated electrode itself is of permanent magnetic substance or permanent magnetic substance is installed outside the at least one separated electrode; the textile opposite to the at least one separated electrode is also provided with the permanent magnetic substance, where magnetic poles of the permanent magnetic substance of the at least one separated electrode and the permanent magnetic substance of the textile are same such that the at least one separated electrode is repelled by magnetic force to move toward skin.

12. The object of claim 1, wherein the separated electrodes or the textile are provided with a passage; the at least one of the first non-conductive wire and the second non-conductive wire passes through the passage to connect with the separated electrodes, or textile.

13. The object of claim 1, wherein the separated electrodes or the textile are provided with a hole; the at least one of the first non-conductive wire and the second non-conductive wire passes through the hole to connect with the separated electrodes, or textile.

14. The object of claim 9, wherein the processor is configured to select a band-pass filter with a first frequency band to capture complete ECG when the electrode impedance is reduced below a threshold for a period of time; the processor is configured to select a band-pass filter with a second frequency band to capture R wave and meanwhile reduce an interference, or detect the heart rate through Hilbert-Huang transform when the electrode impedance is between 2 M Ohms and 20 M Ohms, wherein the first frequency band is wider than the second frequency band.

15. The object of claim 1, further comprising a non-slip bar on the first surface of the separated electrodes.

16. The object of claim 1, wherein the at least one of the first non-conductive wire and the second non-conductive wire is a braid folded between the textile and the separated electrodes.

17. The object of claim 1, wherein separated electrodes comprise an elastomer therein.

18. The object of claim 1, wherein the separated electrodes comprise an air bag or a liquid bag therein.

* * * * *